US009757379B2

(12) United States Patent
Bruick et al.

(10) Patent No.: US 9,757,379 B2
(45) Date of Patent: Sep. 12, 2017

(54) INHIBITION OF HIF-2α HETERODIMERIZATION WITH HIF1β (ARNT)

(71) Applicant: The Board of Regents of the University of Texas System, Austin, TX (US)

(72) Inventors: Richard K. Bruick, Dallas, TX (US); Charles G. Caldwell, Dallas, TX (US); Doug E. Frantz, Boerne, TX (US); Kevin H. Gardner, Carrollton, TX (US); John B. MacMillan, Dallas, TX (US); Thomas H. Scheuermann, Richardson, TX (US); Uttam K. Tambar, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/442,485

(22) PCT Filed: Nov. 14, 2013

(86) PCT No.: PCT/US2013/070000
§ 371 (c)(1),
(2) Date: May 13, 2015

(87) PCT Pub. No.: WO2014/078479
PCT Pub. Date: May 22, 2014

(65) Prior Publication Data
US 2016/0250216 A1     Sep. 1, 2016

Related U.S. Application Data

(60) Provisional application No. 61/726,437, filed on Nov. 14, 2012, provisional application No. 61/778,080, filed on Mar. 12, 2013.

(51) Int. Cl.
| | | |
|---|---|---|
| *A61K 31/41* | (2006.01) | |
| *A61K 31/519* | (2006.01) | |
| *A61K 31/4245* | (2006.01) | |
| *A61K 31/136* | (2006.01) | |
| *A61K 31/4184* | (2006.01) | |
| *A61K 31/4192* | (2006.01) | |

(52) U.S. Cl.
CPC .......... *A61K 31/519* (2013.01); *A61K 31/136* (2013.01); *A61K 31/4184* (2013.01); *A61K 31/4192* (2013.01); *A61K 31/4245* (2013.01)

(58) Field of Classification Search
CPC .................................................. A61K 31/519
USPC ...................................................... 514/362
See application file for complete search history.

(56) References Cited

U.S. PATENT DOCUMENTS

| | | | |
|---|---|---|---|
| 5,641,432 A | 6/1997 | Ohnishi et al. | |
| 2005/0074846 A1* | 4/2005 | Gardner | C07H 21/04 435/69.1 |
| 2009/0176745 A1* | 7/2009 | Arbiser | A61K 31/136 514/114 |
| 2010/0330098 A1 | 12/2010 | Kuo et al. | |

FOREIGN PATENT DOCUMENTS

| | | |
|---|---|---|
| WO | WO 2007/131168 | 11/2007 |
| WO | WO 2013/064714 | 5/2013 |
| WO | WO 2013/134376 | 9/2013 |

OTHER PUBLICATIONS

Rogers et al. Journal of Medicinal Chemistry (2013), 56(4), 1739-1747.*
Key et al. J. Am. Chem Soc. 2009, 131, 17647-17654.*
Rogers et al. J. Med. Chem. 2013, 56, 1739-1747.*
Venkatesh et al., J. Pharm. Sci. 89, 145-54 (2000).*
Amezcua et al. Structure, vol. 10, 1349-1361, 2002.*
Ghosh et al Journal of Medicinal Chemistry (1969), 12, 505-7.*
Levinson, STN Accession No. 1989:23227, Abstract of Zhurnal Obshchei Khimii (1988), 58(5), 1080-2.*
Bruick et al., "Targeting transcription factors: identification of natural and artificial ligands regulating hypoxia inducible factor 2," 2012.
Covello et al., "Targeted replacement of hypoxia-inducible factor-1alpha by a hypoxia-inducible factor-2alpha knock-in allele promotes tumor growth," *Cancer Res.*, 65:2277-2286, 2005.
Gardner et al., "Identification of natural and artificial ligands regulating hypoxia inducible factor 2 (HIF-2)," *CPRIT Cancer Research and Prevention Conference*, 2011.
Gardner et al., "Modulation of HIF-2 function with small molecules: did nature beat us t it?" *American Society of Hematology*, 2011.
Gardner, "NMR-based discovery of novel environmental sensing machineries," *Frontiers in NMR Symposium*, Mar. 23, 2011.
Giaccia et al., "HIF-1 as a target for drug development," *Nat Rev Drug Discov.*, 2:803-811, 2003.
Harris, "Hypoxia—a key regulatory factor in tumour growth," *Nature Rev. Cancer*, 2(10):38-47, 2002.
Jiang et al., "Dimerization, DNA binding, and transactivation properties of hypoxia-inducible factor 1," *J. Biol. Chem.*, 271:17771-17778, 1996.
Key et al., "Principles of ligand binding within a completely buried cavity in HIF 2α PAS-B," *J. Am. Chem. Soc.*, 131(48):17647-17654, 2009.
Lee et al., "Acriflavine inhibits HIF-1 dimerization, tumor growth, and vascularization," *Proc Natl Acad Sci U.S.A.*, 106:17910-17915, 2009.

(Continued)

*Primary Examiner* — Nizal Chandrakumar
(74) *Attorney, Agent, or Firm* — Parker Highlander PLLC

(57) ABSTRACT

Provided is a method of inhibiting heterodimerization of HIF-2α to HIF1β (ARNT) comprising binding certain small molecules to the HIF-2α PAS-B domain cavity but not to HIF1α and inhibiting HIF-2α heterodimerization to HIF1β (ARNT) but not inhibiting HIF1α heterodimerization to HIF1β (ARNT). Those certain small molecules are also referenced synonymously as HIF2-HDI and HIF2α heterodimerization inhibitors and also simply as certain small molecules.

5 Claims, 26 Drawing Sheets

(56) References Cited

OTHER PUBLICATIONS

McKee et al., "Inhibition of Hypoxia Inducible Factor-2 Transcription: Isolation of Active Modulators from Marine Sponges," *J. Natural Products*, 75(9):1632-1636, 2012.
Park et al., "Targeting the PAS-A domain of HIF-1α for development of small molecule inhibitors of HIF-1," *Cell Cycle*, 5(16):e1-e7, 2006.
PCT International Preliminary Report on Patentability issued in International Application No. PCT/US2013/070000, mailed May 28, 2015.
PCT International Search Report and Written Opinion issued in International Application No. PCT/US2013/070000, mailed May 1, 2014.
Rodríguez-Jiménez et al., "Modulation of hypoxia-inducible factors (HIF) from an integrative pharmacological perspective," *Cell. Mol. Life Sci.*, 69:519-534, 2012.
Scheuermann et al. "Artificial ligand binding within the HIF-2α PAS-B domain of the HIF2 transcription factor," *Proc Natl Acad Sci USA*, 106:450-455, 2009.
Semenza, "Hypoxia-inducible factors in physiology and medicine," *Cell*, 148:399-408, 2012.
Semenza, "Oxygen sensing, hypoxia-inducible factors, and disease pathophysiology," *Annu. Rev. Pathol. Mech. Dis.*, 9:47-71, 2014.
Zimmer et al, "Inhibition of hypoxia-inducible factor is sufficient for growth suppression of VHL-/- tumors," *Mol. Cancer Res.*, 2:89-95, 2004.
Cardoso et al., "Identification of Cys255 in HIF-1α as a novel site for development of covalent inhibitors of HIF-1α/ARNT PasB domain protein-protein interaction," *Protein Science*, 21:1885-1896, 2012.
Extended European Search Report issued in European Application No. 13854318.6, mailed Feb. 7, 2017.
Ghosh and Whitehouse, "Potential antileukemic and immunosuppressive drugs. Preparation and in vitro pharmacological acitivity of some benzo-2,1,3-oxadiazoles (benzofurazans) and their N-oxides (benzofuroxans)," *Journal of Medicinal Chemistry*, 11(2):305-311, 1968.
Scheuermann et al., "Allosteric inhibition of hypoxia inducible factor-2 with small molecules," *Nat Chem Biol.*, 9(4):271-276, 2013.
Scheuermann et al., "Isoform-Selective and Stereoselective Inhibition of Hypoxia Inducible Factor-2," *J Med Chem.*, 58(15):5930-5941, 2015.

* cited by examiner

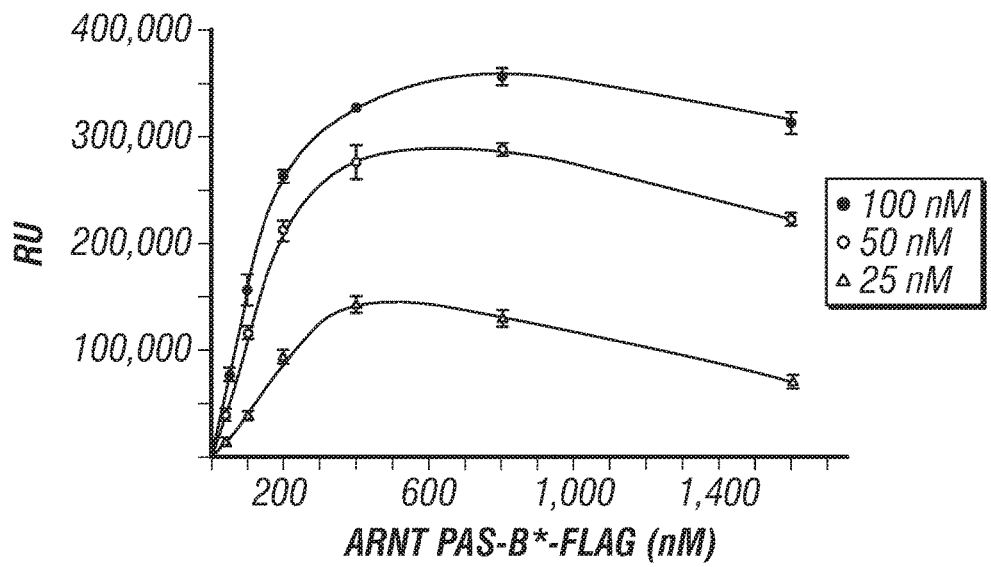
FIG. 8B
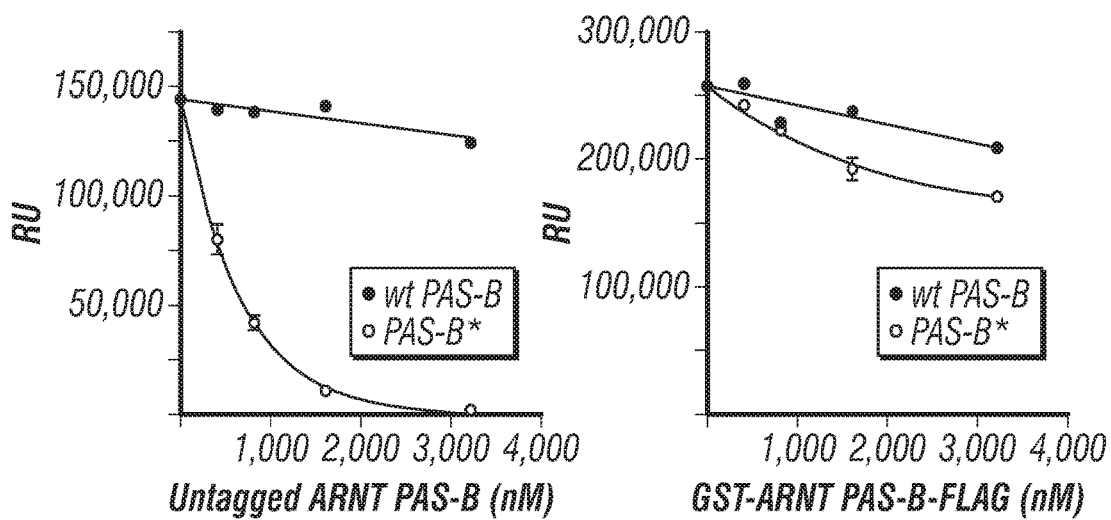
FIG. 8C
FIG. 8D

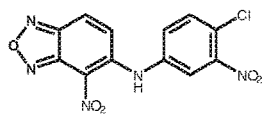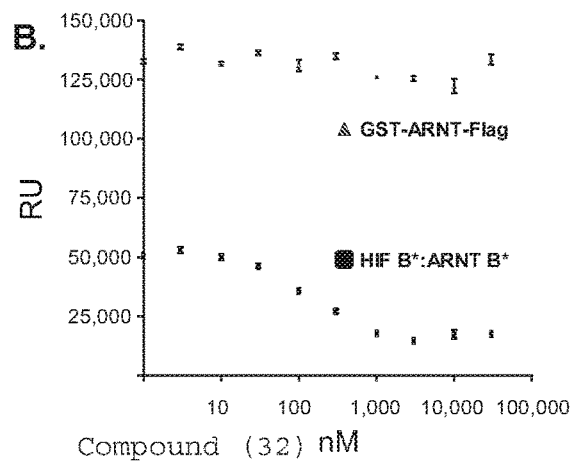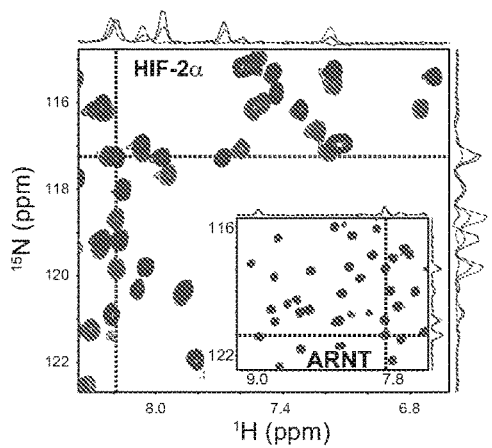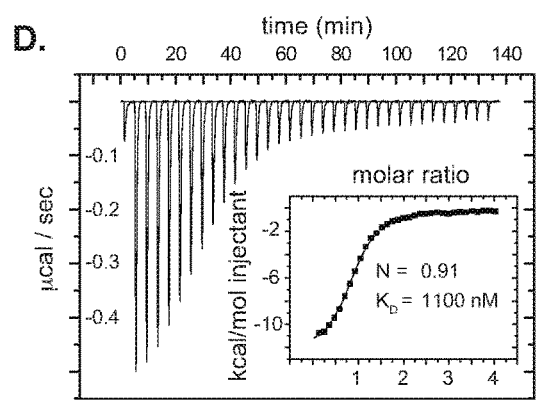
FIGS. 9A-D

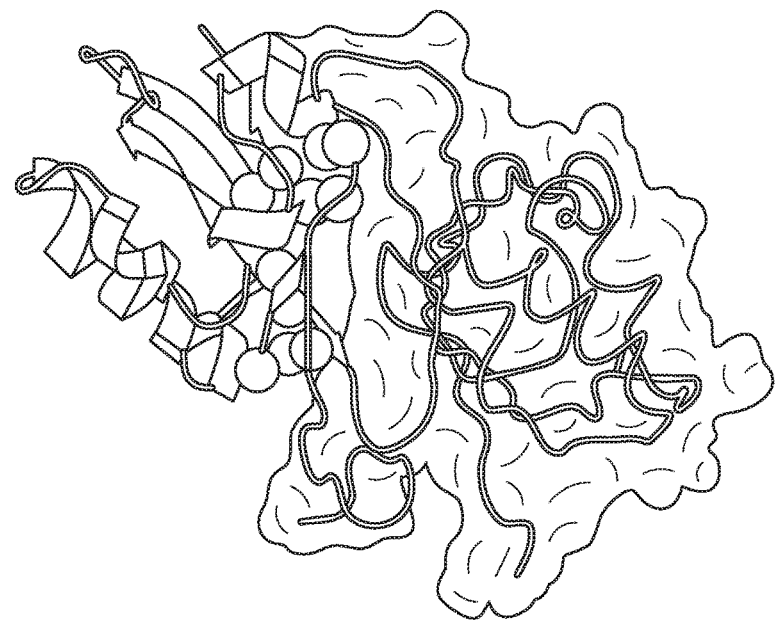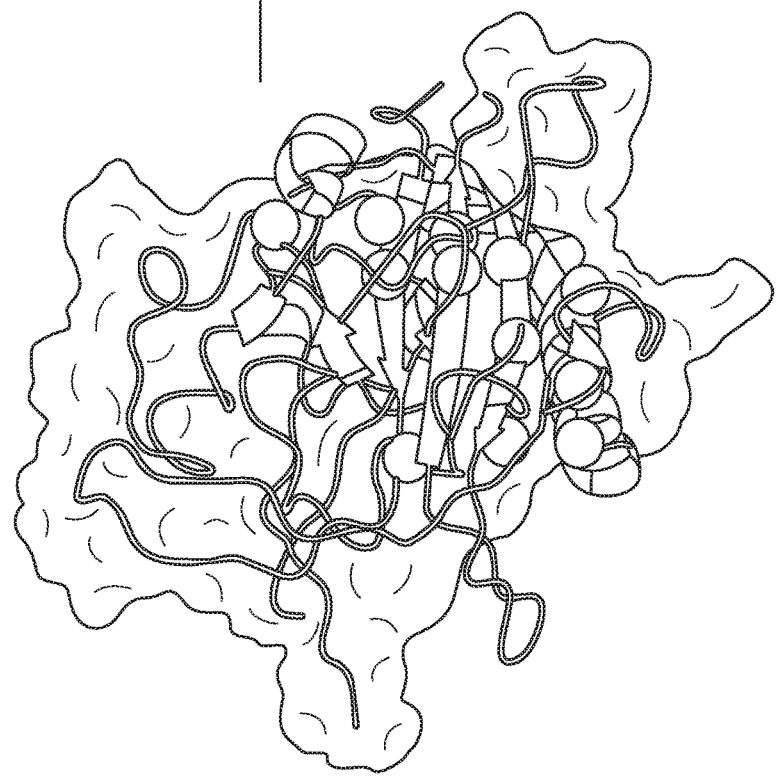
FIG. 15D

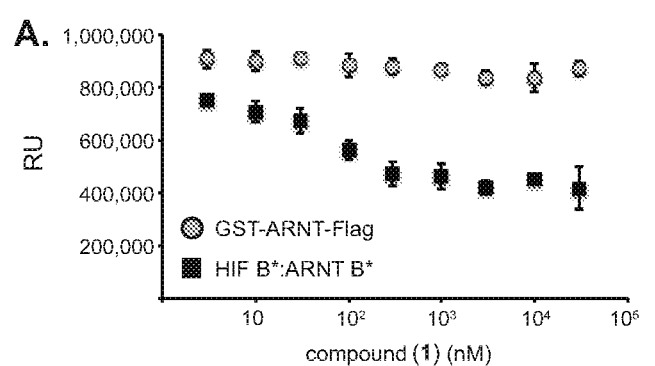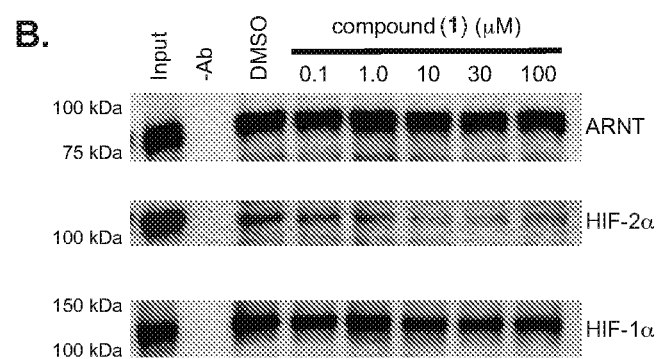
FIGS. 16A-B

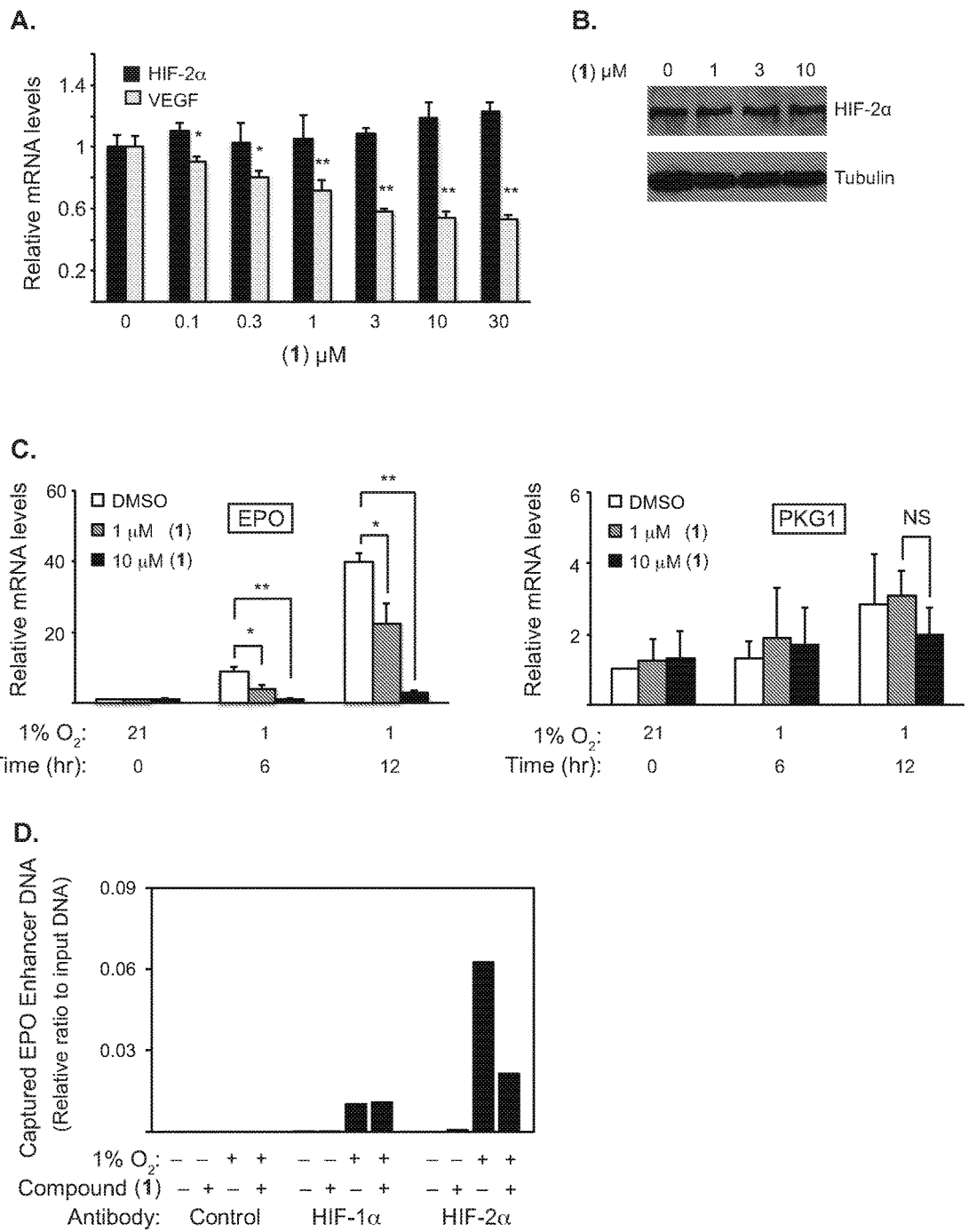
FIGS. 18A-D

A
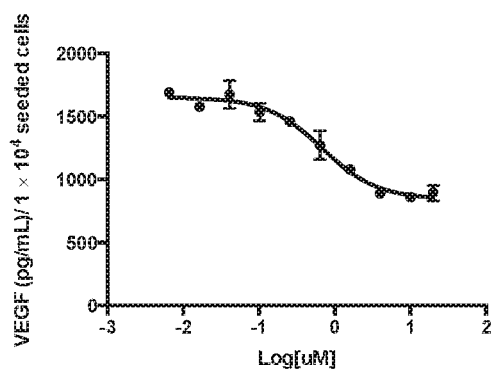
Compound 1, $EC_{50}$: 0.6828 μM
B
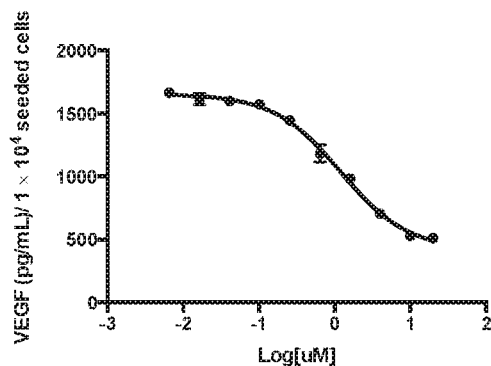
Compound 47, $EC_{50}$: 1.203 μM
FIGS. 19A-B

INHIBITION OF HIF-2α HETERODIMERIZATION WITH HIF1β (ARNT)

PRIORITY CLAIM

The present application is a national phase application under 35 U.S.C. 371 of International Application No. PCT/US2013/070000, filed Nov. 14, 2013, which claims benefit of priority to U.S. Provisional Application Ser. No. 61/726,437, filed Nov. 14, 2012, and 61/778,080, filed Mar. 12, 2013, the entire contents of each application being hereby incorporated by reference.

STATEMENT OF FEDERAL FUNDING

This invention was in part funded by grants from the National Institutes of Health (NIH) (P01 CA095471), CPRIT (RP-100846), CPRIT Grant the Cancer Center Support and Grant 5P30 CA 142543. Results shown in this disclosure were partially derived from work performed at Argonne National Laboratory, Structural Biology Center at the Advanced Photon Source. Argonne National Laboratory is operated by UChicago Argonne, LLC, for the U.S. Department of Energy, Office of Biological and Environmental Research under contract DE-AC02-06CH11357. Results shown in this disclosure were also partially conducted in a facility constructed with support from the Research Facilities Improvement Program (Grant # C06 RR 15437-01) from the National Center for Research Resources, NIH. The government has certain rights in the invention.

BACKGROUND

A. Field of the Disclosure

The present disclosure relates to certain small molecules that bind to the HIF-2αPAS-B domain cavity but do not bind to HIF1α and inhibit heterodimerization of HIF-2α to HIF1α (ARNT) but do not inhibit heterodimerization of HIF1α to HIF1β (ARNT).

B. Related Art

An adequate supply of oxygen to tissues is essential in maintaining mammalian cell function and physiology. A deficiency in oxygen supply to tissues is a characteristic of a number of Pathophysiologic conditions in which there is insufficient blood flow to provide adequate oxygenation, for example, ischemic disorders, cancer, and atherosclerosis. The hypoxic (low oxygen) environment of tissues activates a signaling cascade that drives the induction or repression of the transcription of a multitude of genes implicated in events such as angiogenesis (neo-vascularization), glucose metabolism, and cell survival/death. A key to this hypoxic transcriptional response lies in the transcription factor, the hypoxia-inducible factor (HIF). HIF is overexpressed in a vast array of cancers through hypoxia-dependent and independent mechanisms and expression is associated with poor patient prognosis.

Human cells require adequate supply of $O_2$ on a continuous basis in the process of mitochondrial respiration that generates ATP, which is used to drive most biochemical reactions. Both the delivery and consumption of $O_2$ are precisely regulated through the activity of HIFs. As cells proliferate, increased $O_2$ consumption results in hypoxia (reduced $O_2$ levels), which activates HIFs, leading to transcription of the VEGF gene, which encodes vascular endothelial factor, a secreted protein that stimulates angiogenesis and thereby increases $O_2$ delivery. Cancer cells are characterized by dysregulated cell proliferation, and the blood vessels that form within solid tumors are often structurally and functionally abnormal, resulting in severe hypoxia. To adapt to the hypoxic microenvironment, cancer cells co-opt physiological responses to hypoxia that are mediated by HIFs. In the process, hypoxic cancer cells acquire invasive and metastatic properties as well as resistance to chemotherapy and radiation therapy, which together constitute the lethal cancer phenotype. Few drugs in the cancer armamentarium target hypoxic cancer cells and none targets HIF-2α PAS-B domain cavity. The options for treatment of advanced metastatic disease—as well as the efficacy of such drugs—are extremely limited, and this year over 570,000 Americans will die of cancer. American Cancer Society (2011) Cancer Facts & Figures 2011.

HIFs consist of an oxygen-sensitive HIFα subunit and constitutively expressed HIFβ subunit. When HIFs are activated, the HIFα and HIFβ subunits assemble a functional heterodimer, i.e., the α subunit heterodimerizes with only the β subunit, the HIF1β, also called ARNT (aryl hydrocarbon receptor nuclear translocator). Both HIFα and HIFβ have two identical structural characteristics, i.e., basic helix-loop-helix (bHLH) and PAS domains (PAS is an acronym referring to the first proteins, PER, ARNT, SIM, in which this motif was identified). Jiang, B. H. et al., J. Biol. Chem. 271 (1996) 17771-17778. There are three human HIFα subunits (HIF1α, HIF2α, and HIF3α) that are oxygen sensitive. Among the three subunits, HIF1α is the most ubiquitously expressed and induced by low oxygen concentrations in many cell types. HIF2α is highly similar to HIF1α in both structure and function, but exhibits more restricted tissue-specific expression, and might also be differentially regulated by nuclear translocation. HIF3α also exhibits conservation with HIF1α and HIF2α in the HLH and PAS domains. HIFβ, the dimerization partner of the HIFα subunits (also referred to as ARNT—Aryl Hydrocarbon Receptor Nuclear Translocator) is constitutively expressed in all cell types and is not regulated by oxygen concentration.

HIF-1 driven transcription factor activity plays a central role in compensating for loss of oxygen. Thus, modulating that activity could be a potent mechanism for treating a wide range of hypoxia-related pathologies. Increases in HIF-1 activity could increase survival during hypoxia, and could also increase angiogenesis at sites of vascular disruption or dysfunction. Decreased HIF-1 activity could prevent the survival or angiogenic activity of pathological tissues with hypoxic regions, i.e., solid tumors. In tumors, HIF1α is overexpressed compared with adjoining normal tissue. This overexpression of HIF1α is due to both hypoxia-dependent as well as hypoxia-independent pathways, such as oncogen activation and glucose deprivation. Overexpression of HIF1α and HIF2α has been reported as a poor prognostic indicator for a variety of tumors. Harris, A. L., Nature Rev. Cancer 2(10): 38-47 (2002). HIF1α has been a target for drug development. See Giaccia, A. et al., Nature Reviews 2: 803-11 (2003).

A growing number of chemical compounds have been reported to block tumor xenograft growth and inhibit HIF activity through a wide variety of molecular mechanisms, including decreased HIF1α mRNA levels, decreased HIF1α protein synthesis, increased HIF1α degradation, decreased HIF subunit heterodimerization, decreased HIF binding to DNA, decreased HIF transcriptional activity. Aminoflavone, the active component of the prodrug AFP-464, partially inhibits HIF1α mRNA expression but almost completely blocks HIF1α protein expression. HIF1α protein synthesis has been blocked by drugs, such as rapamycin, temsirolimus, and everolimus, cardiac glycosides, microtubule targeting agents, such as taxotere, and topoisomerase inhibitors, such as topotecan. Drugs that induce degradation of HIF1α include HSP90 inhibitors, e.g., 17-allylamino-17-demthoxygeldanamycin, and antioxidants, such as ascorbate. Acriflavine, an antibacterial agent, is reported to bind directly to the PAS-B domain of HIF1α and HIF2α and blocks their interaction with HIF1β, thereby blocking HIF-dependent gene transcription and leading to impaired tumor growth and vascularization. Lee et al. PNAS U.S.A. 106: 17910-17915 (2009). Anthracyclines, such as doxorubicin and daunorubicin, bind to DNA and block the binding of HIF-1 and HIF-2 in cultured cells and also block HIF-1-dependent expression of angiogenic growth factors, leading to impaired tumor growth.

In renal cancer, HIF2α has been reported to play a primary role in tumorigenesis. See, Covello, K., et al., Cancer Res. 65: 2277-2286 (2005), Zimmer, M. et al., Mol. Cancer Res. 2: 89-95 (2004). Recent structural work on HIF-2α reports that the crystal structure of the PAS-B domain can contain a large (approximately 290 Å) cavity in its core. However, the amino acid side chains in the solution structure are dynamic. For example, those side chains can tend to intrude more deeply in the core, and can shrink the cavity to 1 or 2 smaller cavities or can even expand the cavity. See Scheuermann, T. H. et al. Artificial ligand binding within the HIF-2α PAS-B domain of the HIF2 transcription factor. *Proc Natl Acad Sci USA* 106, 450-455 (2009), and Key et al., Principles of ligand binding within a completely buried cavity in HIF 2α PAS-B, *J. Am. Chem. Soc.,* 2009, 131 (48): 17647-17654. doi: 10.1021/ja9073062. A recent study reported that two compounds identified from ten sponge extracts appeared to be selective HIF2α inhibitors in selected cell lines. See McKee, T. C., et al. J. Natural Products (2012). Heretofore, pharmacological dogma has held that small molecules are unlikely to disrupt large dimerization interfaces such as the combined HLH-PAS-B domains of HIF2α and HIF1β.

SUMMARY

The present disclosure relates to such disruption by certain small molecules that bind to the HIF-2α PAS-B domain cavity and inhibit heterodimerization of HIF-2α to HIF1β (ARNT).

The inventors have discovered certain compounds and/or pharmaceutical salts thereof for inhibiting heterodimerization of HIF-2α to HIF1β (ARNT) by binding such compounds and/or salts to the HIF-2α PAS-B domain cavity (such compounds and/or salts are defined herein as "certain small molecules that bind to the HIF-2α PAS-B domain cavity and inhibit heterodimerization of HIF-2α to HIF1β (ARNT) but do not bind to HIF1α and do not inhibit heterodimerization of HIF1α to HIF1β (ARNT)"). The present disclosure reveals that the HIF-2α PAS-B domain cavity is a target to which such certain small molecules can bind and result in inhibition of HIF-2α heterodimerization to HIF1β (ARNT).

In one embodiment, the disclosure provides a method comprising binding a compound of formula (I)

B1-L-B2 (I)

and/or a pharmaceutically acceptable salt thereof, to a HIF-2α PAS-B domain cavity but not binding to HIF1α, resulting in inhibition of heterodimerization of HIF-2α to HIF1β (ARNT) but not resulting in inhibition of heterodimerization of HIF1α to HIF1β (ARNT), wherein in said compound and/or said pharmaceutically acceptable salt thereof B1 and B2 are independently chosen from cycloalkyl, heterocycloalkyl, aryl, and heteroaryl, L is chosen from a bond, (CH2)mO(CH$_2$)n, alkylene, (CH2)mS(CH$_2$)n, (CH2)m NR'(CH$_2$)n, C(O)NR'', SO$_2$, SO$_2$NR''', SO, (CH$_2$)mC(O)(CH$_2$)n, cycloalkylene, heterocycloalkylene, arylene, and heteroarylene;

R', R'' and R''' are independently selected from H and alkyl;

each of the cycloalkyl, cycloalkylene, alkylene, heterocycloalkyl, heterocycloalkylene, aryl, arylene, heteroaryl, and heteroarylene is, independently from one another, optionally substituted with at least one substituent selected from alkyl, alkenyl, alkynyl, carboxyl, sulfonyl hydroxide, halo, oxo, NO$_2$, NR$^1$R$^2$, CN, ureido, OR$^3$, alkylsulfonyl, aminosulfonyl, alkylcarbonyl, alkoxycarbonyl, aminocarbonyl, alkylsulfinyl, alkylsulfonimidoyl, cycloalkyl, heterocycloalkyl, aryl, and heteroaryl, with each of the substituents alkyl, alkenyl, alkynyl, alkoxy, alkylsulfonyl, alkylcarbonyl, alkoxycarbonyl, alkylsulfinyl, alkylsulfonimidoyl, cycloalkyl, heterocycloalkyl, aryl, and heteroaryl being, independent from one another, further optionally substituted with at least one group A, with each of the substituents ureido, aminosulfonyl, and aminocarbonyl being, independently from one another, further optionally substituted with at least one group B;

R$^1$, R$^2$, and R$^3$ are independently selected from H, alkyl, alkylcarbonyl, and alkylsulfonyl, with each of the alkyl, alkylcarbonyl, and alkylsulfonyl being, independently from one another, optionally substituted with at least one group A;

A is selected from alkoxy, halo, hydroxyl, CN, NO$_2$, alkylcarbonyl, alkoxycarbonyl, aureido, aminosulfonyl, aminocarbonyl, and carboxyl;

B is selected from alkyl and aryl, with each of the alkyl and aryl being, independently from one another, optionally substituted with at least one group A;

each of the above m and n is independently selected from 0, 1, 2, 3, 4, and 5, provided that the compound is not N-(2-nitro-4-(trifluoromethyl)phenyl)morpholin-4-amine.

As used herein, the terms "a compound of formula (I)

B1-L-B2 (I)

and/or a pharmaceutically acceptable salt thereof," fall within the scope of the term "certain small molecules that bind to the HIF-2α PAS-B domain cavity and inhibit heterodimerization of HIF-2α to HIF1β (ARNT) but do not bind to HIF1α and do not inhibit heterodimerization of HIF1α to HIF1β (ARNT)," as long as such binding and inhibition occur.

In another embodiment, the disclosure provides a method of binding a compound

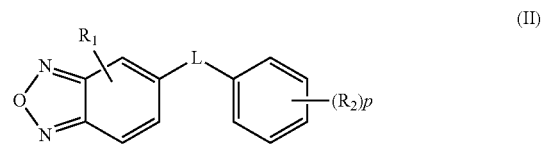

and/or a pharmaceutically acceptable salt thereof, to a HIF-2α PAS-B domain cavity, resulting in inhibition of heterodimerization of HIF-2α to ARNT, wherein L is selected from NH and NH(CH$_2$), R$_1$ is a NO$_2$ and R$_2$ is independently selected from NO$_2$, halo, and alkyl optionally substituted with at least one group selected from halo, and p is 1, 2, 3, 4, or 5.

As used herein, the terms "

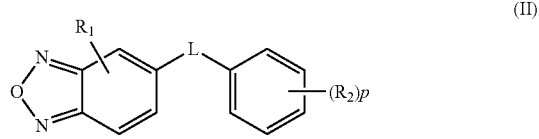

(II)

and/or a pharmaceutically acceptable salt thereof" also fall within the scope of the term "certain small molecules that bind to the HIF-2α PAS-B domain cavity and inhibit heterodimerization of HIF-2α to HIF1β (ARNT) but do not bind to HIF1α and do not inhibit heterodimerization of HIF1α to HIF1β (ARNT)," as long as such binding and inhibition occur.

In one embodiment, the disclosure provides a method of inhibiting heterodimerization of HIF-2α to HIF1β (ARNT) but not inhibiting heterodimerization of HIF1α to HIF1β (ARNT) comprising binding to a HIF-2α PAS-B domain cavity but not binding to HIF1α with a means for said inhibiting.

In yet another embodiment, the disclosure provides a method comprising inhibiting heterodimerization of HIF-2α to HIF1β (ARNT) but not inhibiting heterodimerization of HIF1α to HIF1β (ARNT) with a compound that binds to a HIF-2αPAS-B domain cavity but does not bind to HIF1α, provided that the compound is not N-(2-nitro-4-(trifluoromethyl)phenyl)morpholin-4-amine; 1-nitro-4-phenoxybenzene, N-benzyl-2-nitro-4-(trifluoromethyl)aniline, N-(cyclopropylmethyl)-2-nitro-4-(trifluoromethyl)aniline, 2-nitro-N-(thiophen-3-ylmethyl)-4-(trifluoromethyl)aniline, N-(furan-2-ylmethyl)-2-nitro-4-(trifluoromethyl)aniline, or N-(2-nitro-4-(trifluoromethyl)phenyl)morpholin-4-amine.

BRIEF DESCRIPTION OF FIGURES

The following figures form part of the present specification and are included to further demonstrate certain aspects of the present invention. The invention may be better understood by reference to one or more of these drawings in combination with the detailed description of specific embodiments presented herein.

FIG. 8A-D shows an AlphaScreen assay format that can identify antagonists of protein-protein interactions between HIF-2α PAS-B* and ARNT PAS-B*. (FIG. 8a) As shown in the cartoon schematic, interactions between GST-tagged HIF-2α (green) and FLAG-tagged ARNT (blue) PAS-B* domains recruit both donor beads (D), coated with glutathione, and acceptor beads (A), coated with anti-FLAG antibodies, to one another. Upon illumination with red (680 nm) light, donor beads will generate short-lived singlet oxygen ($^1O_2$). Nearby (<200 nm) acceptor beads can react with $^1O_2$ to emit light at shorter wavelengths (top). Compounds that disrupt the complex correspondingly eliminate this signal (bottom). Compounds that non-specifically interfere with the AlphaScreen assay can be identified with a counterscreen in which the ARNT PAS-B* domain was simultaneously tagged with both the GST and FLAG tags. (FIG. 8b) The AlphaScreen signal (relative units; RU) reflecting protein-protein interactions between 25 (open triangles), 50 (open circles) or 100 (closed circles) nM HIF-2α PAS-B* increases with increasing concentrations of ARNT PAS-B*. At the highest ARNT PAS-B* concentrations, a decrease in signal reflects the hook effect. At these concentrations, protein binding to the acceptor beads has become saturated and free ARNT PAS-B* competes with the coated acceptor beads for the donor beads bound to HIF-2α PAS-B*. (FIG. 8c) HIF-2α PAS-B*-ARNT PAS-B* protein-protein interactions can be effectively competed by addition of untagged ARNT PAS-B* but not by untagged wildtype (wt) ARNT PAS-B, which has a substantially lower affinity for HIF-2α PASB*. (FIG. 8d) Neither untagged protein effectively reduces signal from AlphaScreen assays employing the doubly-tagged GST-ARNT PAS-B*-FLAG control protein. Assays were performed in triplicate and the error bars represent±SD.

FIG. 9A-D shows a small molecule antagonist, one of the certain small molecules disclosed herein, of the HIF-2α/ARNT PAS-B* heterodimer identified using AlphaScreen. (FIG. 9a) Structure of compound (32). (FIG. 9b) Compound (32) antagonizes HIF-2α/ARNT PAS-B* heterodimerization (squares) in dose-dependent manner in the AlphaScreen assay. No effect was observed in control reactions employing a single (doubly tagged) GST-ARNT-PAS-B*-FLAG protein capable of recruiting both beads to induce an AlphaScreen signal (triangles). Assays were performed in triplicate and the error bars represent±SD. RU=relative units. (FIG. 9c)$^{15}$N/$^1$H HSQC spectra of 200 μM $^{15}$N HIF-2α PAS-B or $^{15}$N-ARNT PAS-B (inset) in the presence of increasing concentrations of compound (1) (0, 125, or 250 μM represented by a red to blue gradient) demonstrate binding specificity for the HIF-2α PAS-B domain. (FIG. 9d) ITC measurements demonstrate that compound (1) binds to the HIF-2α PAS-B domain with a KD=1100 nM with a 1:1 stoichiometry. Note that these ITC measurements were conducted in the presence of 5% DMSO, slightly weakening the apparent affinity of the protein/ligand interaction.

(FIG. 10a) Wall-eyed stereoview of representative 2mFo-DFc electron density from HIF-2α PAS-B*/compound (1) complex. Density is rendered at 2σ (grey) and 5σ (dark blue). (FIG. 10b) Evidence for fractional ligand occupancy in the HIF-2α PAS-B* binding site. At a low contour (=1σ 2mFo-DFc) two conformations of the M252 sidechain are evident (grey/red/blue/yellow sticks=ligand-bound conformation; black sticks=ligand-free state, as established by RCSB ID: 3F1P$^3$). Additionally, a weak density peak adjacent (black sphere) to the liganded M252 conformation likely corresponds to water bound in the apo-protein (water #10 in 3F1P).

(FIG. 11a) Overview of HIF-2α PAS-B/compound (1) complex. A portion of the HIF-2α surface (purple) has been cut away to reveal the internal binding site of the small molecule ligand (dark grey). The structures in (a) and (b) were determined of a HIF-2α/ARNT PAS-B* heterodimer, but the ARNT subunit has been omitted for clarity. (FIG. 11b) Overview of the HIF-2α PAS-B/THS-044 complex. (FIG. 11c) Expanded views of ligand placement within HIF-2α PAS-B, as seen for compound (1) (dark grey) and three previously-reported structures with NMR/fragment derived compounds: THS-0443, THS-0174, and THS-0204 (all light grey for carbons, standard CPK colors for others). Selected secondary structure elements are labeled using standard nomenclature. The surface of the apo-protein internal cavity is rendered in light grey, showing some of the required protein conformational changes to accommodate ligand binding and the superior shape complementation of compound (1) compared to the fragment-derived compounds. (FIG. 11d) Wireframe structures of compounds shown above.

(FIG. 14a) The crystal structure of the ternary complex of HIF-2 PAS-B* with compound (1) (inset, top) reveals ligand binding into the internal cavity sequestered from bulk solvent within the HIF-2α PAS-B domain (grey). For clarity, the ARNT-PAS-B* portion of the protein heterodimer is not shown, and a portion of the HIF-2α PAS-B* surface (blue) has been cut away to reveal the internal binding site. (FIG. 14b) Protein/ligand contacts as revealed by expanded view of the compound (1) binding site, showing that it is composed of a mix of polar and hydrophobic residues. (FIG. 14c) $^{15}$N/$^1$H HSQC spectra of 200 μM $^{15}$N HIF-2α PAS-B (main panel) and $^{15}$N-ARNT PAS-B (inset) in the presence of 0, 125, and 250 μM Compound (1) (red to blue) demonstrate the specific binding of Compound (1) to HIF-2α PAS-B. One-dimensional traces of spectra (at locations shown by dashed lines) demonstrate slow exchange binding behavior of Compound (1) to HIF-2α, and no binding to ARNT PAS-B. (FIG. 14d) ITC measurements of Compound (1) to HIF-2α PAS-B quantitate the binding affinity and 1:1 stoichiometry.

FIG. 15A-D shows that the binding of Compound (1) into HIF-2α PAS-B affects the heterodimeric β-sheet interface between HIF PAS domains. (FIG. 15a) Backbone $^1$H and $^{15}$N chemical shift differences between apo and Compound (1)-bound states are mapped onto the HIF-2α PAS-B primary and secondary structures. The yellow-to-red color scale shown on the right is used in (FIG. 15b) and (FIG. 15d). (FIG. 15b) Ligand-induced chemical shift perturbations are mapped onto the HIF-2α PAS-B structure with spheres denoting HIF-2α Cα sites within 8 Å of ARNT PAS-B. View is approximately 180° rotated about the y (vertical) axis from the view in FIG. 15a. (FIG. 15c) Ligand-induced conformational changes in similar regions are also evident from X-ray diffraction data, as revealed by a Fo(liganded)-Fo(apo) electron density difference map (rendered at 4σ; positive density in green, negative density in red). (FIG. 15d) Colocalization of the β-sheet conformational effects and the protein heterodimer interface are shown in two views of the heterodimer (PDB code: 3F1P18). ARNT PAS-B is rendered as a blue cartoon with a transparent surface.

FIG. 16A-B shows that Compound (1) disrupts HIF-2 heterodimerization in vitro. (FIG. 16a) Addition of Compound (1) blocks heterodimer assembly between purified recombinant HIF-2α PAS-B* and ARNT PASB* heterodimer (close circled) as assessed in the AlphaScreen Assay. No effect was observed in control reactions employing a single (doubly-tagged) GST-ARNT-PAS-B*-FLAG protein capable of recruiting both beads to induce an AlphaScreen signal (open circles). Assays were performed in triplicate and the error bars represent±SD. RU=relative units. (FIG. 16b) Compound (1) disrupts heterodimerization of the full length HIF-2 transcription factor. Nuclear extracts prepared from hypoxic Hep3B cells expressing ARNT, HIF-1α, and HIF-2α (input) were incubated with increasing concentrations of (1). Immunoblot analysis indicates amounts of HIF polypeptides immunoprecipitated in the absence (–Ab) or presence of an anti-ARNT antibody.

(FIG. 17a) Comparison of internal cavity sizes (blue) identified by a 1.4 Å probe within the HIF-2α PAS-B crystal structure (PDB code 3F1P)18 (top) and a homology model of HIF-1α PAS-B domain based on this structure. Sequence differences amongst these two closely-related paralogs reduce the expected size of the HIF-1α PAS-B cavity. (FIG. 17b) The HIF-1α PAS-B model suggests that several sequence differences among these paralogs leads to the placement of bulkier sidechains (red) within the HIF-1α PAS-B core. These substitutions appear to shrink the cavity observed in HIF-2α PAS-B (HIF-2αPAS-B cavity rendered as a blue surface, superimposed on the HIF-1α PASB model). Amino acid differences are indicated with the first one-letter code designating HIF-2 amino acid identity, and HIF-1 identity by the last letter. (FIG. 17c) ITC measurements of a HIF-1α PAS-B/compound (1) titration does not show detectable protein-ligand interaction under the same conditions used to observe binding with HIF-2α PAS-B.

FIG. 18A-D shows that Compound (1) selectively antagonizes HIF2 activity in cultured cells. Incubation of Compound (1) with normoxic 786-0 cells has no effect on HIF-2α expression as measured by (FIG. 18a) RT-PCR or (FIG. 18b) immunoblot analysis. RT-PCR reveals that expression of HIF-2 target genes are antagonized by Compound (1) in both 786-0 (FIG. 18a) and Hep3B (FIG. 18c) cells. (FIG. 18d) Compound (1) selectively disrupts DNA-binding by HIF-2, but not HIF-1, in a ChIP assay. Differences between paired values are statistically significant as determined by t-test. *=p<0.01; **=p<0.001.

FIG. 19A-B shows that Compound (1) and Compund (47) reduce VEGF protein secretion in a dose-dependent manner. VEGF protein secretion was measured by ELISA following incubation of cultured 786-O cells for about eighteen (18) hours with Compund (1) (FIG. 19a) or with Compound (47) (FIG. 19b). Total secreted VEGF protein was plotted as pg/mL 1×10$^4$ seeded cells verses the logarithmic concentration of coumpound at final concentrations of 0.00655, 0.01638, 0.04096, 0.1024, 0.256, 1.6, 4, 10, and 20μM.

DETAILED DESCRIPTION

Figure 1:
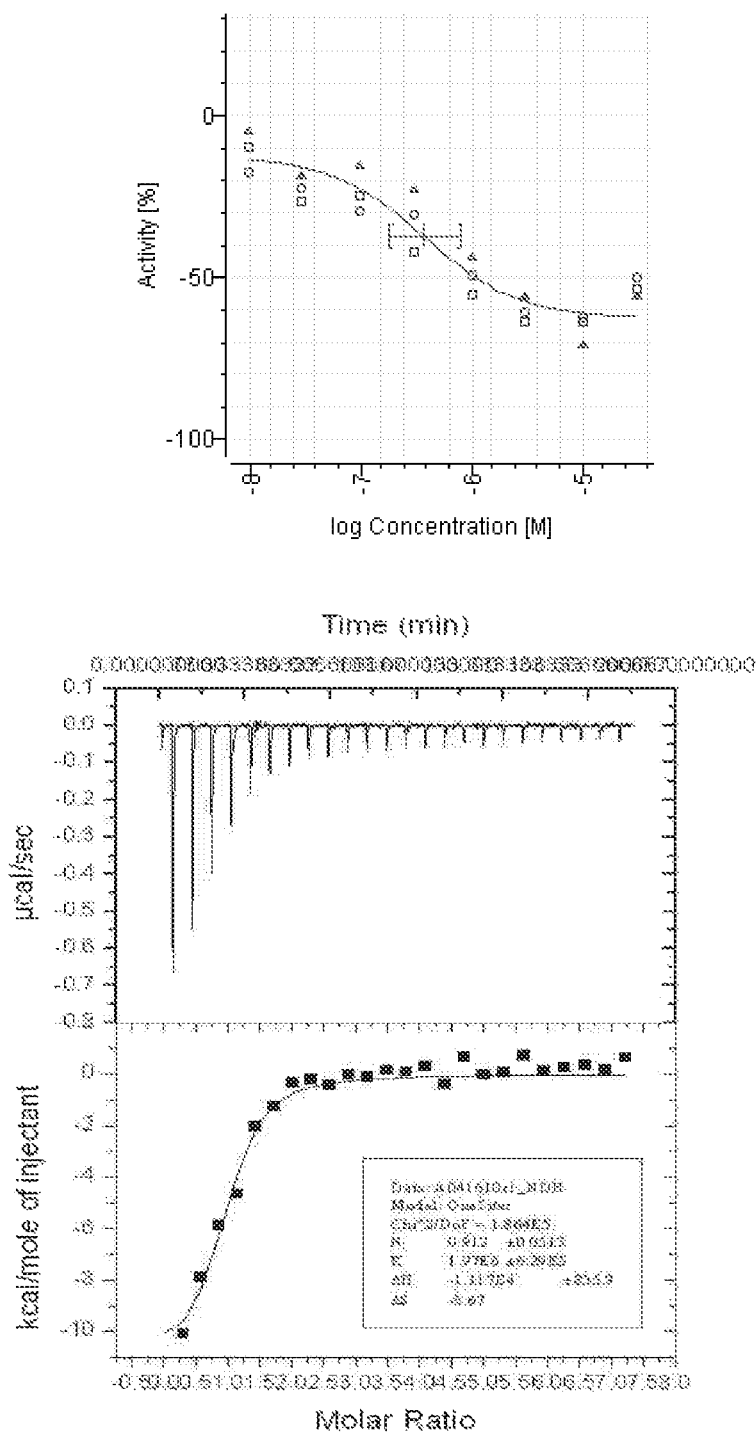
FIG. 1 shows the AlphaScreen Data curve for compound 2, one of the certain small molecules disclosed herein.
Figure 2:
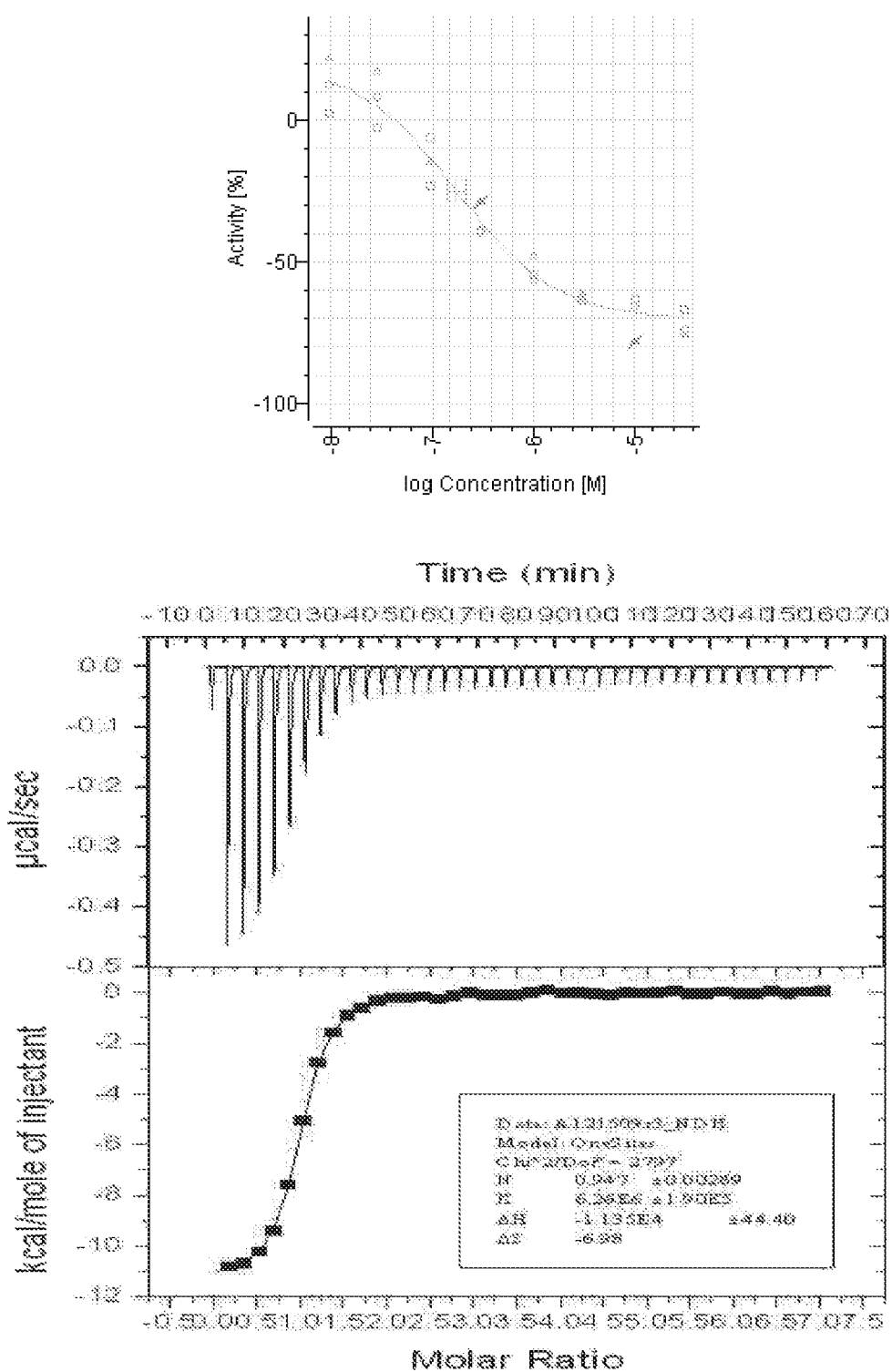
FIG. 2 shows the AlphaScreen Data curve for compound 5, one of the certain small molecules disclosed herein.
Figure 3:
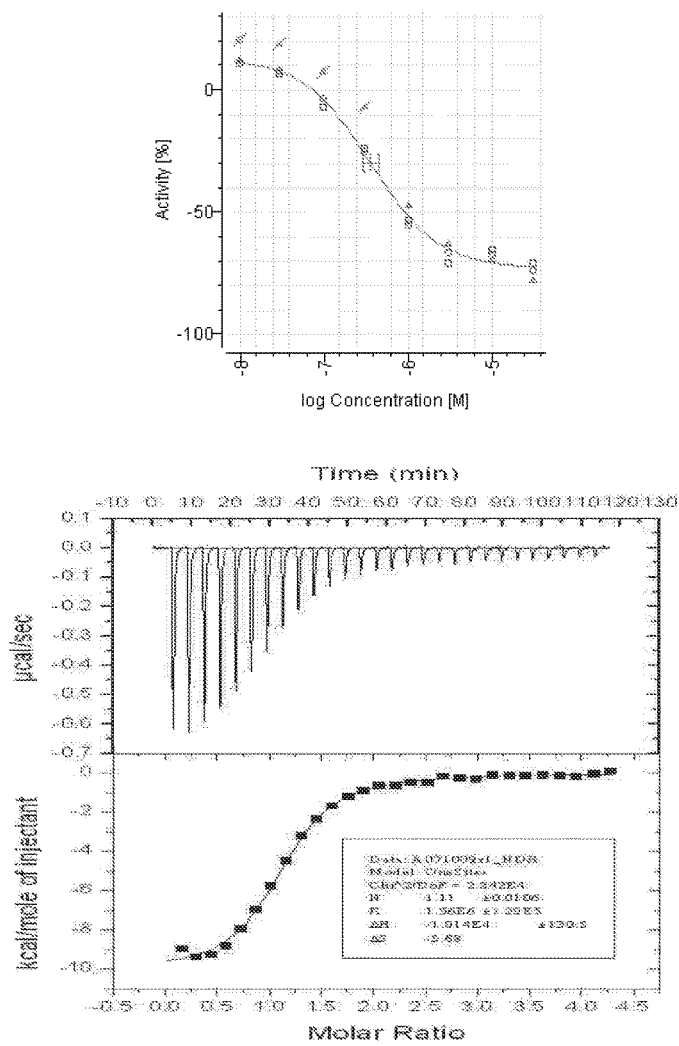
FIG. 3 shows the AlphaScreen Data curve for compound 6, one of the certain small molecules disclosed herein.
Figure 4:
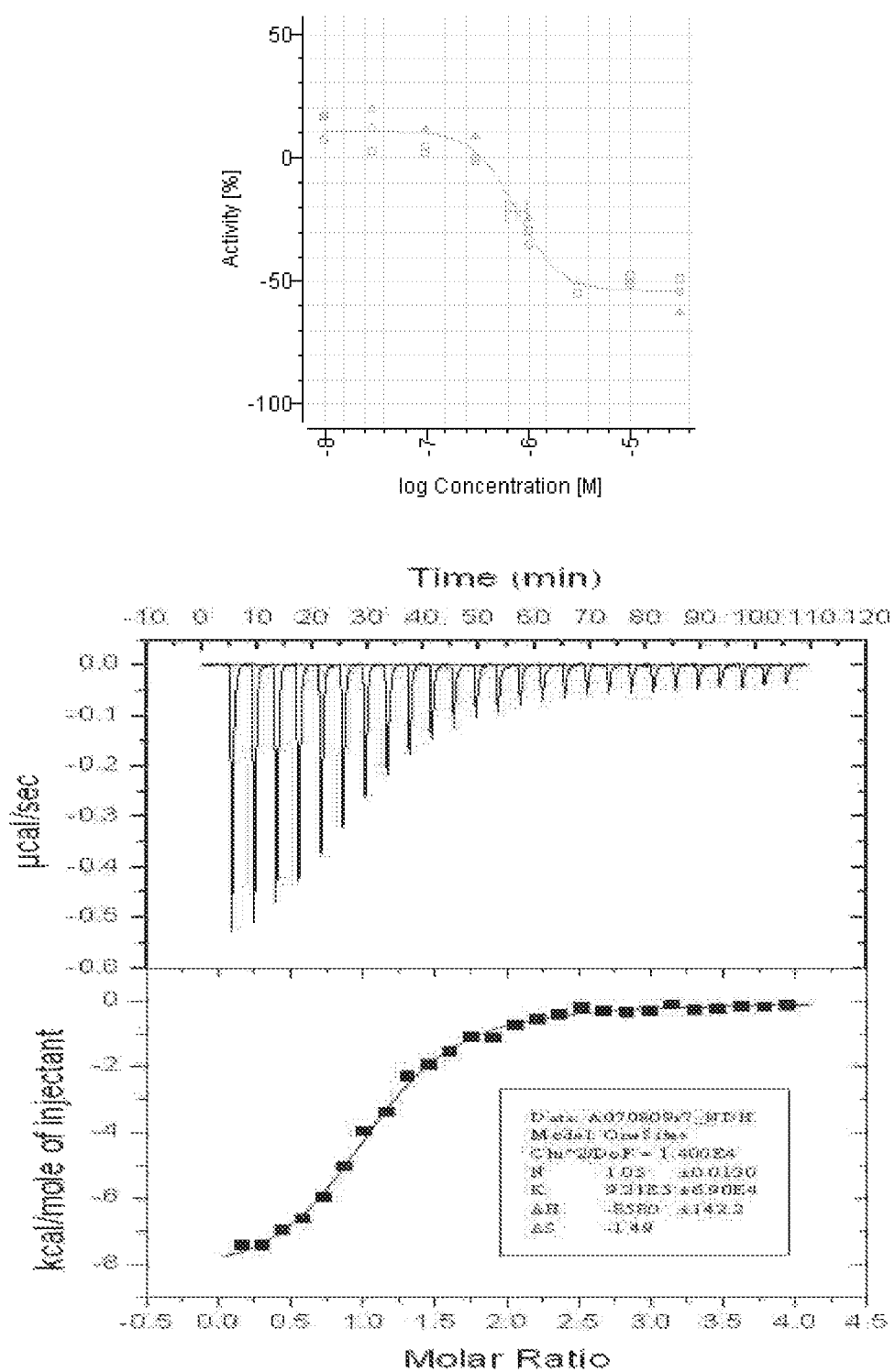
FIG. 4 shows the AlphaScreen Data curve for compound 8, one of the certain small molecules disclosed herein.

For purposes of interpreting this disclosure, the following definitions will apply.

The term "HIF2α" refers to a monomeric protein that contains three conserved structured domains: basic helix-loop-helix (bHLH), and two Per-ARNT-Sim (PAS) domains designated PAS-A and PAS-B, in addition to C-terminal regulatory regions. "HIF2α" is also alternatively known by several other names in the scientific literature, most commonly EPAS1 and MOP2. As a member of the bHLH/PAS family of transcription factors, "HIF2α" forms an active heterodimeric transcription factor complex by binding to the ARNT (also known as HIF1β) protein through non-covalent interactions.

The term "HIF-2α PAS-B domain cavity" refers to an internal cavity within the PAS-B domain of HIF2α. The crystal structure of the PAS-B domain can contain a large (approximately 290 Å) cavity in its core. However, the amino acid side chains in the solution structure are dynamic: For example, those side chains can tend to intrude more deeply in the core, and can shrink the cavity to 1 or 2 smaller cavities or can even expand the cavity. The cavity is lined by amino acid residues comprising PHE-244, SER-246, HIS-248, MET-252, PHE-254, ALA-277, PHE-280, TYR-281, MET-289, SER-292, HIS-293, LEU-296, VAL-302, VAL-303, SER-304, TYR-307, MET-309, LEU-319, THR-321, GLN-322, GLY-323, ILE-337, CYS-339, and ASN-341 of HIF-2α PAS-B domain. The numbering system is from the known structures reported in the RCSB Protein Data Bank with PDB code 3H7W. As one of skill in the art would know, other numbering systems in the PDB could define the same amino acids, expressed above, that line the cavity.

The terms "HIF2-HDI" or "HIF2α heterodimerization inhibitor" may be used interchangeably and as used herein refer to certain small molecules that bind to the HIF-2α PAS-B domain cavity and inhibit heterodimerization of HIF2α to HIF1β (ARNT) but do not bind to HIF1α and do not inhibit heterodimerization of HIF1α to HIF1β (ARNT). In other words, both terms HIF2-HDI and HIF2α heterodimerization inhibitor are synonymous with the term "certain small molecules that bind to the HIF-2α PAS-B domain cavity and inhibit heterodimerization of HIF-2α to HIF1β (ARNT) but do not bind to HIF1α and do not inhibit heterodimerization of HIF1α to HIF1β (ARNT)." All three terms can be used interchangeably. And, for the sake of simplicity, the term "certain small molecules that bind to the HIF-2α PAS-B domain cavity and inhibit heterodimerization of HIF-2α to HIF1β (ARNT) but do not bind to HIF1α and do not inhibit heterodimerization of HIF1α to HIF1β (ARNT)" can be interchangeably shortened to "certain small molecules."

The term "binding," as used herein, refers to the binding between the HIF2-HDI and the HIF-2α PAS-B domain cavity wherein the certain small molecule binds to the HIF-2α PAS-B domain cavity with sufficient affinity such that the HIF2-HDI inhibits heterodimerization of HIF-2α to HIF-1β (ARNT). In some embodiments the binding involves formation of at least one covalent bond. In some embodiments, the binding occurs through at least one non-covalent force, such as, Van der Waals, hydrogen bond, and electrostatic interaction. In some embodiments, the binding is determined by co-crystallography. Various means may be used to identify whether the certain small molecule binds to the HIF-2α PAS-B domain cavity, for example, isothermal titration calorimetry (ITC), $^{15}$N/$^1$H HSQC NMR spectroscopy, or by co-crystallography. ITC measures binding affinity and the magnitude of thermodynamic components of binding affinity—enthalpy and entropy changes. See Leavitt et al. Direct measurement of protein binding energetic by isothermal titration calorimetry, *Current Opinion in Structural Biology* 2001, 11:560-566, and Lewis et. al. (2007). "Isothermal Titration calorimetry: Experimental Design, Data Analysis, and Probing Macromolecule/Ligand Binding and Kinetic Interactions" *Biophysical Tools for Biologists*, Volume 1, Chapter 4. 2007, Academic Press, Edited by John Correia and H. Detrich.

ITC, as described more fully below, introduces a wild-type HIF-2α PAS-B solution into a to-be-assayed compound solution using, for example, a VP-ITC instrument (Micro-Cal). After subtracting heats of dilution evolved from the titrating protein, e.g., wild-type HIF-2α PAS-B, into a compound-free buffer, data were fit to a single-site binding model with, for example, MicroCal Origin® software to determine complex affinities.

Certain small molecules as defined herein bind to a HIF2α PAS-B cavity with a Kd value not exceeding 30 μM, for example, ranging from 10 to 30 μM, further, for example, ranging from 1 to 10 μM, and even further, for example, less than 1 μM, as determined by ITC. In some embodiments, the certain small molecules bind to a HIF2αPAS-B cavity with a Kd value not exceeding 1 μM as determined by ITC.

The binding of the certain small molecules to the HIF-2α PAS-B domain cavity may also be determined by $^{15}$N/$^1$H HSQC NMR spectroscopy. NMR-based methods have been described in the literature See Erlanson, "Fragment-based lead discovery: a chemical update." *Current Opinion in Biotechnology* 17(6): 643-652, 2006, Meyer, et al., "NMR Spectroscopy techniques for screening and identifying ligand binding to protein receptors." *Angewandte Chemie-International Edition* 42(8): 864-890, 2003, Coles, et al., "NMR-based screening technologies." *Drug Discovery Today* 8(17): 803-810, 2003, Dalvit, et al., "Identification of compounds with binding affinity to proteins via magnetization transfer from bulk water." Journal *of Biomolecular NMR* 18(1): 65-68, 2000, Mayer, et al., "Characterization of ligand binding by saturation transfer difference NMR spectroscopy." *Angewandte Chemie-International Edition* 38(12): 1784-1788, 1999, Hajduk, et al., "One dimensional relaxation- and diffusion-edited NMR methods for screening compounds that bind to macromolecules." *Journal of the American Chemical Society* 119(50): 12257-12261, 1997, and Shuker et al., Discovering High-Affinity Ligands for Proteins: SAR by NMR, *Science*, vol. 274, pp 1531-1534, Nov. 29, 1996.

For example, $^{15}$N/$^1$H HSQC NMR spectroscopy can be performed on a solution of the to-be-assayed certain small molecule and a HIF-2α PAS-B domain in a solvent. Ligand dissociation and association rates are extracted from a simultaneous fit of the cross peak and autopeak intensities to the McConnell Equations. See Key et al., Principles of ligand binding within a completely buried cavity in HIF 2α PAS-B, *J. Am. Chem. Soc.,* 2009 Dec. 9; 131 (48): 17647. doi: 10.1021/ja9073062. In some embodiments, changes in peak intensity or locations in $^{15}$N/$^1$H HSQC spectra indicate ligand binding.

Using another method, the binding of a certain small molecule to HIF-2α PAS-B domain cavity may be determined by co-crystallography. See Cooper, et al., X-ray crystallography: Assessment and validation of protein-small molecule complexes for drug discovery, *Expert Opin Drug Discov.,* 2011 Aug. 1; 6(8): 771-782. doi:10.1517/17460441.2011.585154.

The binding of the certain small molecules to the HIF-2α PAS-B domain cavity may be determined by ITC, NMR, and/or co-crystallography. In other words, a determination of binding by any of ITC, NMR, and/or co-crystallography is considered binding within the scope of this disclosure even if one or both of the other methods does not result in a determination of binding. In some embodiments, the certain small molecule binds to HIF-2α PAS-B domain cavity through at least four or more amino acids selected from PHE-244, SER-246, HIS-248, MET-252, PHE-254, ALA-277, PHE-280, TYR-281, MET-289, SER-292, HIS-293, LEU-296, VAL-302, VAL-303, SER-304, TYR-307, MET-309, LEU-319, THR-321, GLN-322, GLY-323, ILE-337, CYS-339, and ASN-341 of HIF-2α PAS-B domain. The numbering system is from the known structures reported in the RCSB Protein Data Bank with PDB code 3H7W. In some embodiments, as noted, the binding occurs through at least one covalent bond and in other embodiments the binding occurs through a non-covalent force, such as, Van der Waals, hydrogen bond, and electrostatic interaction. In some embodiments, the binding is determined by co-crystallography. There are some of the certain small molecules that exhibit both covalent and non-covalent binding.

The term "heterodimerization" as used herein refers to the complex formed by the non-covalent binding of HIF2α to HIF1β (ARNT). Heterodimerization of HIF2α to HIF1β (ARNT) is required for HIF2α DNA binding and transcriptional activity and is mediated by the HLH and PAS-B domains. Transcriptional activity following heterodimerization of HIF2α to HIF1β (ARNT) can affect four groups of target genes relevant to cancer including angiogenic factors, glucose transporters and glycolytic enzymes, survival factors, and invasion factors.

The term "inhibition of heterodimerization" refers to inhibition of formation of the HIF2α-HIF1 (ARNT) complex resulting from the binding of a HIF2-HDI to the HIF-2αPAS-B domain cavity while HIF1α-HIF1β (ARNT) heterodimerization remains unaffected.

Inhibition of heterodimerization of HIF-2α to HIF1β (ARNT) may be determined in an Amplified Luminescent Proximity Homogeneous Assay (AlphaScreen). AlphaScreen, an in vitro assay, employs "PAS-B*" variants (R247E HIF-2α and E362R ARNT; Scheuermann et al., PNAS 2009) to assess functional disruption of PAS-PAS interactions in a high throughput screening (HTS) format.

In some embodiments, the certain small molecule inhibits heterodimerization of HIF-2α to HIF1β (ARNT) with an $IC_{50}$ value not exceeding 30 µM, for example, ranging from 10 to 30 µM, and further, for example, ranging from 1 to 30 µM, as determined by AlphaScreen. In some embodiments, the certain small molecule has an $IC_{50}$ value not exceeding 1 µM as determined by AlphaScreen.

Inhibition of heterodimerization of HIF-2α to HIF1β (ARNT) may also be determined by a reduction in HIF-2α target gene mRNA expression. mRNA quantitation can be obtained through real-time PCR technology. See Wong, et al., Real-time PCR for mRNA quantitation, *Bio Techniques* 39, No. 1, pp. 1-11 Jul. 2005. Yet another method for determining whether the HIF2-HDI and/or a pharmaceutically acceptable salt thereof inhibits heterodimerization of HIF-2α to HIF1β (ARNT) is by co-immunoprecipitation.

Co-immunoprecipitation is a classic method of detecting protein-protein interactions and is well known to one of ordinary skill in the art. See Phizicky, et al., Protein-Protein Interactions: Methods for Detection and Analysis, *Microbiological Reviews*, Vol. 59, No. 1, pp. 94-123, March 1995.

Inhibition of heterodimerization of HIF-2α to HIF1β (ARNT) may be determined by any one or more of the methods—AlphaScreen, a reduction in HIF2α target gene mRNA expression, and/or co-immunoprecipitation. In other words, a determination of inhibition by any of AlphaScreen, a reduction in HIF2α target gene mRNA expression, and/or co-immunoprecipitation is considered to be inhibition within the scope of this disclosure even if one or both of the other methods does not result in a determination of inhibition The term "alkyl" herein refers to a straight or branched hydrocarbon group, containing 1-18, such as 1-12, further such as 1-6 carbon atoms. Examples of alkyl groups include, but are not limited to, methyl, ethyl, n-propyl, i-propyl, n-butyl, i-butyl, t-butyl, and the like.

The term "alkoxy" herein refers to a straight or branched alkyl group of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like.

The term "alkenyl" herein refers to a straight or branched hydrocarbon group, containing one or more C=C double bonds and 2-10 carbon atoms, such as 2-6 carbon atoms. Examples of alkenyl groups include, but are not limited to, vinyl, 2-propenyl, 2-butenyl, and the like.

The term "alkynyl" herein refers to a straight or branched hydrocarbon group, containing one or more C≡C triple bonds and 2-10 carbon atoms, such as 2-6 carbon atoms. Examples of alkynyl groups include, but are not limited to, ethynyl, 2-propynyl, 2-butynyl, and the like.

The term "cycloalkyl" refers to saturated and partially unsaturated cyclic hydrocarbon groups having 3 to 14, such as 3 to 8 carbon atoms. Examples of cycloalkyl groups include, but are not limited to, cyclopropyl, cyclobutyl, cyclopentyl, cyclopentenyl, cyclohexyl, cyclohexenyl, cycloheptyl, cyclooctyl, and the like. The ring may be saturated or have one or more double bonds (i.e., partially unsaturated), but not fully conjugated, and not aromatic, as defined herein. The definition also covers fused bicyclic or tricyclic ring systems wherein none of the rings is aromatic.

The term "cycloalkylene" refers to the same ring groups as defined for "cycloalkyl" except that cycloalkylene is a bivalent radical, e.g., having an additional point of attachment when compared with cycloalykl. For example, a cyclobutyl group has one point of attachment on the ring, while a cyclobutylene group has two points of attachment on the ring.

The term "aryl" encompasses:

5- and 6-membered carbocyclic aromatic rings, for example, phenyl;

fused bicyclic, carbocyclic ring systems wherein at least one ring is aromatic, for example, naphthalene, indane, and 1,2,3,4-tetrahydroquinoline; and fused tricyclic, carbocyclic ring systems wherein at least one ring is aromatic, for example, fluorene.

For example, aryl includes 5- and 6-membered carbocyclic aromatic rings fused to a 5- to 7-membered heterocyclic ring containing one or more heteroatoms selected from N, O, and S. Aryl, however, does not encompass or overlap in any way with heteroaryl, separately defined below. Hence, if one or more carbocyclic aromatic rings are fused with at least one heterocyclic aromatic ring, the resulting ring system is heteroaryl, not aryl, as defined herein.

The term "arylene" refers to the same ring groups as defined for "aryl" except that arylene is a bivalent radical, e.g., having an additional point of attachment on the ring when compared with aryl. For example, a phenyl group has one point of attachment on the ring, while phenylene has two points of attachment on the ring.

The term "halo" refers to fluoro, chloro, bromo, and iodo.

The term "heteroaryl" refers to 5- to 8-membered aromatic, monocyclic rings containing one or more, for example, from 1 to 4, or, in some embodiments, from 1 to 3, heteroatoms selected from N, O, and S, with the remaining ring atoms being carbon;

8- to 12-membered fused bicyclic rings containing at least one aromatic ring, and one or more, for example, from 1 to 4, or, in some embodiments, from 1 to 3, heteroatoms selected from N, O, and S, with the remaining ring atoms being carbon and wherein at least one heteroatom is present in the at least one aromatic ring; and 11- to 14-membered fused tricyclic rings containing at least one aromatic ring, and one or more, for example, from 1 to 4, or in some embodiments, from 1 to 3, heteroatoms selected from N, O, and S, with the remaining ring atoms being carbon and wherein at least one heteroatom is present in the at least one aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of heteroaryl groups include, but are not limited to (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 1-pyrazolyl, 2,3-pyrazolyl, 2,4-imidazolinyl, isoxazolyl, oxazolyl, thiazolyl, thiadiazolyl, tetrazolyl, thienyl, benzothienyl, furyl, benzofuryl, benzoimidazolinyl, benzoxadiazolyl, indolinyl, pyridizinyl, triazolyl, quinolinyl, pyrazolyl, and 5,6,7,8-tetrahydroisoquinoline.

Further heteroaryl groups include but are not limited to pyrrolyl, isothiazolyl, triazinyl, pyrazinyl, pyridazinyl, indolyl, benzotriazolyl, quinoxalinyl, and isoquinolinyl. For example, the heteroaryl groups are selected from 1,3,4-oxadiazol-2-yl, 1,2,4-oxadiazol-3-yl, 1,2,4-oxadiazol-5-yl, 1,2,4-trizazol-3-yl, 1,2,4-triazol-5-yl, 1(H)-tetrazol-5-yl, 2(H)-tetrazol-5-yl, 1,3,4-oxadiazol-2(3H)-oxo-5-yl, 1,2,4-oxadiazol-5(4H)-oxo-3-yl, and 1(H)-1,2,4-tirazol-5(4H)-oxo-3-yl. As with the definition of heterocycle below, "heteroaryl" is also understood to include the N-oxide derivative of any nitrogen-containing heteroaryl. Heteroaryl does not encompass or overlap with aryl as defined above.

The term "heteroarylene" refers to the same ring groups as defined for "heteroaryl" except that heteroarylene is a bivalent radical, e.g., having an additional point of attachment on the ring when compared with heteroaryl. For example, a pyridyl group has one point of attachment on the ring, while a pyridylene group has two points of attachment on the ring.

The term "heterocycloalkyl" refers to a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. The rings may be saturated or have one or more double bonds (i.e. partially unsaturated). The heterocycloalkyl can be substituted by oxo. The point of the attachment may be carbon or heteroatom in the heterocyclic ring, provided that attachment results in the creation of a structure which is deemed acceptable by one of ordinary skill in the art. When the heterocyclic ring has substituents, it is understood that the substituents may be attached to any atom in the ring, whether a heteroatom or a carbon atom, provided that a stable chemical structure results. The term "heterocycloalkyl" also refers to fused bicyclic or tricyclic saturated or partially saturated ring systems containing 1-3 heteroatoms independently selected from oxygen, sulfur, and nitrogen, as well as combinations comprising at least one of the foregoing heteroatoms, wherein none of the rings is aromatic. Heterocycle does not overlap with heteroaryl.

Suitable heterocycles include, for example (as numbered from the linkage position assigned priority 1), 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, and 2,5-piperazinyl. Morpholinyl groups are also contemplated, including 2-morpholinyl and 3-morpholinyl (numbered wherein the oxygen is assigned priority 1). Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

The term "heterocycloalkylene" refers to the same ring groups as defined for "heterocycloalkyl" except that heterocycloalkylene Is a bivalent radical, e.g., having an additional point of attachment on the ring when compared with heterocycloalkyl. For example, a pyrrolidinyl group has one point of attachment on the ring, while a pyrrolidinylene group has two points of attachment on the ring.

The term "optional" or "optionally" means that the subsequently described event or circumstance may or may not occur, and includes instances where the event or circumstance occurs and instances in which it does not. For example, "alkyl optionally substituted with" encompasses both "alkyl" and "alkyl" substituted with groups as defined herein. It will be understood by those skilled in the art, with respect to any group containing one or more substituents, that such groups are not intended to introduce any substitution or substitution patterns which would be deemed unacceptable by one of ordinary skill in the art.

Certain small molecules described herein include, but are not limited to, when possible, their optical isomers, such as enantiomers and diastereomers, mixtures of enantiomers, including racemates, mixtures of diastereomers, and other mixtures thereof, to the extent they can be made by one of ordinary skill in the art by routine experimentation. In those situations, the single enantiomers or diastereomers, i.e., optically active forms, can be obtained by asymmetric synthesis or by resolution of the racemates or mixtures of diastereomers. Resolution of the racemates or mixtures of diastereomers, if possible, can be accomplished, for example, by conventional methods such as crystallization in the presence of a resolving agent, or chromatography, using, for example a chiral high-pressure liquid chromatography (HPLC) column. In addition, such certain small molecules include Z- and E-forms (or cis- and trans-forms) of certain small molecules with carbon-carbon double bonds. Where certain small molecules described herein exist in various tautomeric forms, the term "certain small molecule" is intended to include, to the extent they can be made without undue experimentation, all tautomeric forms of the certain small molecule.

The term "pharmaceutically acceptable salts," within the scope of the term "certain small molecules," refers to salts prepared from pharmaceutically acceptable non-toxic bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium, and zinc salts. Further, for example, the pharmaceutically acceptable salts derived from inorganic bases may be selected from ammonium, calcium, magnesium, potassium, and sodium salts. Salts derived from pharmaceutically acceptable organic non-toxic bases may be selected, for example, from salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, and tripropylamine, tromethamine.

When the certain small molecule disclosed herein is basic, salts may be prepared using at least one pharmaceutically acceptable non-toxic acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. In some embodiments, such acid may be selected, for example, from citric, hydrobromic, hydrochloric, maleic, phosphoric, sulfuric, fumaric, and tartaric acids.

Provided is a method comprising binding a compound of formula (I)

$$B1-L-B2 \qquad (I)$$

and/or a pharmaceutically acceptable salt thereof, to a HIF-2α PAS-B domain cavity but not binding to HIF1α, resulting in inhibition of heterodimerization of HIF-2α to HIF1β (ARNT) but not resulting in inhibition of heterodimerization of HIF1α to HIF1β (ARNT), wherein in said compound and/or said pharmaceutically acceptable salt thereof B1 and B2 are independently chosen from cycloalkyl, heterocycloalkyl, aryl, and heteroaryl;

L is chosen from a bond, (CH2)mO(CH$_2$)n, alkylene, (CH2)mS(CH$_2$)n, (CH2)m NR'(CH$_2$)n, C(O)NR", SO$_2$, SO$_2$NR''', SO, (CH$_2$)mC(O)(CH$_2$)n, cycloalkylene, heterocycloalkylene, arylene, and heteroarylene;

R', R" and R''' are independently selected from H and alkyl;

each of the cycloalkyl, cycloalkylene, alkylene, heterocycloalkyl, heterocycloalkylene, aryl, arylene, heteroaryl, and heteroarylene is, independently from one another, optionally substituted with at least one substituent selected from alkyl, alkenyl, alkynyl, carboxyl, sulfonyl hydroxide, halo, oxo, NO$_2$, NR$^1$R$^2$, CN, ureido, OR$^3$, alkylsulfonyl, aminosulfonyl, alkylcarbonyl, alkoxycarbonyl, aminocarbonyl, alkylsulfinyl, alkylsulfonimidoyl, cycloalkyl, heterocycloalkyl, aryl, and heteroaryl, with each of the substituent alkyl, alkenyl, alkynyl, alkoxy, alkylsulfonyl, alkylcarbonyl, alkoxycarbonyl, alkylsulfinyl, alkylsulfonimidoyl, cycloalkyl, heterocycloalkyl, aryl, and heteroaryl being, independent from one another, further optionally substituted with at least one group A, and each of the substituents ureido, aminosulfonyl, and aminocarbonyl being, independently from one another, further optionally substituted with at least one group B;

R$^1$, R$^2$, and R$^3$ are independently selected from H, alkyl, alkylcarbonyl, and alkylsulfonyl, with each of the alkyl, alkylcarbonyl, and alkylsulfonyl being, independently from one another, optionally substituted with at least one group A;

A is selected from alkoxy, halo, hydroxyl, CN, NO$_2$, alkylcarbonyl, alkoxycarbonyl, aureido, aminosulfonyl, aminocarbonyl, and carboxyl;

B is selected from alkyl and aryl, with each of the alkyl and aryl being, independently from one another, optionally substituted with at least one group A;

each of the above m and n is independently selected from 0, 1, 2, 3, 4, and 5, provided that the compound is not 1-nitro-4-phenoxybenzene, N-benzyl-2-nitro-4-(trifluoromethyl)aniline, N-(cyclopropylmethyl)-2-nitro-4-(trifluoromethyl)aniline, 2-nitro-N-(thiophen-3-ylmethyl)-4-(trifluoromethyl)aniline, N-(furan-2-ylmethyl)-2-nitro-4-(trifluoromethyl)aniline, or N-(2-nitro-4-(trifluoromethyl)phenyl)morpholin-4-amine.

In some embodiments, the certain small molecule is not 1-nitro-4-phenoxybenzene, N-benzyl-2-nitro-4-(trifluoromethyl)aniline, N-(cyclopropylmethyl)-2-nitro-4-(trifluoromethyl)aniline, 2-nitro-N-(thiophen-3-ylmethyl)-4-(trifluoromethyl)aniline, or N-(furan-2-ylmethyl)-2-nitro-4-(trifluoromethyl)aniline.

In some embodiments, it is further provided that any permutation and combination of the compounds, 1-nitro-4-phenoxybenzene, N-benzyl-2-nitro-4-(trifluoromethyl)aniline, N-(cyclopropylmethyl)-2-nitro-4-(trifluoromethyl)aniline, 2-nitro-N-(thiophen-3-ylmethyl)-4-(trifluoromethyl)aniline, or N-(furan-2-ylmethyl)-2-nitro-4-(trifluoromethyl)aniline and pharmaceutically acceptable salts thereof may not fall within the scope of the term "certain small molecules."

In some embodiments, B1 and B2 are independently selected from aryl and heteroaryl, and each of the aryl and heteroaryl is optionally substituted with at least one substituent as defined herein.

In some embodiments, L is selected from (CH$_2$)mNR' (CH$_2$)n, and each of R', m, and n is as defined herein.

In some embodiments, L is a heteroarylene optionally substituted with at least one substituent as defined herein.

In some embodiments, the certain small molecule is a compound of formula (II),

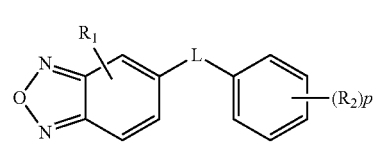

(II)

and/or a pharmaceutically acceptable salt thereof, wherein L is selected from NH and NH(CH2), R$_1$ is a NO$_2$, R$_2$ is independently selected from NO$_2$, halo, and alkyl optionally substituted with at least one group selected from halo, and p is 1, 2, 3, 4, or 5.

In some embodiments, the certain small molecule is selected from the following compounds of formula (I):

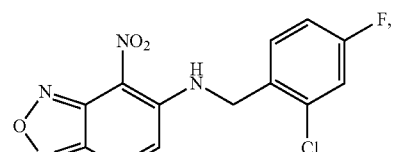

N-(2-chloro-4-fluorobenzyl)-4-nitrobenzo[c][1,2,5]oxadiazol-5-amine

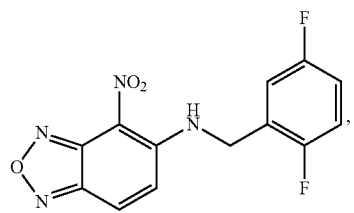

N-(2,5-difluorobenzyl)-4-
nitrobenzo[c][1,2,5]oxadiazol-5-amine

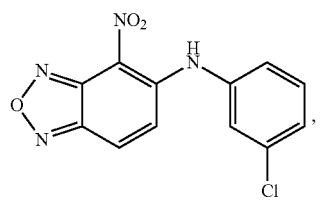

N-(3-chlorophenyl)-4-
nitrobenzo[c][1,2,5]oxadiazol-5-amine

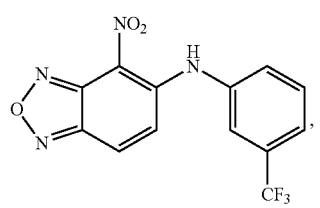

4-nitro-N-(3-(trifluoromethyl)phenyl)
benzo[c][1,2,5]oxodiazol-5-amine

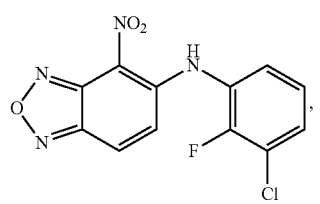

N-(3-chloro-2-fluorophenyl)-4-
nitrobenzo[c][1,2,5]oxadiazol-5-amine

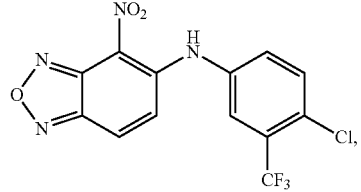

N-(4-chloro-3-(trifluoromethyl)phenyl)-4-
nitrobenzo[c][1,2,5]oxadiazol-5-amine

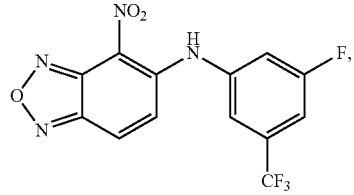

N-(3-fluoro-5-(trifluoromethyl)phenyl)-4-
nitrobenzo[c][1,2,5]oxadiazol-5-amine

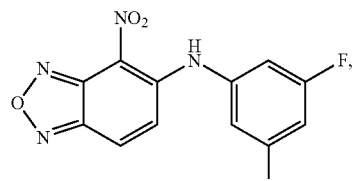

N-(3,5-difluorophenyl)-4-
nitrobenzo[c][1,2,5]oxadiazol-5-amine

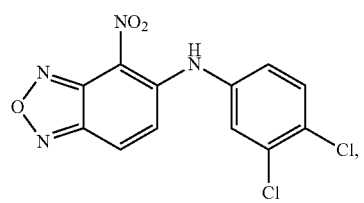

N-(3,4-diclorophenyl)-4-
nitrobenzo[c][1,2,5]oxadiazol-5-amine

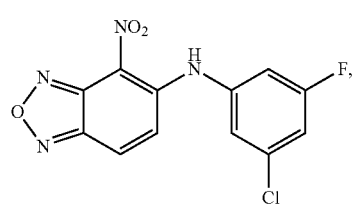 [SMILES: O=[N+]([O-])c1c(Nc2ccc(Cl)c(Cl)c2)ccc2nonc12]

N-(3-chloro-5-fluorophenyl)-4-
nitrobenzo[c][1,2,5]oxadiazol-5-amine

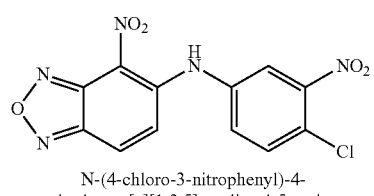

N-(4-chloro-3-nitrophenyl)-4-
nitrobenzo[c][1,2,5]oxadiazol-5-amine

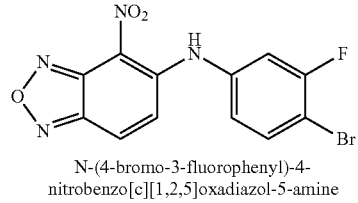

N-(4-bromo-3-fluorophenyl)-4-
nitrobenzo[c][1,2,5]oxadiazol-5-amine

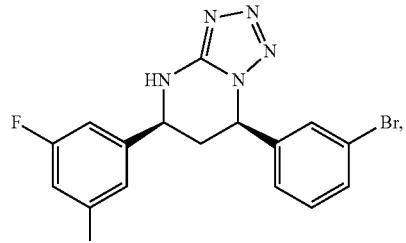

(5S,7R)-5-(3-bromo-5-fluorophenyl)-7-
(3-bromophenyl)-4,5,6,7-
tetrahydrotetrazolo[1,5-a]pyrimidine[1]

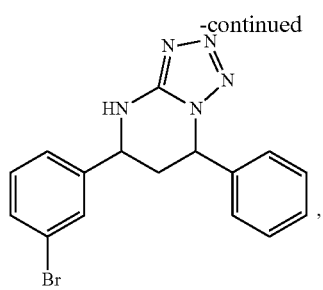

(+/−)-(cis)-5-(3-bromophenyl)-7-
phenyl-4,5,6,7-
tetrahydrotetrazolo[1,5-a]pyrimidine

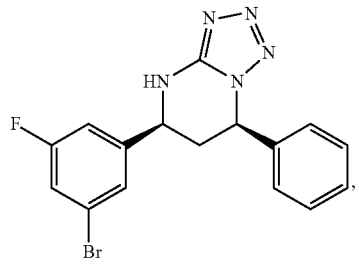

(5S,7R)-5-(3-bromo-5-fluorophenyl)-7-
phenyl-4,5,6,7-
tetrahydrotetrazolo[1,5-a]pyrimidine[1]

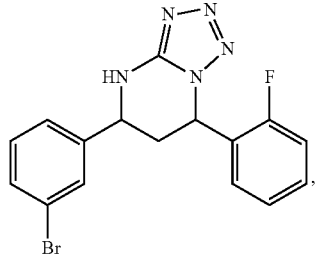

(+/−)-(cis)-5-(3-bromophenyl)-7-
(2-fluorophenyl)-4,5,6,7-
tetrahydrotetrazolo[1,5-a]pyrimidine

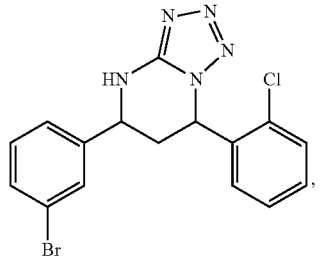

(+/−)-(cis)-5-(3-bromophenyl)-7-
(2-chlorophenyl)-4,5,6,7-
tetrahydrotetrazolo[1,5-a]pyrimidine

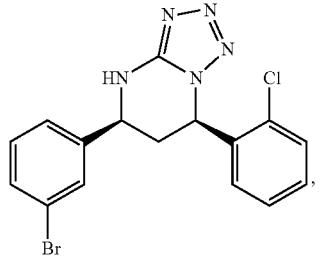

(5S,7R)-5-(3-bromophenyl)-7-
(2-chlorophenyl)-4,5,6,7-
tetrahydrotetrazolo[1,5-a]pyrimidine[1]

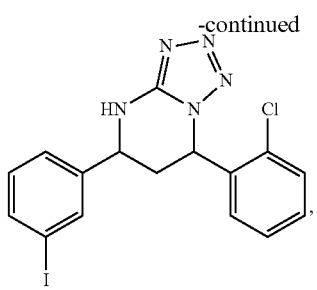

(+/−)-(cis)-7-(2-chlorophenyl)-5-
(3-iodophenyl)-4,5,6,7-
tetrahydrotetrazolo[1,5-a]pyrimidine

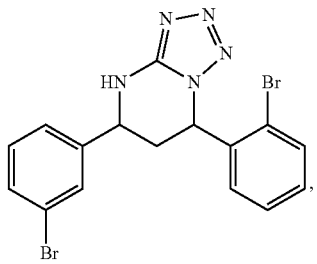

(+/−)-(cis)-7-(2-bromophenyl)-5-
(3-bromophenyl)-4,5,6,7-
tetrahydrotetrazolo[1,5-a]pyrimidine

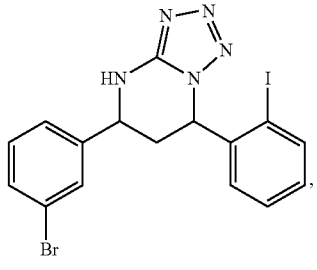

(+/−)-(cis)-5-(3-bromophenyl)-7-
(2-iodophenyl)-4,5,6,7-
tetrahydrotetrazolo[1,5-a]pyrimidine

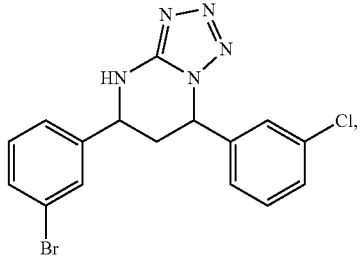

(+/−)-(cis)-5-(3-bromophenyl)-7-
(3-chlorophenyl)-4,5,6,7-
tetrahydrotetrazolo[1,5-a]pyrimidine

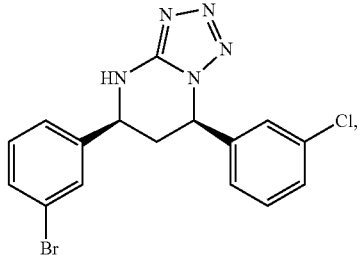

((5S,7R)-5-(3-bromophenyl)-7-
(3-chlorophenyl)-4,5,6,7-
tetrahydrotetrazolo[1,5-a]pyrimidine[1]

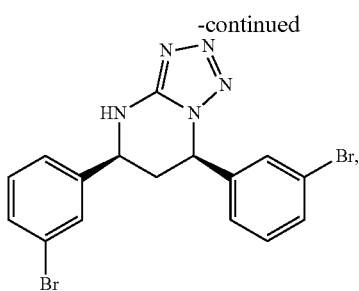

(5S,7R)-5,7-bis(3-bromophenyl)-4,5,6,7-
tetrahydrotetrazolo[1,5-a]pyrimidine

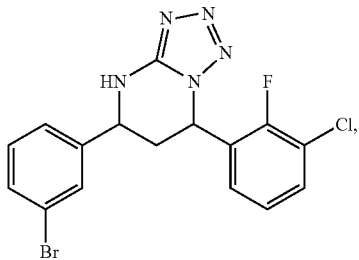

(+/-)-(cis)-5-(3-bromophenyl)-7-
(3-chloro-2-fluorophenyl)-4,5,6,7-
tetrahydrotetrazolo[1,5-a]pyrimidine

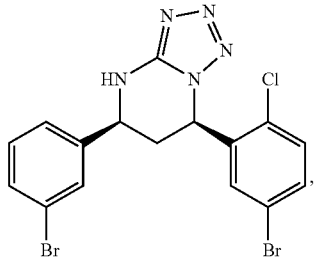

(5S,7R)-7-(5-bromo-2-chlorophenyl)-5-
(3-bromophenyl)-4,5,6,7-
tetrahydrotetrazolo[1,5-a]pyrimidine[1]

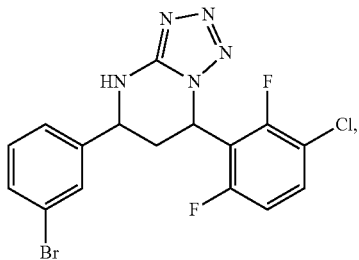

(+/-)-(cis)-5-(3-bromophenyl)-7-
(3-chloro-2,6-difluorophenyl)-4,5,6,7-
tetrahydrotetrazolo[1,5-a]pyrimidine

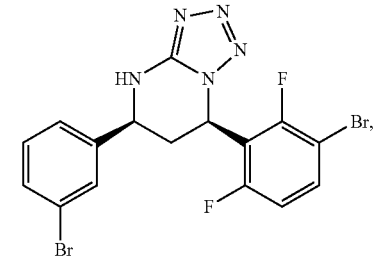

(5S,7R)-7-(3-bromo-2,6-difluorophenyl)-5-
(3-bromophenyl)-4,5,6,7-
tetrahydrotetrazolo[1,5-a]pyrimidine[1]

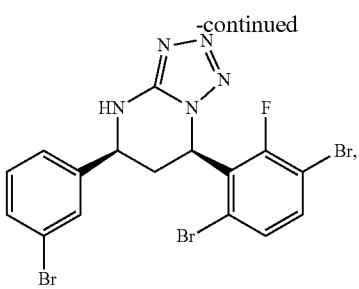

(5S,7R)-7-(3-bromophenyl)-7-
(3,6-dibromo-2-fluorophenyl)-4,5,6,7-
tetrahydrotetrazolo[1,5-a]pyrimidine[1]

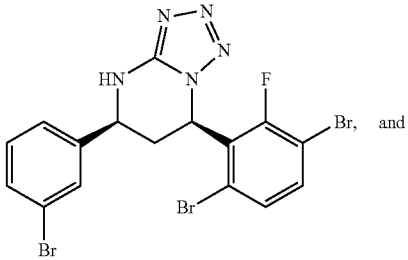

Br, and (5S,7R)-5-(3-bromophenyl)-7-
(3,6-dibromo-2-fluorophenyl)-4,5,6,7-
tetrahydrotetrazolo[1,5-a]pyrimidine[1]

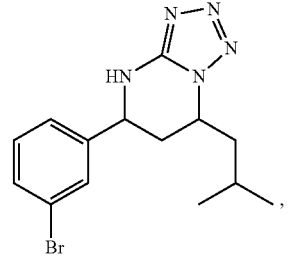

(+/-)-(cis)-5-(3-bromophenyl)-
7-isobutyl-4,5,6,7-
tetrahydrotetrazolo[1,5-a]pyrimidine

[1]Absolute stereochemistry assigned by analogy with (5S, 7R)-5,7-bis(3-bromophenyl)-4,5,6,7-tetrahydrotetrazolo[1,5-a]pyrimidine and pharmaceutically acceptable salts thereof.

The present disclosure provides a method of inhibiting heterodimerization of HIF-2α to HIF1β (ARNT) but not inhibiting heterodimerization of HIF1α to HIF1β (ARNT) comprising binding to a HIF-2α PAS-B domain cavity but not binding to HIF1α with a means for said inhibiting. The means are linked to the certain small molecules disclosed herein and statutory equivalents under 35 U.S.C. §112(f) of those disclosed certain small molecules.

In some embodiments, the means is linked to at least one certain small molecule described herein, provided the means is not N-(2-nitro-4-(trifluoromethyl)phenyl)morpholin-4-amine.

EXAMPLES

The examples below are intended to be purely exemplary and should not be considered to be limiting in any way. Efforts have been made to ensure accuracy with respect to numbers used (for example, amounts, temperature, etc.) but some experimental errors and deviations should be taken into account.

Example 1

Synthesis of N-(3-chloro-5-fluorophenyl)-4 nitrobenzo[c][1,2,5] oxadiazol-5-amine

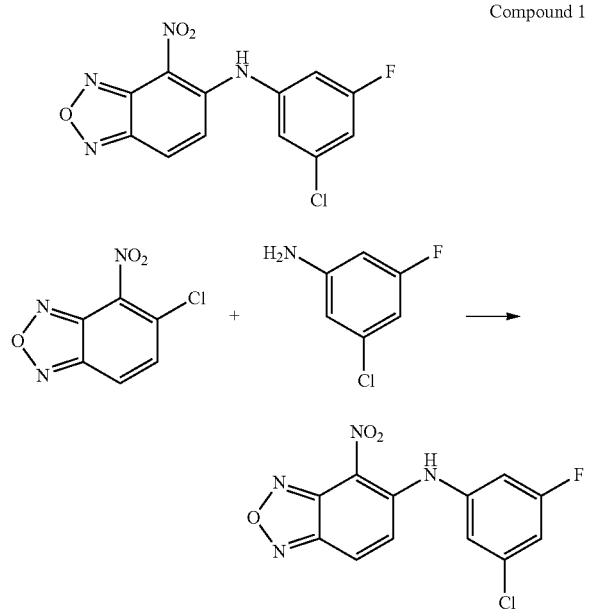

Compound 1

5-Chloro-4-nitrobenzo[c][1,2,5]oxadiazole (115 mg, 0.58 mmol) was combined with 3-chloro-5-fluoroaniline (83.7 mg, 0.58 mmol) in DMF (0.55 mL), and the mixture was heated at 110° C. for 1.25 hours. The mixture was cooled to ambient temperature, resulting in the formation of a solid mass. This solid was resuspended in ethyl acetate and transferred to a larger volume of ethyl acetate (100 mL). This was sonicated to completely dissolve the solids. The organic layer was washed 5 times with water (50 mL) and brine, separated, and dried over $Na_2SO_4$, then filtered and concentrated in vacuo. The resultant yellow solid was resuspended in ethyl acetate (3 mL), and filtered. The solids were washed with fresh ethyl acetate, and air-dried. N-(3-chloro-5-fluorophenyl)-4-nitrobenzo[c][1,2,5]oxadiazol-5-amine was obtained as a free-flowing yellow solid, (122 mg, 69%).

Alternatively, Compound 1 can be prepared by the following procedure. A flame-dried reaction vial was charged with 5-Chloro-4-nitrobenzo[c][1,2,5]oxadiazole (50 mg, 0.25 mmol) and anhydrous DMF (1.5 mL). The mixture was treated with an aniline (0.25 mmol) and stirred at 90° C. for 3 h. After cooling to room temperature, the reaction was then diluted with ethyl acetate (5 mL) and washed with water (3×5 mL). The combined aqueous layers were extracted with ethyl acetate (2×5 mL). The combined organic layers were washed with brine (10 mL), dried over $MgSO_4$, and concentrated under reduced pressure. The resulting powder was recrystallized from 30% ethyl acetate in hexanes to provide crystals of the desired aniline derivative.

LC/MS (ES-API Negative) [M−H$^-$] m/z 307.0.

$^1$H NMR (CDCl$_3$, 400 MHz) δ11.52 (bs, 1H), 7.97 (dd, J=9.8, 0.6 Hz, 1H), 7.35 (d, J=9.8 Hz, 1H), 7.21 (ddd, J=8.1, 1.9, 1.9 Hz, 1H), 7.16 (m, 1H), 6.99 (ddd, J=8.1, 1.9, 1.9 Hz, 1H), $^{13}$C NMR (CDCl$_3$, 100 MHz) δ 164.7, 162.2, 147.6, 146.6, 144.8, 138.3, 137.3 (J=10.7 Hz), 125.5, 124.4, 122.5 (J−=3.6 Hz), 116.8 (J=24.4 Hz), 112.3 (J=23.6 Hz).

The following compounds 2-12 and 17-32 were prepared analogously to the procedures for Compound 1 by using the corresponding aniline or benzylamine and 5-chloro-4-nitrobenzo[c][1,2,5]oxadiazole under appropriate conditions recognizable to one skilled in the art.

| Compound No. | Structure | LC/MS (ESI) | NMR |
|---|---|---|---|
| 2 | N-(2-chloro-4-fluorobenzyl)-4-nitrobenzo[c][1,2,5]oxadiazol-5-amine | calc'd for ([M − H]$^-$): m/z 321.0, found: 321.0 | $^1$H NMR (400 MHz, Acetone-d$_6$) δ 8.15 (d, J = 9.9 Hz, 1H), 7.70 (d, J = 10.0 Hz, 1H), 7.63 (dd, J = 6.0 Hz, 8.7 Hz, 1H), 7.42 (dd, J = 2.6 Hz, 8.6 Hz, 1H), 7.18 (dt, J = 2.7 Hz, 8.4 Hz, 1H), 5.19 (d, J = 4.1 Hz, 2H); $^{13}$C NMR (100 MHz, Acetone-d$_6$) δ 163.0 (d, J = 247.2), 151.6, 151.4, 147.3, 146.1, 134.4 (d, J = 10.6 Hz), 131.7 (d, J = 3.5 Hz), 131.3 (d, J = 9.0 Hz), 125.8 (d, J = 3.4 Hz), 125.8, 118.0 (d, J = 25.3 Hz), 115.5 (d, J = 21.2 Hz), 45.7 |

-continued

| Compound No. | Structure | LC/MS (ESI) | NMR |
|---|---|---|---|
| 3 | N-(2,5-difluorobenzyl)-4-nitrobenzo[c][1,2,5]oxadiazol-5-amine | calc'd for [C₁₃H₇F₂N₄O₃]⁻([M − H]⁻): m/z 305.1, found: 305.0. | $^1$H NMR (400 MHz, Acetone-d₆) δ 8.16 (d, J = 9.9 Hz, 1H), 7.74 (d, J = 9.9 Hz, 1H), 7.35 (m, 1H), 7.28 (m, 1H), 7.17 (m, 1H), 5.21 (d, J = 5.7 Hz, 2H); $^{13}$C NMR (100 MHz, Acetone-d₆) δ 159.8 (dd, J = 2.3 Hz, 245.2 Hz), 157.4 (dd, J = 1.4 Hz, 243.6 Hz), 151.5, 151.3, 147.3, 146.1, 127.2 (dd, J = 7.5 Hz, 17.1 Hz), 125.8, 125.6, 117.9 (dd, J = 8.8 Hz, 24.2 Hz), 116.9 (dd, J = 8.8 Hz, 24.3 Hz), 116.4 (dd, J = 4.3 Hz, 25.4 Hz), 42.2 |
| 4 | N-(4-fluoro-2-(trifluoromethyl)benzyl)-4-nitrobenzo[c][1,2,5]oxadiazol-5-amine | calc'd for [C₁₄H₇F₄N₄O₃]⁻([M − H]⁻): m/z 355.1, found 355.0 | $^1$H NMR (400 MHz, Acetone-d₆) δ 10.89 (bs, 1H), 8.15 (d, J = 10 Hz, 1H), 7.79 (dd, J = 5.3 Hz, 8.8 Hz, 1H), 7.65 (dd, J = 2.8 Hz, 9.0 Hz, 1H), 7.60 (d, J = 9.9 Hz, 1H), 7.47 (dt, J = 2.8 Hz, 8.3 Hz, 1H), 5.31 (d, J = 6.1 Hz, 2H); $^{13}$C NMR (100 MHz, Acetone-d₆) δ 162.6 (d, J = 246.1 Hz), 151.5, 147.3, 146.1, 142.9, 132.2 (d, J = 8.2 Hz), 131.8, 130.1, 129.2, 128.6, 125.8 (d, J = 29.8 Hz), 120.6 (d, J = 21.3 Hz), 115.1 (dq, J = 5.8 Hz, 25.5 Hz), 44.6;) |
| 5 | N-(3-chlorophenyl)-4-nitrobenzo[c][1,2,5]oxadiazol-5-amine | LCMS (ESI) calc'd for [C₁₂H₆ClN₄O₃]⁻ ([M − H]⁻): m/z 289.0, found 289.0 | $^1$H NMR (400 MHz, Acetone-d₆) δ 11.7 (bs, 1H), 8.12 (d, 1H, 9.9 Hz), 7.65 (m, 1H), 7.61 (d, 1H, J = 9.9 Hz), 7.65 (m, 1H), 7.61 (d, 1H, J = 7.9 Hz), 7.52 (m, 3H) $^{13}$C NMR (100 MHz, Acetone-d₆) δ 148.5, 146.9, 145.1, 138.3, 134.7, 131.3, 128.1, 126.7, 126.3, 125.3, 124.3,. 108.6. |
| 6 | 4-nitro-N-(3-(trifluoromethyl)phenyl)benzo[c][1,2,5]oxadiazol-5-amine | calc'd for [C₁₃H₆F₃N₄O₃]⁻([M − H]⁻): m/z 323.0, found 323.0. | $^1$H NMR (400 MHz, Acetone-d₆) δ 11.80 (bs, 1H), 8.10 (d, J = 9.8 Hz, 1H), 7.95 (s, 1H), 7.87 (m, 1H), 7.84 (m, 2H), 7.63 (d, 1H, J = 9.8 Hz). $^{13}$C NMR (100 MHz, Acetone-d₆) δ 148.7, 148.9, 145.1, 137.9, 131.5 (J = 30.0 Hz), 131.0, 130.7, 126.2, 124.7 (J = 3.8 Hz), 124.4, 123.8 (J = 271 Hz), 123.7 (J = 3.9 Hz), 114.4 |

-continued

| Compound No. | Structure | LC/MS (ESI) | NMR |
|---|---|---|---|
| 7 | N-(4-bromo-3-fluorophenyl)-4-nitrobenzo[c]1,2,5]oxadiazol-5-amine | | |
| 8 | N-(3-chloro-2-fluorophenyl)-4-nitrobenzo[c][1,2,5]oxadiazol-5-amine | calc'd for $[C_{12}H_5ClFN_4O_3]^-$ ($[M - H]^-$): m/z 307.0, found 307.0. | $^1$H NMR (400 MHz, Acetone-$d_6$) δ 11.5 (bs, 1H), 8.15 (d, 1H, J = 9.9 Hz), 7.67 (m, 2H), 7.46 (m, 2H). $^{13}$C NMR (100 MHz, Acetone-$d_6$) δ 153.5 (J = 249.0 Hz), 148.6, 146.9, 145.0, 130.5, 128.0, 126.0 (J = 1.0 Hz), 125.7 (J = 5.0 Hz), 124.7, 121.7 (J = 16.0 Hz), 94.8. |
| 9 | N-(4-chloro-3-(trifluoromethyl)phenyl)-4-nitrobenzo[c][1,2,5]oxadiazol-5-amine | calc'd for $[C_{13}H_6ClF_3N_4O_3]^-$ ($[M - H]^-$): m/z 357.0, found 357.0. | $^1$H NMR (400 MHz, Acetone-$d_6$) δ 11.73 (bs, 1H), 8.13 (d, 1H, J = 9.9 Hz), 8.08 (s, 1H), 7.89 (d, 1H, J = 1.4 Hz), 7.62 (d, 1H, J = 9.9 Hz), $^{13}$C NMR (100 MHz, Acetone-$d_6$) δ 149.6, 147.9, 146.0, 142.8, 137.7, 134.1, 132.9, 129.7, 127.4 (q, J = 5.2 Hz), 125.4 (q, J = 3.7 Hz), 123.6 (q, J = 266 Hz), 117.1, 115.8 (q, J = 25.9 Hz). |
| 10 | N-(3-fluoro-5-(trifluoromethyl)phenyl)-4-nitrobenzo[c][1,2,5]oxadiazol-5-amine | calc'd for $[C_{13}H_6F_4N_4O_3]^-$($[M - H]^-$): m/z 341.0, found 341.0 | $^1$H NMR (400 MHz, Acetone-$d_6$) δ 11.67 (bs, 1H), 8.16 (d, 1H, J = 9.9 Hz), 7.84 (s, 1H), 7.77 (ddd, 1H, J = 2.2, 2.2, 9.3 Hz), 7.66 (d, 1H, J = 9.8 Hz), 7.66 (d, 1H, J = 8.5 Hz). $^{13}$C NMR (100 MHz, Acetone-$d_6$) δ 163.0 (d, J = 260 Hz), 148.2, 146.9, 145.0, 140.0 (J = 11.6 Hz), 126.4, 124.5, 121.8 (J = 3.2 Hz), 119.9 (dq, J = 3.4, 3.7 Hz), 118.0 (d, J = 23.8 Hz), 116.5 (d, J = 281 Hz), 112.1 (dq, J = 3.7, 24.8 Hz), 94.9. |
| 11 | N-(3,5-difluorophenyl)-4-nitrobenzo[c][1,2,5]oxadiazol-5-amine | calc'd for $[C_{12}H_5F_2N_4O_3]^-$($[M - H]^-$): m/z 291.0, found 291.0 | $^1$H NMR (400 MHz, Acetone-$d_6$) δ 11.65 (bs, 1H), 8.15 (d, 1H, J = 9.8 Hz), 7.66 (dd, 1H, J = 3.1, 9.9 Hz), 7.32 (d, 2H, J = 5.8 Hz), 7.18 (ddd, 1H, J = 2.4, 2.4, 9.9 Hz), $^{13}$C NMR (100 MHz, Acetone-$d_6$) δ 163.5 (d, J = 243.9 Hz), 163.3 (d, J = 246.7 Hz), 148.3, 146.9, 145.0, 139.7 (dd, J = 12.7, 13.0 Hz), 126.4, 124.5, 110.3 (d, J = 27.8 Hz), |

| Compound No. | Structure | LC/MS (ESI) | NMR |
|---|---|---|---|
| | | | 110.3 (d, J = 11.4 Hz), 103.3 (d, J = 18.0, 33.0 Hz), 94.9. |
| 12 | N-(3,4-dichlorophenyl)-4-nitrobenzo[c][1,2,5]oxadiazol-5-amine | calc'd for [C₁₂H₅C₁₂N₁₄O₃]⁻([M − H]⁻): m/z 323.0, found 323.0 | ¹H NMR (400 MHz, Acetone-d₆) δ 11.7 (bs, 1H), 8.13 (d, 1H, J = 9.9 Hz), 7.84 (d, 1H, 2.4 Hz), 7.79 (d, 1H, 8.6 Hz), 7.59 (m, 2H). ¹³C NMR (100 MHz, Acetone-d₆) δ 149.6, 147.9, 146.1, 138.0, 133.8, 132.6, 132.3, 129.8, 127.9, 127.3, 125.3, 107.9. |
| 17 | 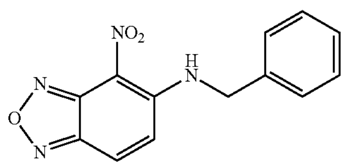 [SMILES: O=[N+]([O-])c1c(NCc2ccccc2)ccc2nonc12] | calc'd for [C₁₃H₉N₄O₃]⁻([M − H]⁻): m/z 269.1, found 269.1 | ¹H NMR (400 MHz, Acetone-d₆) δ 8.11 (d, J = 9.9 Hz, 1H), 7.72 (d J = 9.9 Hz 1H), 7.50 (d, J = 7.5 Hz, 2H), 7.42 (t, J = 7.3 Hz, 2H), 7.34 (t, J = 7.4 Hz, 1H), 5.14 (d, J = 6.1 Hz, 2H); ¹³C NMR (100 MHz, Acetone-d₆) δ 151.6, 147.2, 146.1, 138.0, 129.9, 128.7, 128.0, 125.99, 125.5, 125.5, 48.1 |
| 18 | 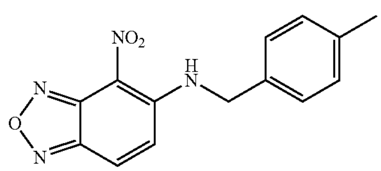 [SMILES: Cc1ccc(CNc2ccc3nonc3c2[N+](=O)[O-])cc1] | calc'd for [C₁₄H₁₁N₄O₃]⁻([M − H]⁻): m/z 283.1, found 283.1 | ¹H NMR (400 MHz, Acetone-d6) δ 8.10 (d, J = 10.0 Hz, 1H), 7.72 (d, J = 10.0 Hz, 1H), 7.38 (d, J = 7.9 Hz, 2H), 7.23 (d, J = 8.3 Hz, 2H), 5.08 (d, J = 6.0 Hz, 2H); ¹³C NMR (100 MHz, Acetone-d6) δ 151.6, 147.2, 146.11, 138.4, 135.0, 130.5, 128.1, 126.0, 126.0, 125.5, 48.0, 21.1 |
| 19 | 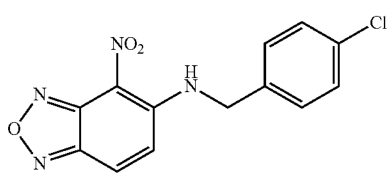 [SMILES: O=[N+]([O-])c1c(NCc2ccc(Cl)cc2)ccc2nonc12] | calc'd for [C₁₃H₈ClN₄O₃]⁻([M − H]⁻): m/z 303.0, found 303.0. | ¹H NMR (400 MHz, Acetone-d₆) δ 8.10 (d, J = 10.0 Hz, 1H), 7.69 (d, J = 9.9 Hz, 1H), 7.54 (d, J = 11.5 Hz, 2H), 7.43 (d, J = 8.5 Hz, 2H), 5.16 (d, J = 6.7 Hz, 2H); ¹³C NMR (100 MHz, Acetone-d6) δ 151.5, 151.4, 147.2, 146.1, 137.1, 134.0, 129.8, 129.8, 129.8, 125.9, 125.9, 125.6, 47.4 |
| 20 | 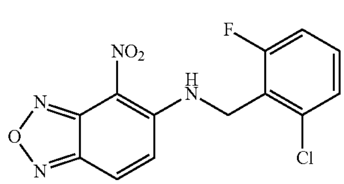 [SMILES: O=[N+]([O-])c1c(NCc2c(F)cccc2Cl)ccc2nonc12] | calc'd for [C₁₃H₇ClFN₄O₃]⁻([M − H]⁻): m/z 321.0, found 321.0. | ¹H NMR (400 MHz, Acetone-d₆) δ 10.84 (bs, 1H), 8.26 (d, J = 9.9 Hz, 1H), 7.92 (d, J = 9.9 Hz, 1H), 7.52 (m, 1H), 7.43 (d, J = 8.1 Hz, 1H), 7.29 (t, J = 9.7 Hz, 1H), 5.24 (d, J = 5.8 Hz, 2H); ¹³C NMR (100 MHz, Acetone-d₆) δ 162.3 (d, J = 247.9 Hz), 151.0, |

| Compound No. | Structure | LC/MS (ESI) | NMR |
|---|---|---|---|
| | | | 147.2, 146.0, 135.9, 132.4 (d, J = 10.0 Hz), 129.2, 127.2 (d, J = 3.4 Hz), 126.1, 125.2 (d, J = 2.6 Hz), 123.1 (d, J = 17.3 Hz), 115.9 (d, J = 22.6 Hz), 40.2 |
| 21 | 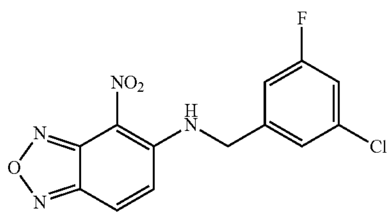 [SMILES: O=[N+]([O-])c1c(NCc2cc(F)cc(Cl)c2)ccc2nonc12] | calc'd for [C$_{13}$H$_7$ClFN$_4$O$_3$]$^-$([M − H]$^-$): m/z 321.0, found 321.0. | $^1$H NMR (400 MHz, Acetone-d$_6$) δ 10.95 (bs, 1H), 8.12 (d, J = 9.9 Hz, 1H), 7.68 (d, J = 10.0 Hz, 1H), 7.42 (s, 1H), 7.31 (dt, J = 1.8 Hz, 9.5 Hz, 1H), 7.22 (dt, J = 2.1 Hz, 8.6 Hz, 1H), 5.20 (d, J = 6.5 Hz, 2H); $^{13}$C NMR (100 MHz, Acetone-d$_6$) δ 163.8 (d, J = 247.4 Hz), 151.5, 147.3, 146.1, 143.0 (d, J = 8.0 Hz), 136.0 (d, J = 10.8 Hz), 125.8, 125.7, 124.1, 124.1, 116.1 (d, J = 25.1 Hz), 113.7 (d, J = 22.5 Hz), 47.1 |
| 22 | 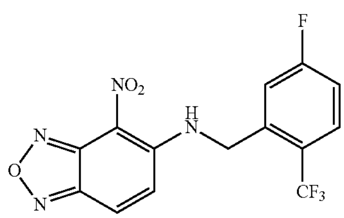 [SMILES: O=[N+]([O-])c1c(NCc2cc(F)ccc2C(F)(F)F)ccc2nonc12] | calc'd for [C$_{14}$H$_7$F$_4$N$_4$O$_3$]$^-$([M − H]$^-$): m/z 355.1, found 355.0. | $^1$H NMR (400 MHz, Acetone-d$_6$) δ 10.92 (bs, 1H), 8.15 (d, J = 10.0 Hz, 1H), 7.94 (dd, J = 5.4 Hz, 8.7 Hz, 1H), 7.56 (d, J = 10.0 Hz, 1H), 7.51 (d, J = 10.0 Hz, 1H), 7.34 (t, J = 8.2 Hz, 1H), 5.35 (d, J = 6.3 Hz, 2H); $^{13}$C NMR (100 MHz, Acetone-d$_6$) δ 166.0 (d, J = 250.7 Hz), 151.6, 147.3, 146.2, 140.3 (d, J = 8.0 Hz), 130.4 (dq, J = 5.9 Hz, 9.6 Hz), 129.2, 126.5, 125.8 (d, J = 37 Hz), 123.8, 121.5, 116.7 (d, J = 24 Hz), 115.8 (d, J = 22 Hz), 44.8 |
| 23 | 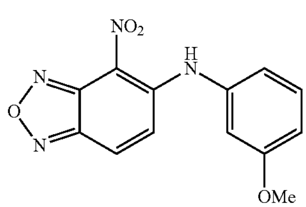 [SMILES: COc1cccc(Nc2ccc3nonc3c2[N+](=O)[O-])c1] | calc'd for [C$_{13}$H$_9$N$_4$O$_4$]$^-$([M − H]$^-$): m/z 285.1, found 285.0. | $^1$H NMR (400 MHz, Acetone-d$_6$) δ 8.10 (d, 1H, J = 9.9 Hz), 7.50 (m, 2H), 7.14 (dd, 1H, J = 2.1, 2.1 Hz), 7.08 (m, 2H), 3.87 (s, 3H), $^{13}$C NMR (100 MHz, Acetone-d$_6$) δ 160.9, 146.9, 145.1, 141.3, 130.6, 130.6, 130.1, 126.1, 123.8, 120.7, 118.5, 93.8, 55.1. |
| 24 | 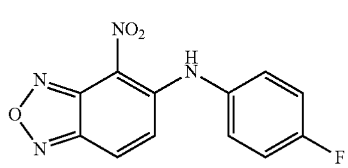 [SMILES: O=[N+]([O-])c1c(Nc2ccc(F)cc2)ccc2nonc12] | calc'd for [C$_{12}$H$_6$FN$_4$O$_3$]$^-$([M − H]$^-$): m/z 273.0, found 273.0. | $^1$H NMR (400 MHz, Acetone-d$_6$) δ 11.73 (bs, 1H), 8.08 (d, 1H. J = 9.9 Hz), 7.60 (m, 2H), 7.44 (d, 1H, J = 9.9 Hz), 7.38 (m, 2H) $^{13}$C NMR (100 MHz, Acetone-d$_6$) δ 163.0 (J = 252.0 Hz), 150.3, 147.8, 146.2, 130.0 (J = 8.9 Hz), 127.2, 127.1, 125.3, 117.6 (J = 23.0 Hz), 108.8. |

-continued

| Compound No. | Structure | LC/MS (ESI) | NMR |
|---|---|---|---|
| 25 | 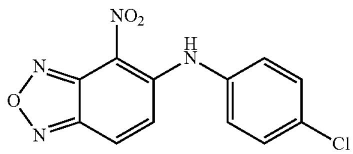 [SMILES: O=[N+]([O-])c1c(Nc2ccc(Cl)cc2)ccc2nonc12] | calc'd for [$C_{12}H_6ClN_4O_3$]$^-$([M − H]): m/z 289.0, found 289.0 | $^1$H NMR (400 MHz, Acetone-d$_6$) δ 11.7 (bs, 1H), 8.10 (d, 1H, J = 9.9 Hz), 7.6 (m, 4H), 7.50 (d, 1H, 9.9 Hz) $^{13}$C NMR (100 MHz, Acetone-d$_6$) δ 147.8, 146.2, 142.3, 134.3, 131.2 130.9, 129.4, 127.2, 125.3, 109.5. |
| 26 | 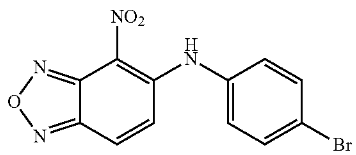 [SMILES: O=[N+]([O-])c1c(Nc2ccc(Br)cc2)ccc2nonc12] | calc'd for [$C_{12}H_6BrN_4O_3$]$^-$([M − H]$^-$): m/z 333.0, found 333.0. | $^1$H NMR (400 MHz, Acetone-d$_6$) δ 11.7 (bs, 1H), 8.10 (d, 1H, J = 9.9 Hz), 7.77 (d, 2H, J = 8.8 Hz), 7.52 (m, 3H), $^{13}$C NMR (100 MHz, Acetone-d$_6$) δ 147.8, 146.0, 134.0, 133.0, 127.4, 127.4, 127.3, 125.3, 124.8, 122.1 |
| 27 | 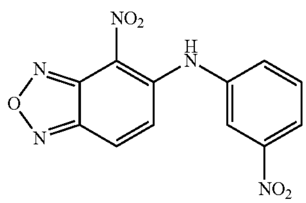 [SMILES: O=[N+]([O-])c1cccc(Nc2ccc3nonc3c2[N+](=O)[O-])c1] | calc'd for [$C_{12}H_6N_5O_5$]$^-$([M − H]$^-$): m/z 300.0, found 300.0. | $^1$H NMR (400 MHz, Acetone-d$_6$) δ 11.81 (bs, 1H), 8.47 (dd, 1H, J = 2.1, 2.1 Hz), 8.34 (d, 1H, J = 8.2 Hz), 8.13(d, 1H, J = 9.9 Hz), 8.04 (d, 1H, J = 9.0 Hz), 7.90 (dd, 1H, J = 8.1, 8.1 Hz), 7.60 (d, 1H, J = 9.8 Hz). $^{13}$C NMR (100 MHz, Acetone-d6) δ 146.9, 145.1, 138.3, 133.0, 131.1, 127.0, 126.2, 124.8, 124.5, 122.6, 121.8, 99.3. |
| 28 | 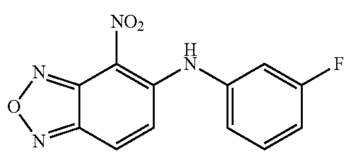 [SMILES: O=[N+]([O-])c1c(Nc2cccc(F)c2)ccc2nonc12] | calc'd for [$C_{12}H_6FN_4O_3$]$^-$([M − H]$^-$): m/z 273.0, found 273.0. | $^1$H NMR (400 MHz, Acetone-d$_6$) δ 11.7 (bs, 1H), 8.12 (d, 1H, J = 9.8 Hz), 7.65 (dd, 1H, J = 8.0, 7.2 Hz), 7.55 (d, 1H, J = 9.9 Hz), 7.41 (d, 2H, J = 7.2 Hz), 7.29 (ddd, 1H, J = 8.7, 8.7, 2.2 Hz), $^{13}$C NMR (100 MHz, Acetone-d$_6$) δ 164.1 (J = 245.0 Hz), 149.7, 147.8, 146.1, 132.5 (J = 9.3 Hz), 131.6, 127.2, 125.3, 123.6 (J = 3.1 Hz), 115.9 (21.1 Hz), 114.9 (23.8 Hz), 103.1. |
| 29 | 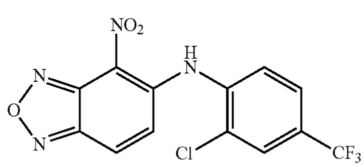 [SMILES: O=[N+]([O-])c1c(Nc2ccc(C(F)(F)F)cc2Cl)ccc2nonc12] | calc'd for [$C_{13}H_5ClF_3N_4O_3$]$^-$ ([M − H]$^-$): m/z 357.0, found 357.0. | $^1$H NMR (400 MHz, Acetone-d$_6$) δ 9.44 (bs, 1H), 8.68 (d, 1H, J = 8.8 Hz), 8.59 (s, 1H), (dd, 1H, J = 6.8, 8.5 Hz), 7.84 (s, 1H), 7.71 (d, 1H, J = 8.7 Hz). $^{13}$C NMR (100 MHz, Acetone-d$_6$) δ 146.9, 145.0, 138.2, 131.8, 127.7 (q, J = 3.9 Hz), 126.3 (q, J = 3.5 Hz), 126.2 (q, J = 278.0 Hz), 126.0, 125.5 (q, J = 5.1 Hz), 124.8 (q, J = |

-continued

| Compound No. | Structure | LC/MS (ESI) | NMR |
|---|---|---|---|
| | | | 3.7 Hz), 124.8, 121.6, 121.5. |
| 30 | ![structure] | calc'd for [C$_{12}$H$_5$ClFN$_4$O$_3$]$^-$ ([M − H]$^-$): m/z 307.0, found 307.0. | $^1$H NMR (400 MHz, Acetone-d$_6$) δ 11.6 (bs, 1H), 8.15 (d, 1H, J = 9.9 Hz), 7.60 (m, 2H), 7.50 (ddd, 1H, J = 8.8, 8.8, 1.6 Hz), 7.39 (dd, 1H, J = 9.8, 2.7 Hz) $^{13}$C NMR (100 MHz, Acetone-d$_6$) δ 158.9 (J = 248.0 Hz), 148.4, 146.9, 145.0, 136.2, 136.1, 129.0 (J = 9.1 Hz), 126.8, 126.0, 124.7 (J = 4.2 Hz), 118.8 (J = 18.5 Hz), 116.4 (J = 21.1 Hz) |
| 31 | ![structure] | calc'd for [C$_{12}$H$_5$ClFN$_4$O$_3$]$^-$ ([M − H]$^-$): m/z 307.0, found 307.0. | $^1$H NMR (400 MHz, Acetone-d$_6$) δ 11.68 (bs, 1H), 8.09 (d, 1H, J = 9.9 Hz), 7.96 (s, 1H), 7.80 (dd, 1H, J = 6.7, 2.3 Hz), 7.60 (m, 1H), 7.55 (m, 2H). $^{13}$C NMR (100 MHz, Acetone-d$_6$) δ 161.8, 157.0 (J = 250.0 Hz), 149.0, 146.8, 145.1, 134.0, 129.3, 127.7 (J = 7.7 Hz), 126.2, 124.4, 121.3 (J = 29.6 Hz), 117.7 (J = 18.4 Hz). |
| 32 | ![structure] | calc'd for [C12H6Cl—N5NaO5] + ([M + H]+): m/z 358.0, found 357.9 ([M + Na]+). | $^1$H NMR (400 MHz, DMSO) δ 11.68 (s, 1H), 8.24 (d, J = 2.5 Hz, 1H), 8.16 (d, J = 9.8 Hz, 1H); 7.93 (d, J = 8.8 Hz, 1H); 7.79 (dd, J = 8.6, 2.4 Hz, 1H); 7.45 (d, J = 9.8 Hz, 1H); $^{13}$C NMR (100 MHz, DMSO) d 148.2, 147.8, 146.8, 145.0, 137.3, 132.6, 132.0, 127.5, 124.3, 123.8, 123.7, 114.3 |

Example 2

Synthesis of Compounds 13-15

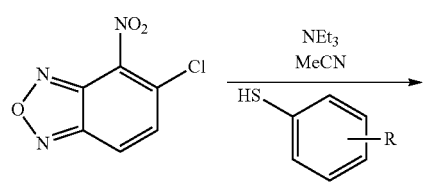

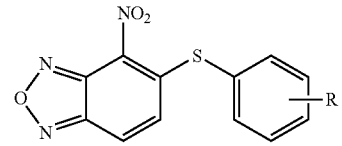

A flame-dried reaction vial was charged with benzoxadiazole (50 mg, 0.25 mmol) and anhydrous CH$_3$CN (1.5 mL). The mixture was treated with a thiophenol (0.25 mmol) and triethylamine (25 mg, 0.25 mmol). The reaction was stirred at ambient temperature and monitored by LC/MS. At the completion of the reaction, the solvent was removed under a stream of nitrogen gas. Purification by flash chromatography on silica gel (1:1 hexane:dichloromethane) provided the desired thiophenol derivative.

The following compounds 13-15 were prepared analogously to the procedures for Example 2 by using the corresponding thiophenol and 5-chloro-4-nitrobenzo[c][1,2,5]oxadiazole under appropriate conditions recognizable to one skilled in the art:

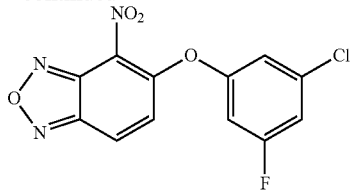

Compound 16

| Compound No. | Structure | LC/MS | NMR |
|---|---|---|---|
| 13 | (structure) | calc'd for [C$_{12}$H$_6$N$_3$O$_3$S]$^-$ ([M − H]$^-$): m/z 272.0, found 272.0. | $^1$H NMR (400 MHz, Acetone-d$_6$) δ 8.13 (d, 1H, J = 9.6 Hz), 7.78 (dd, 2H, J = 1.4, 7.8 Hz), 6.67 (m, 3H), 7.21 (d, 1H, J = 9.6 Hz). $^{13}$C NMR (100 MHz, Acetone-d$_6$) δ 150.3, 149.2, 144.4, 135.5, 131.5, 131.3, 130.7, 129.3, 121.2, 98.8 |
| 14 | (structure) | calc'd for [C$_{13}$H$_9$ClFN$_4$O$_3$]$^-$ ([M − H]$^-$): m/z 292.0, found 292.0 | $^1$H NMR (400 MHz, Acetone-d$_6$) δ 8.15 (d, 1H, J = 9.6 Hz), 7.71 (m, 1H), 7.62 (m, 2H), 7.48 (m, 1H), 7.29 (d, 1H, J = 9.6 Hz) $^{13}$C NMR (100 MHz, Acetone-d$_6$) δ 168.3 (d, J = 256.0 Hz), 154.6 (d, J = 22.5 Hz), 149.6, 137.6 (d, J = 8.4 Hz), 137.0, 136.8 (d, J = 3.2 Hz), 136.7, 128.2, 127.3 (d, J = 22.6 Hz), 126.6, 126.6, 123.5 (d, J = 21.0 Hz). |
| 15 | (structure) | calc'd for [C$_{12}$H$_6$ClF N$_3$O$_3$S]$^+$([M + H]$^+$): m/z 326.0, found 326.0 | $^1$H NMR (400 MHz, Acetone-d$_6$) δ 7.84 (d, 1H, J = 9.7 Hz), 7.21 (d, 1H, J = 9:8 Hz), 6.96 (m, 2H), 6.80 (d, 1H, J = 9.4 Hz), 3.37 (s, 3H) $^{13}$C NMR (100 MHz, Acetone-d$_6$) δ 163.0 (J = 252 Hz), 149.3, 148.6, 144.3, 136.4 (J = 10.8 Hz), 133.3 (J = 8.9 Hz), 132.1, 131.2 (J = 3.5 Hz), 122.3, 121.7, 121.0 (J = 22.7 Hz), 118.8 (J = 24.9 Hz) |

Example 3

Synthesis of Compound 16

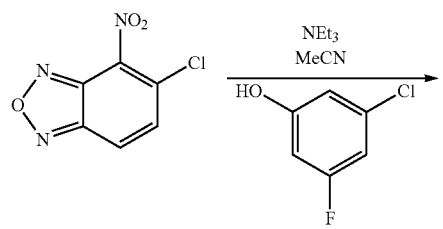

A flame-dried flask was charged with 3-chloro-5-fluorophenol (36.7 mg, 0.25 mmol, 1 equiv) and degassed and purged with nitrogen. The flask was treated with anhydrous CH$_3$CN (2.75 mL) and triethylamine (31.5 μL, 0.23 mmol, 0.9 equiv). The mixture was stirred for 30 min at room temperature and then treated with benzoxadiazole (55.1 mg, 0.28 mmol, 1.1 equiv). The solution was stirred for 24 h and then diluted with ethyl acetate. The mixture was washed with water (3×) and brine. The organic layer was dried over MgSO$_4$ and concentrated under reduced pressure. The resulting solid was then recrystallized in hexanes and dichloromethane to afford the product as a yellow solid (48 mg, 62% yield). $^1$H NMR (400 MHz, Acetone-d$_6$) δ 8.44 (d, J=9.7 Hz, 1H), 7.66 (d, J=9.6 Hz, 1H), 7.31 (m, 1H), 7.26 (dt, J=2.2 Hz, 8.5 Hz 1H), 7.23 (dt, J=2.3 Hz, 9.4 Hz, 1H);

$^{13}$C NMR (100 MHz, Acetone-d$_6$) δ 164.2 (d, J=248.6 Hz), 157.3 (d, J=12.6 Hz), 153.8, 149.0, 145.4, 136.9 (d, J=12.8 Hz), 128.9, 124.9, 116.78, 116.8, 114.3 (d, J=25.1 Hz), 107.1 (d, J=25.7 Hz).

Example 4

Synthesis of Compound 33

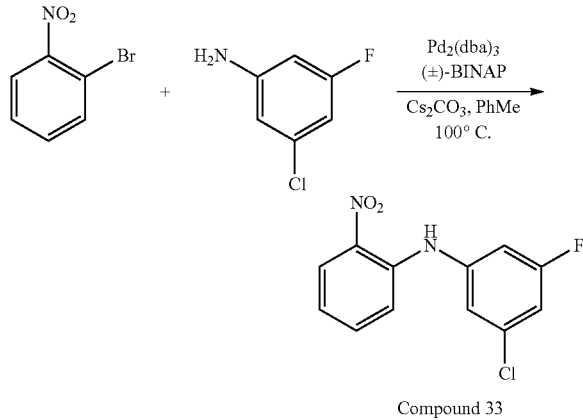

Compound 33

A flame-dried flask was charged with 2-bromonitrobenzene (50 mg, 0.25 mmol, 1 equiv) tris(dibenzylideneacetone)dipalladium (11.3 mg, 0.0012 mmol, 5 mol %), racemic 2,2'-bis(diphenylphosphino)-1,1'-binaphthyl (11.5 mg, 0.0019 mmol, 7.5 mol %), and cesium carbonate (163.1 mg, 0.50 mmol, 2 equiv). The flask was degassed and purged with nitrogen. Toluene (2.88 mL) was added, followed by 2-chloro-4-fluoroaniline (35.3 mg, 0.25 mmol, 1 equiv). The reaction was heated to 100° C. with a reflux condenser and stirred for 12 h. The mixture was cooled to room temperature, filtered through a pad of celite, dried over MgSO$_4$ and concentrated under reduced pressure. Purification by flash chromatography on silica gel (9:1 hexanes:ethyl acetate) afforded the desired aniline 33 as an orange solid (58 mg, 88% yield): $^1$H NMR (400 MHz, Acetone-d$_6$)δ 9.27 (bs, 1H), 8.18 (d, J=8.5 Hz, 1H), 7.63 (d, J=8.6 Hz, 1H), 7.52 (d, J=8.6 Hz, 1H), 7.28 (s, 1H), 7.17 (dt, J=2.2 Hz, 10.4 Hz, 1H), 7.04 (m, 2H); $^{13}$C NMR (100 MHz, Acetone-d$_6$) δ 164.2 (d, J=245.7 Hz), 144.0 (d, J=11.8 Hz), 140.9, 136.7, 136.6, 136.2 (d, J=13.0 Hz), 127.2, 120.7, 118.9, 118.9, 112.0 (d, J=25.4 Hz), 108.6 (d, J=24.5 Hz); LCMS (ESI) calc'd for [C$_{12}$H$_7$ClFN$_2$O$_2$]$^-$ ([M–H]$^-$): m/z 265.0. found 265.1.

Example 5

Synthesis of Compound 34

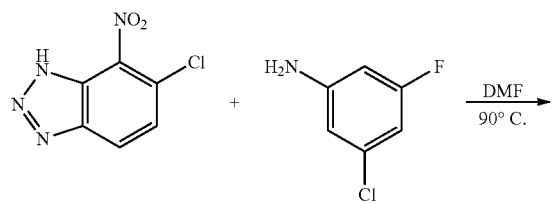

Compound 34

Compound 34 was prepared following the procedure described above for compound 1 using 6-chloro-7-nitro-1H-benzo[d][1,2,3]triazole (A) (Reid, A. K.; McHugh, C. J.; Richie, G.; Graham, D. *Tetrahedron Lett.* 2006, 47, 4201-4203) in place of 5-chloro-4-nitrobenzo[c][1,2,5]oxadiazole.

In this example, purification by flash chromatography on silica gel (10% ethyl acetate in hexanes), provided the desired compound 34 as a yellow solid (9.4 mg, 16%): $^1$H NMR (400 MHz, Acetone-d$_6$) δ 7.96 (d, 2H, J=1.2 Hz), 7.81 (d, 1H, J=5.8 Hz), 7.62 (d, 1H, J=3.6 Hz), 7.37 (dd, 1H, J=1.2, 5.7 Hz), 7.30 (d, 1H, J=3.6 Hz), 6.4 (s, 1H), 6.23 (m, 1H), 5.14 (bs, 1H) $^{13}$C NMR (100 MHz, Acetone-d$_6$) δ164.8 (d, J=242 Hz), 152.4 (d, J=12.8 Hz), 145.4, 135.6 (d, J=13.9 Hz), 135.2, 126.1, 124.0, 123.3, 110.1, 103.9 (d, J=25.8 Hz), 99.9 (d, J=24.6 Hz), 95.9. LCMS (ESI) calc'd for [C$_{12}$H$_6$ClFN$_5$O]$^-$ ([M–H]$^-$): m/z 306.0. found 306.0.

Example 6

Synthesis of Compound 35

Step 1:

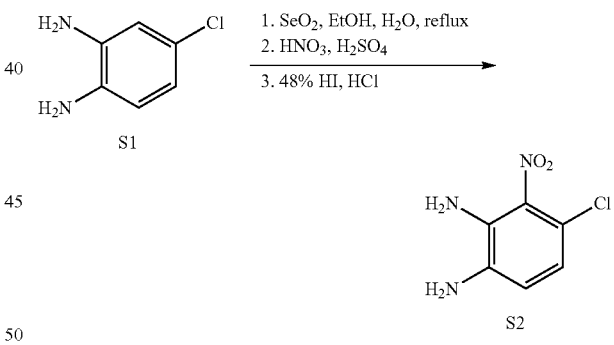

S2 was prepared analogously to a literature procedure (Keana, J. F. W.; Kher, S. M.; Cai, S. X.; Dinsmore, C. M.; Glenn, A. G.; Guastella, J.; Huang, J. C.; Ilyin, V.; Lu, Y.; Mouser, D. L.; Woodward, R. M.; Weber, E. *J. Med. Chem.* 1995, 38, 4367-4379): A solution of 3-chloroorthophenylene diamine S1 (252 mg, 1.77 mmol) in ethanol (2.0 mL) was heated to reflux and treated dropwise with a solution of selenium dioxide (216 mg, 1.94 mmol) in water (1 mL). The reaction was monitored by TLC. After 30 min, the mixture was cooled to ambient temperature and filtered via vacuum filtration to give the desired selenadiazole as a dark brown solid (253 mg, 66%). The crude product was carried forward to the next step without further purification: $^1$H NMR (400 MHz, DMSO-d$_6$) δ 7.99 (s, 1H), 7.86 (d, 1H, J=6.2 Hz), 7.55 (d, 1H, J=5.9 Hz). LCMS (ESI) calc'd for [C$_6$H$_4$ClN$_2$Se]$^+$ ([M+H]$^-$): m/z 218.9. found 216.9.

The selenadiazole (157 mg, 0.726 mmol) from the previous step was dissolved in conc. $H_2SO_4$ (2.4 mL) and cooled in an ice water bath. The dark green solution was treated dropwise with conc. $HNO_3$ (0.16 mL) and turned dark red in color. After 50 min, the reaction mixture was poured onto ice and filtered via vacuum filtration to yield the nitrated selenadiazole product as a light brown powder (145 mg, 77% yield). The crude product was carried forward to the next step without further purification: $^1H$ NMR (400 MHz, DMSO-$d_6$) δ 8.13 (d, 1H, J=7.6 Hz), 7.82 (d, 1H, J=7.6 Hz). LCMS (ESI) calc'd for $[C_6H_3ClN_3O_2Se]^+$ $([M+H]^+)$: m/z 263.5. found 263.5.

The nitroselenadiazole (83.54 mg, 0.321 mmol) from the previous step was dissolved in conc. HCl (0.78 mL) and cooled in an ice bath. The reaction mixture was treated with a 48% HI solution (0.26 mL) followed by 50% NaOH to obtain a pH of 8. The product was extracted with ethyl acetate. The organic layer was washed with brine and concentrated under reduced pressure to provide S2 as a red powder (45.7 mg, 76%): $^1H$ NMR (400 MHz, Acetone-$d_6$) δ 6.78 (d, 1H, J=8.2 Hz), 6.68 (d, 1H, 8.2 Hz), 5.33 (bs, 2H), 5.18 (bs, 2H). LCMS (ESI) calc'd for $[C_6H_7ClN_3O_2]^+$ $([M+H]^+)$: m/z 188.0. found 188.0.

Step 2;

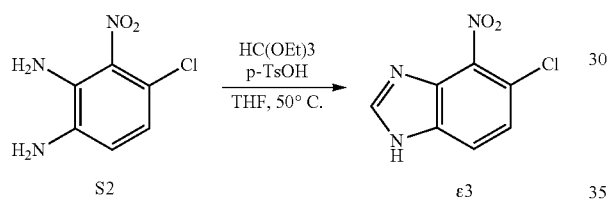

S3 was prepared analogously to a literature procedure (Valdez, J.; Cedillo, R.; Henandez-Campos, A.; Yepez, L.; Hernandez-Luis, F.; Navarrete-Vazquez, G.; Tapia, A.; Cortes, R.; Hernandez, M.; Castillo, R. *Bioorg. Med. Chem. Lett.* 2002, 12, 2221-2224): A solution of S2 (75 mg, 0.40 mmol) in THF (1.5 mL) was treated sequentially with triethyl orthoformate (178 mg, 1.2 mmol) and p-toluenesulfonic acid (7.6 mg, 200 µL, 0.04 mmol). The reaction mixture was stirred at 50° C., the reaction was monitored by LCMS. After 2 h, the solvent was removed under a stream of nitrogen gas, and the resulting residue was partitioned between ethyl acetate and water. The organic layer was washed with saturated aqueous $Na_2CO_3$, dried over $MgSO_4$, and concentrated under reduced pressure to provide S3 as a light brown solid (57 mg, 72%): $^1H$ NMR (400 MHz, Acetone-$d_6$) δ 8.42 (s, 1H), 8.03 (d, 1H, J=8.2 Hz), 7.87 (d, 1H, J=8.2 Hz), 7.48 (bs, 1H). LCMS (ESI) calc'd for $[C_7H_5ClN_3O_2]^-$ $([M-H]^-)$: m/z 198.0. found 198.0.

Step 3:

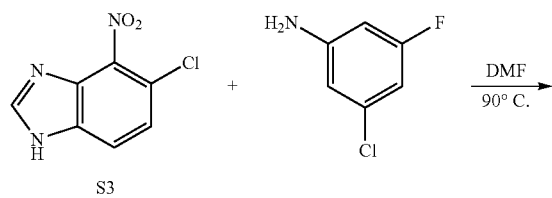

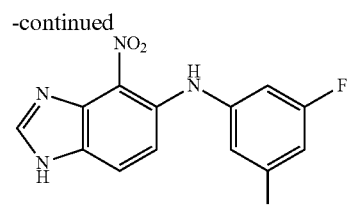

Compound 35

Compound 35 was prepared following the procedure described above for compound 1 using 6-chloro-7-nitro-1H-benzo[d]imidazole (S3) in place of 5-chloro-4-nitrobenzo[c][1,2,5]oxadiazole. In this example, purification by flash chromatography on silica gel (15% ethyl acetate in hexanes) provided the desired compound 35 as a yellow solid (9.4 mg, 31%): $^1H$ NMR (400 MHz, Acetone-$d_6$) δ 8.37 (d, 1H, J=8.8 Hz), 8.01 (s, 1H), 7.72 (d, 1H, J=8.8 Hz), 6.51 (dd, 1H, J=1.8 Hz, 1.8 Hz), 6.34 (m, 2H). $^{13}C$ NMR (100 MHz, Acetone-$d_6$) δ 164.8 (d, J=241.6 Hz), 152.3 (d, J=12.8 Hz), 142.6, 139.5, 135.7, 135.6 (d, J=14.0 Hz), 129.9, 128.0, 127.1, 125.2, 118.6, 103.9 (d, 25.8 Hz), 100.0 (d, 24.5 Hz). LCMS (ESI) calc'd for $[C_{13}H_7ClFN_4O]^-$ $([M-H]^-)$: m/z 305.0. found 305.0.

Example 7

Synthesis of Compound 36

Step 1:

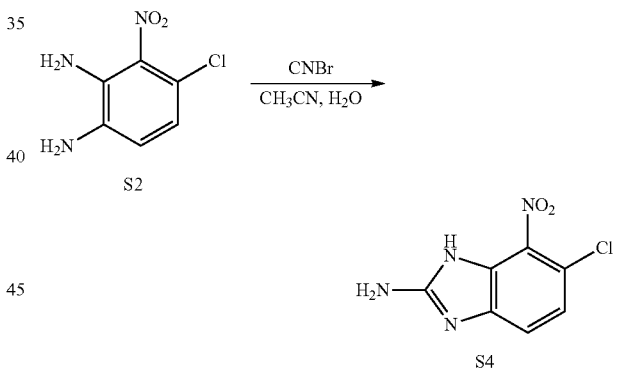

S4 was prepared analogously to a literature procedure (Valdez, J.; Cedillo, R.; Henandez-Campos, A.; Yepez, L.; Hernandez-Luis, F.; Navarrete-Vazquez, G.; Tapia, A.; Cortes, R.; Hernandez, M.; Castillo, R. *Bioorg. Med. Chem. Lett.* 2002, 12, 2221-2224): S2 (75 mg, 0.40 mmol) was dissolved in a 5:1 mixture of $CH_3CN$ and water (1.2 mL) and cooled to 0° C. The dark red solution was treated with cyanogen bromide (47 mg, 0.44 mmol), and the reaction was monitored by LCMS. At the completion of the reaction, the solvent was removed under a stream of nitrogen gas. Conc. ammonium hydroxide was added, which resulted in a dark red precipitate formation that was filtered via vacuum filtration. The precipitate was washed repeatedly with cold water and dried under vacuum. Purification via flash chromatography on silica gel (15% ethyl acetate in hexanes) provided the desired product S4 as a red powder (35.0 mg, 41%): $^1H$ NMR (CDCl$_3$, 400 MHz) δ 6.82 (bs, 2H), 6.78 (d, 1H, J=8.2 Hz), 6.68 (d, 1H, J=8.2 Hz), 5.33 (bs, 1H). LCMS (ESI) calc'd for [C$_7$H$_4$ClN$_4$O$_2$]$^-$ ([M−H]$^-$): m/z 211.0. found 211.0.

Step 2:

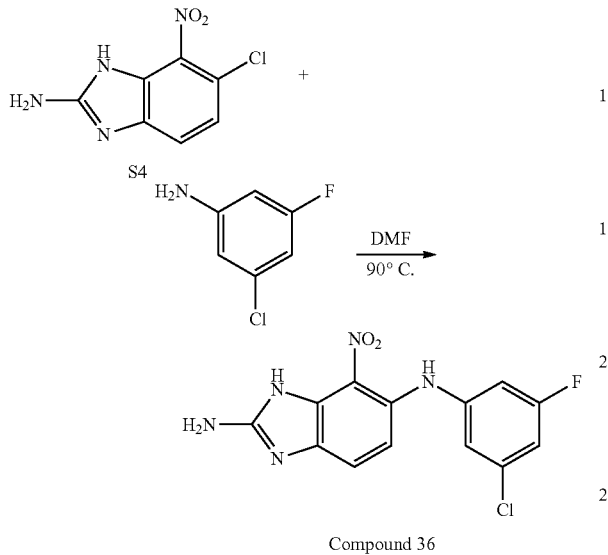

Compound 36

Compound 36 was prepared analogously to compound 1 using 6-chloro-7-nitro-1H-benzo[d]imidazol-2-amine (S4) in place of 5-chloro-4-nitrobenzo[c][1,2,5]oxadiazole. In this example, purification by flash chromatography on silica gel (20% ethyl acetate in hexanes) provided the desired compound 36 as a yellow solid (19.7 mg, 65%): $^1$H NMR (400 MHz, Acetone-d$_6$) δ 7.32 (d, 1H, J=6.0 Hz), 7.28 (bs, 1H), 6.57 (s, 1H), 6.54 (ddd, 1H, J=1.2, 1.3, 6.7 Hz), 6.40 (ddd, 1H, J=1.3, 1.3, 6.7 Hz), 5.77 (s, 1H). $^{13}$C NMR (100 MHz, Acetone-d$_6$) δ 164.8 (d, J=249.3 Hz), 150.0, 149.8 (d, J=12.1 Hz), 136.1, 136.0, 134.0 (d, J=13.6 Hz), 131.7, 118.8, 118.4 (d, J=1.9 Hz), 110.9, 105.9 (d, J=26.0 Hz), 103.3, 100.3 (d, J=25.6 Hz). LCMS (ESI) calc'd for [C$_{13}$H$_7$ClFN$_4$O]$^-$ ([M−H]$^-$): m/z 305.0. found 305.0.

Example 8

Synthesis of Compound 37

Step 1:

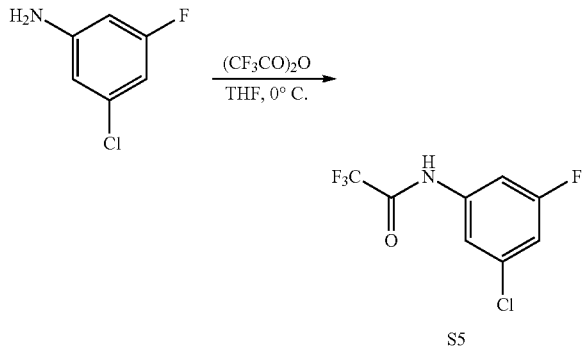

A solution of 3-chloro-5-fluoroaniine (270 mg, 1.8 mmol) in THF (10 mL) was cooled to 0° C. and treated with trifluoroacetic anhydride (770 mg, 3.68 mmol). After 1 h, the solvent was removed under reduced pressure, and the crude oil was dissolved in ethyl acetate. The organic layer was washed with saturated aqueous NaHCO$_3$ (3×), dried over MgSO$_4$ and concentrated under reduced pressure to provide S5 as a white solid (710 mg, 82%): $^1$H NMR (400 MHz, CDCl$_3$) δ 7.92 (bs, 1H), 7.39 (d, 1H, J=12.7 Hz), 7.13 (s, 1H), 6.86 (ddd, 1H, J=8.2, 1.7, 1.7 Hz). $^{13}$C NMR (100 MHz, CDCl$_3$) δ 162.7 (d, J=248.6 Hz), 155.0 (q, J=37.8 Hz), 136.9 (J=11.9 Hz), 135.8 (J=11.9 Hz), 116.8 (q, J=285.0 Hz), 116.3 (d, J=3.5 Hz), 114:1 (d, J=24.7 Hz), 106.5 (d, J=26.5 Hz) LCMS (ESI) calc'd for [C$_8$H$_5$ClF$_4$NO]$^-$ ([M−H]$^-$): m/z 241.0. found 241.0.

Step 2:

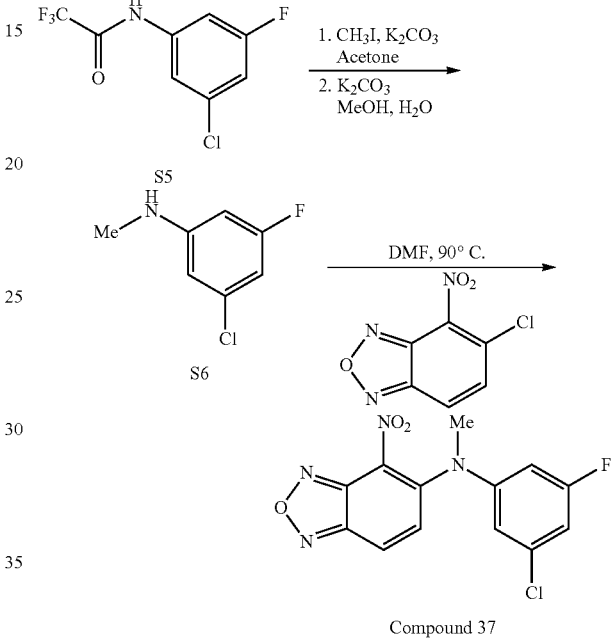

Compound 37

A solution of trifluoroacetamide S5 in anhydrous acetone was sequentially treated with K$_2$CO$_3$ and methyl iodide. The reaction mixture was heated to reflux for 2 h and then filtered by vacuum filtration. The filtrate was concentrated under reduced pressure and dissolved in CH$_2$Cl$_2$. The solution was washed with H$_2$O and brine, dried over MgSO$_4$ and concentrated under reduced pressure to yield a yellow solid (550 mg). The crude material was dissolved in 2:1 MeOH:H$_2$O (3 mL), and treated with potassium carbonate (430 mg, 3.1 mmol). The reaction was stirred for 12 h and then diluted with CH$_2$Cl$_2$. The mixture was washed with H$_2$O and brine, dried over MgSO$_4$ and concentrated under reduced pressure to provide 3-chloro-5-fluoro-N-methylaniline S6 as a clear oil. This oil was dissolved in DMF (1.5 mL) and treated with 5-chloro-4-nitrobenzo[c][1,2,5]oxadiazole (79 mg, 0.39 mmol). After 4 h, the reaction mixture was diluted with ethyl acetate and washed repeatedly with H$_2$O. The organic layer was dried over MgSO$_4$ and concentrated under reduced pressure. The crude material was purified by flash chromatography on silica gel (20% ethyl acetate in hexanes) to provide Compound 37 as an orange solid (129 mg, 85% yield): $^1$H NMR (400 MHz, CDCl$_3$) δ 7.84 (d, 1H, J=9.7 Hz), 7.21 (d, 1H, J=9.8 Hz), 6.96 (m, 2H), 6.80 (d, 1H, J=9.4 Hz), 3.37 (s, 3H) $^{13}$C NMR (100 MHz, CDCl$_3$) δ 163.5 (d, J=250.7), 147.1 (d, J=11.3 Hz), 146.9, 145.3, 137.0 (d, J=12.3 Hz), 131.5, 125.5, 124.5, 121.3 (d, J=11.3 Hz), 119.1 (d, J 3.3 Hz), 114.2 (d, J=22.2 Hz), 108.9 (d, J=24.3 Hz), 42.6. LCMS (ESI) calc'd for [C$_{13}$H$_9$ClFN$_4$O$_3$]$^-$ ([M−H]$^-$): m/z 323.0. found 323.0.

Example 9

Synthesis of Compound 38

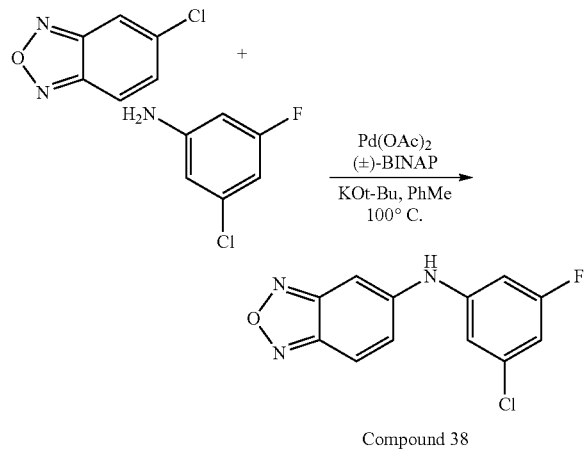

Compound 38

A flame-dried flask was charged with 5-chlorobenzo[c][1,2,5]oxadiazole (100.0 mg, 0.65 mmol, 1 equiv) and toluene (3 mL), and the mixture was stirred at 110° C. for 30 min with a reflux condenser. The solution was cooled to room temperature, and the flask was charged sequentially with palladium (II) acetate (8.8 mg, 0.040 mmol, 6 mol %), racemic 2,2'-bis(diphenylphosphino)-1,1'-binaphthyl (24.9 mg, 0.040 mmol, 6 mol %), 2-chloro-4-fluoroaniline (68.4 µL, 0.65 mmol, 1 equiv) and potassium tert-butoxide (80.0 mg, 0.71 mmol, 1.1 equiv). The mixture was stirred at 90° C. for 12 h, cooled to room temperature, and diluted with water. The mixture was washed with dichloromethane (3×). The combined organic layers were washed with 1N HCl, 1N NaOH, and brine. The organic layers were then dried over MgSO$_4$ and concentrated under reduced pressure. The resulting solid was then recrystallized in hexanes to provide compound 38 as a brown solid (67 mg, 39% yield): $^1$H NMR (400 MHz, Acetone-d$_6$) δ 8.59 (bs, 1H), 7.87 (d, J=9.2 Hz, 1H), 7.40 (dd, J=2.0 Hz, 9.6 Hz, 1H), 7.31 (m, 1H), 7.20 (s, 1H), 7.12 (dt, J=1.3 Hz, 12.0 Hz, 1 Hz), 6.92 (dt, J=2.0 Hz, 8.6 Hz, 1H); $^{13}$C NMR (100 MHz, Acetone-d$_6$) δ 164.4 (d, J=245.3 Hz), 151.1, 147.9, 145.4, 144.9 (d, J=11.9 Hz), 136.3 (d, J=13.2 Hz), 131.0, 118.2, 116.3, 110.6 (d, J=25.5 Hz) 105.9 (d, J=25.0 Hz), 91.7; LCMS (ESI) calc'd for [C$_{12}$H$_6$ClFN$_3$O]$^-$ ([M−H]$^-$): m/z 262.0. found 262.0.

Example 10

Synthesis of Compound 39

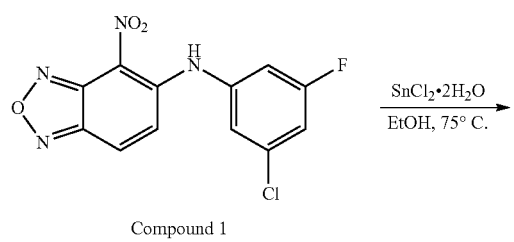

Compound 1

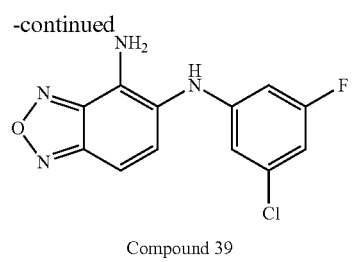

Compound 39

A solution of compound 1 (29 mg, 0.094 mmol) in anhydrous EtOH (2 mL) was treated with SnCl$_2$.2H$_2$O (63 mg, 0.28 mmol, 3 equiv). The reaction was heated to reflux for 4 h and then quenched with saturated aqueous NaHCO$_3$. The mixture was diluted with ethyl acetate passed through a pad of celite. The filtrate was washed with brine, dried over MgSO$_4$, and concentrated under reduced pressure. The crude oil was purified by flash chromatography on silica gel (20% ethyl acetate in hexanes) to provide Compound 39 as an orange powder (18 mg, 70%): $^1$H NMR (600 MHz, CDCl$_3$) δ 7.17 (dd, 2H, J=12, 6 Hz), 6.57 (d, 1H, J=6 Hz), 6.44 (m, 2H), 6.25 (m, 1H), 5.26 (bs, 1H), 4.66 (bs, 2H). $^{13}$C NMR (125 MHz, CDCl$_3$) δ 164.0 (d, J=246.0 Hz), 149.1, 147.0 (d, J=11.3 Hz), 145.4, 136.2 (J=12.9 Hz), 134.2, 130.3, 118.4, 110.6, 107.6 (d, J=25.2 Hz), 107.5 (d, J=27.9 Hz), 105.0. LCMS (ESI) calc'd for [C$_{12}$H$_7$ClFN$_4$O]$^-$ ([M−H]$^-$): m/z 277.7. found 277.1.

Example 11

Synthesis of Compound 40

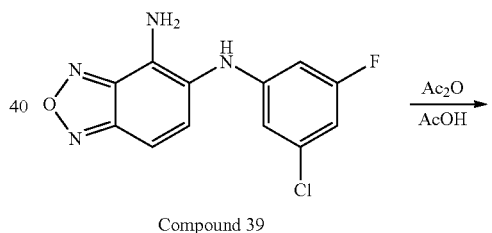

Compound 39

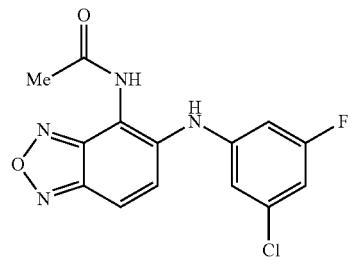

Compound 40

A solution of Compound 39 (15.0 mg, 0.054 mmol) in acetic acid (1 mL) was treated with acetic anhydride (5.5 mg, 0.054 mmol). The reaction was stirred at ambient temperature for 19 h and quenched with ice. The desired Compound 40 was collected by vacuum filtration as a green precipitate (14.0 mg, 81% yield): $^1$H NMR (400 MHz, Acetone-d$_6$) δ 9.54 (bs, 1H), 8.00 (bs, 1H), 7.83 (d, 1H, J=6.4 Hz), 7.66 (d, 1H, J=6.4 Hz), 6.85 (s, 1H), 6.81 (d, 1H, J=5.7 Hz), 6.74 (d, 1H, J=7.1 Hz) 2.25 (s, 3H). $^{13}$C NMR (100 MHz, Acetone-d$_6$) δ 169.5, 163.4 (d, J=240 Hz), 147.9, 145.1 (d, J=11 Hz), 135.3, 135.2, 130.2, 113.6, 113.9, 108.4, 108.2, 103.6, 103.3, 22.3. LCMS (ESI) calc'd for [$C_{14}H_6ClFN_4O_2$]$^-$ ([M-H]$^-$): m/z 319.0. found 319.0.

Example 12

Synthesis of Compound 41

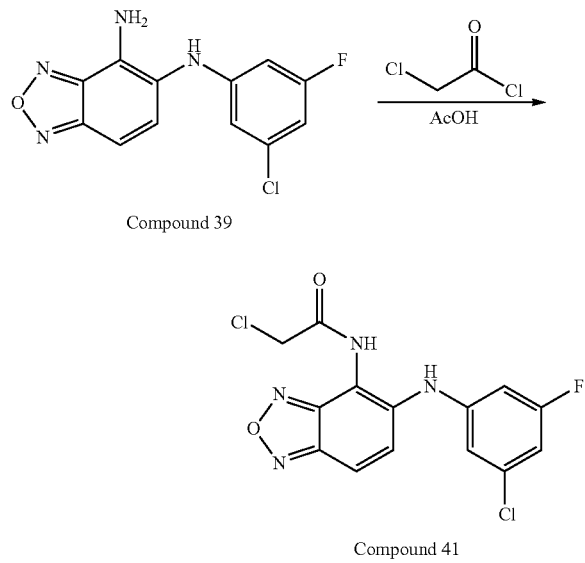

Compound 41

Following the procedure for the synthesis of Compound 40 with chloroacetylchloride, purification by reverse phase HPLC on a C-18 column (10% acetonitrile in water to 90% acetonitrile in water gradient eluent) provided Compound 41 as a green powder. (19.6 mg, 51% yield): $^1$H NMR (400 MHz, Acetone-d$_6$) δ 8.08 (bs, 1H), 7.88 (d, 1H, J=9.6 Hz), 7.68 (d, 1H, J=9.6 Hz), 6.90 (s, 1H), 6.86 (d, 1H, J=8.6 Hz), 6.78 (d, 1H, J=10.6 Hz), 4.39 (s, 2H). $^{13}$C NMR (100 MHz, Acetone-d$_6$) δ 165.8, 164.4 (d, J=244.0 Hz), 147.9, 144.7 (d, J=11.9 Hz), 143.9, 135.2 (d, J=10.2 Hz), 129.9, 115.5, 114.7, 114.5, 108.9 (d, J=24.5 Hz), 104.3 (d, J=25.0 Hz), 95.0, 42.5. LCMS (ESI) calc'd for [$C_{14}H_8Cl_2FN_4O_2$]$^-$ ([M-H]$^-$): m/z 353.0. found 353.0.

Example 13

Synthesis of Compound 42

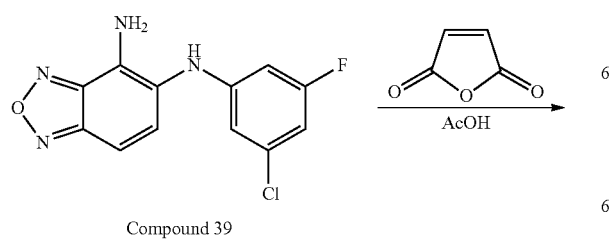

Compound 39

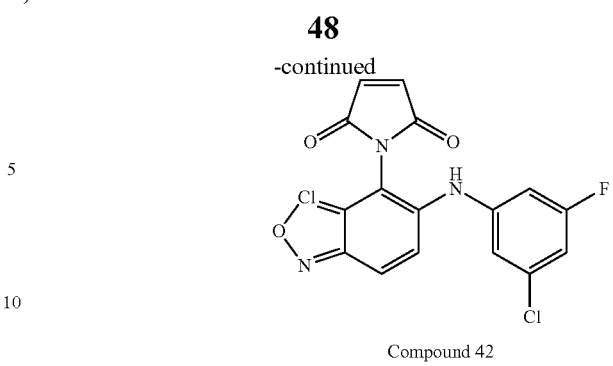

Compound 42

Following the procedure for the synthesis of Compound 40 with maleic anhydride, purification by vacuum filtration provided Compound 42 as a green precipitate (13.4 mg, 69% yield): $^1$H NMR (400 MHz, Acetone-d$_6$) δ 8.42 (bs, 1H), 7.89 (d, 1H, J=6.4 Hz), 7.72 (d, 1H, J=6.4 Hz), 6.93 (s, 1H), 6.81 (m, 3H), 6.39 (d, 1H, J=8.4 Hz). $^{13}$C NMR (100 MHz, Acetone-d$_6$) δ 166.1, 162.8 (d, J=243 Hz), 149.2, 148.8, 145.5, 145.4, 139.3, 136.2 (d, J=13 Hz), 134.5, 133.3, 116.6, 115.7 (d, J=5.8 Hz), 110.0 (d, J=25.6 Hz), 105.4 (d, J=25.3 Hz). LCMS (ESI) calc'd for [$C_{16}H_7ClFN_4O_3$]$^-$ ([M-H]$^-$): m/z 357.0. found 357.0.

Example 14

Synthesis of Compound 43

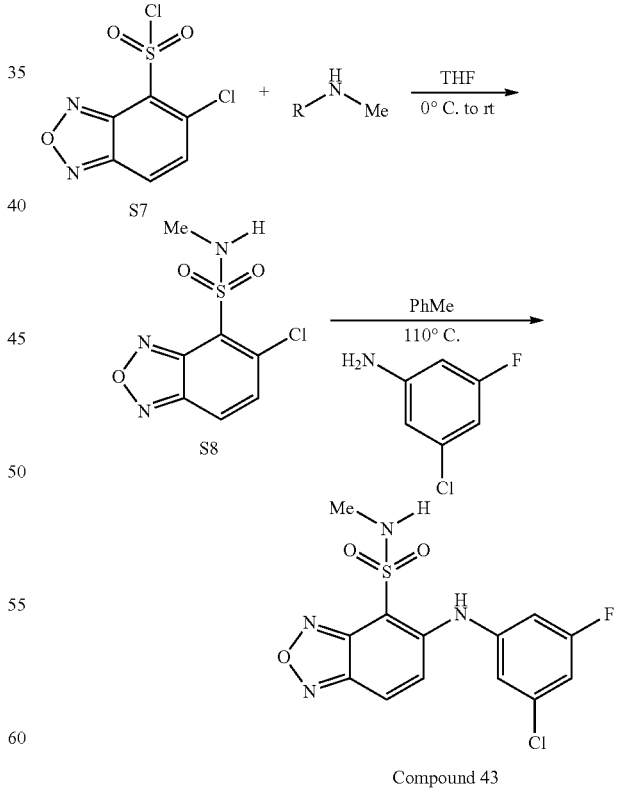

Compound 43

S8: A flame-dried flask containing 5-chlorobenzoxadiazole-4-sulfonyl chloride S7 (400 mg, 1.58 mmol, 1 equiv) was degassed and purged with nitrogen. The flask was charged with THF (4 mL) and cooled to 0° C. Methylamine

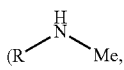

wherein R is hydrogen) (1:1 mL, 2M in MeOH) was added dropwise, and the mixture was stirred for 5.5 h. The reaction was quenched with 0.125 M HCl (4 mL) and extracted with ethyl acetate (3×). The combined organic layers were washed with brine, dried over MgSO$_4$, and concentrated under reduced pressure. The resulting solid was recrystallized in hexanes and dichloromethane to afford 5-chloro-N-methylbenzo[c][1,2,5]oxadiazole-4-sulfonamide S8 as a yellow solid (220 mg, 56% yield).

Compound 43: A flame-dried flask containing secondary sultonamidobenzoxadiazole S8 (215.0 mg, 0.868 mmol, 1 equiv) was degassed and purged with nitrogen. Toluene (26.2 mL), 2-chloro-4-fluoroaniline (0.436 mL, 4.34 mmol, 5 equiv), and N,N-diisopropylethylamine (0.30 mL, 1.74 mmol, 2 equiv) were sequentially added, and the mixture was heated to 110° C. with stirring for 40 h. The reaction was cooled to room temperature and concentrated under reduced pressure. Purification by flash chromatography on silica gel (9:1 hexanes:ethyl acetate with 1% triethylamine) followed by recrystallization in hexanes and dichloromethane provided Compound 43 as a yellow solid (9.6 mg, 31% yield): $^1$H NMR (400 MHz, Acetone-d$_6$) δ 8.05 (d, J=9.8 Hz, 1H), 7.65 (d, J=9.8 Hz, 1H), 7.34 (m, 1H), 7.26 (dt, J=2.2 Hz, 10.0 Hz, 1H), 7.20 (dt, J=2.0 Hz, 8.6 Hz, 1H), 2.71 (s, 3H); $^{13}$C NMR (100 MHz, Acetone-d$_6$) δ 164.1 (d, J=247.0 Hz), 148.0, 147.5, 147.5, 142.6 (d, J=11.8 Hz), 136.4 (d, 12.8 Hz), 128.1, 122.3, 121.3, 121.2, 114.1 (d, J=25.2 Hz), 111.1 (d, J=24.1 Hz), 101.0; LCMS (ESI) calc'd for [C$_{13}$H$_9$ClFN$_4$O$_3$S]$^-$ ([M–H]$^-$): m/z 355.0. found 355.0.

Example 15

Synthesis of Compound 44

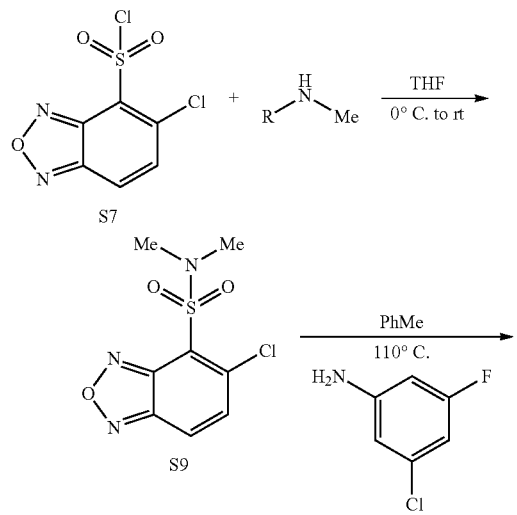

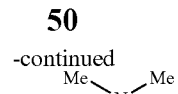

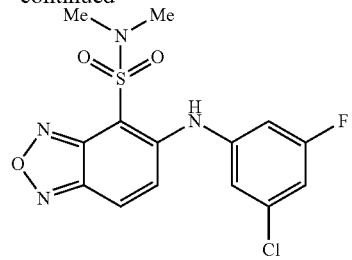

Compound 44

Following the procedure for the synthesis of Compound 43 with dimethylamine

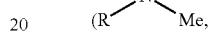

wherein R is methyl), purification by flash chromatography followed by recrystallization provided compound 44 (1.9 mg, 2% yield): $^1$H NMR (400 MHz, Acetone-d$_6$) δ 9.58 (bs, 1H), 8.04 (d, J=9.8 Hz, 1H), 7.62 (d, J=9.8 Hz, 1H), 7.35 (m, 1H), 7.25 (dt, J=2.2 Hz, 7.4 Hz, 1H), 7.19 (dt, J=2.1 Hz, 8.6 Hz. 1H), 2.94 (s, 3H), 1.29 (s, 3H); LCMS (ESI) calc'd for [C$_{14}$H$_{11}$ClFN$_4$O$_3$S]$^-$ ([M–H]$^-$): m/z 369.0. found 369.0.

Example 16

Synthesis of Compound 45

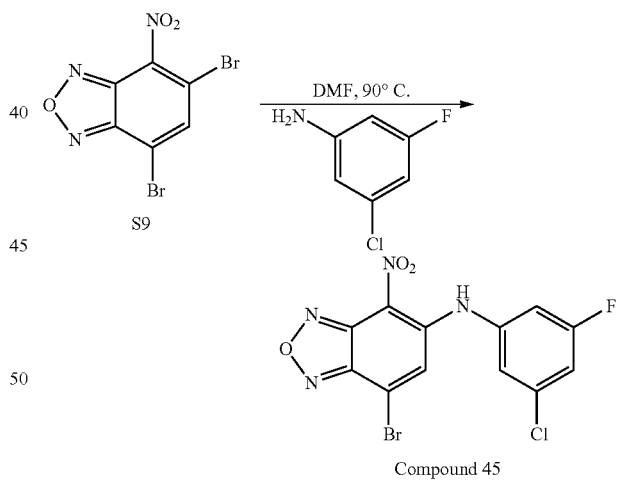

Compound 45

Compound 45 was prepared analogously to the procedure described above for compound 1 using 5,7-dibromo-4-nitrobenzo[c][1,2,5]oxadiazole (S9) (Ghosh, P. B.; Everitt, B. J. *J. Med. Chem.* 1974, 17, 203-206) in place of 5-chloro-4-nitrobenzo[c][1,2,5]oxadiazole.

In this example, recrystallization provided Compound 45 (35 mg, 44% yield): $^1$H NMR (400 MHz, Acetone-d$_6$) δ 7.93 (s, 1H), 7.54 (m, 1H), 7.45 (dt, J=2.2 Hz, 9.4 Hz, 1H), 7.40 (dt, J=2.0 Hz, 8.6 Hz, 1H); $^{13}$C NMR (100 MHz, Acetone-d$_6$) δ 164.0 (d, J=249 Hz), 149.3, 148.2, 145.6, 140.4 (d, J=11 Hz), 136.6 (d, J=12 Hz), 129.3, 124.0, 124.0, 119.1, 116.7 (d, J=25 Hz), 114.0 (d, J=24 Hz); LCMS (ESI) calc'd for [$C_{12}H_4BrClFN_4O_3$]⁻ ([M–H]⁻): m/z 384.9. found 384.9. The desired regioselective formation was confirmed by examining crystals of benzoxadiazole 45 that were suitable for X-ray diffraction.

Example 17

Synthesis of Compound 46

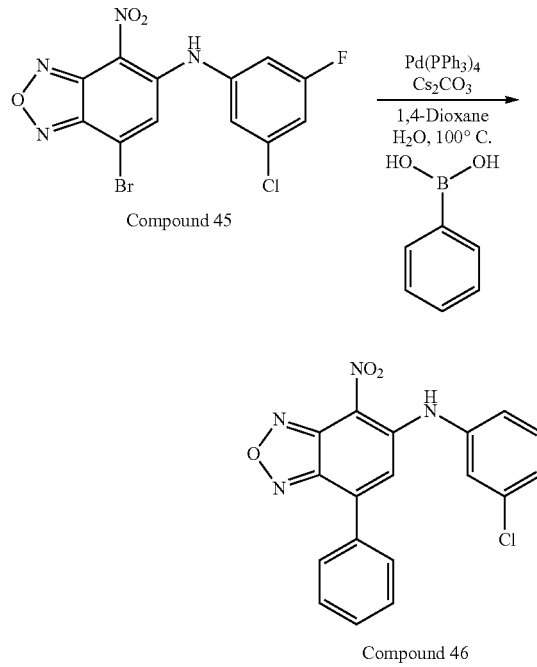

Compound 46

A flame-dried flask containing 7-bromo-N-(3-chloro-5-fluorophenyl)-4-nitrobenzo[c][1,2,5]oxadiazol-5-amine (compound 45) (30 mg, 0.077 mmol, 1 equiv) and phenylboronic acid (9.4 mg, 0.077 mmol, 1 equiv) was degassed and purged with nitrogen. Dioxane (4 mL) was added, and the mixture was stirred at room temperature for 20 minutes. Tetrakis(triphenylphosphine)palladium (14.2 mg, 0.012 mmol, 16 mol %) was quickly added to the reaction vessel, followed by cesium carbonate (31.9 mg, 0.231 mmol, 3 equiv) in 1.16 mL water. The reaction mixture was heated to 100° C. with a reflux condenser and stirred for 3.5 h. After cooling to room temperature, the reaction was diluted in water and extracted with ethyl acetate (3×). The combined organic layers were washed with brine, dried over $Na_2SO_4$ and concentrated under reduced pressure. Recrystallization in hexanes and ethyl acetate afforded compound 46 as a solid (6 mg, 19% yield): $^1$H NMR (400 MHz, Acetone-$d_6$) δ 7.93 (m, 2H), 7.64 (s, 1H), 7.55 (m, 3H), 7.52 (m, 1H), 7.43 (dt, J=2.2 Hz, 9.8 Hz, 1H), 7.1=31 (dt, J=2.1 Hz, 8.6 Hz, 1H); $^{13}$C NMR (100 MHz, Acetone-$d_6$) δ 162.5 (d, J=248 Hz), 147.6, 146.7, 140.9, 138.5, 136.6, 136.5, 134.5, 131.8, 129.1, 123.8, 123.7, 123.2, 123.0, 116.3 (d, J=25 Hz), 113.6 (d, J=24 Hz); LCMS (ESI) calc'd for [$C_{16}H_6ClFN_4O_3$]⁻ ([M–H]⁻): m/z 383.0. found 383.1.

Example 18

Synthesis of (5S,7R)-5-(3-Bromo-5-fluorophenyl)-7-(3-bromophenyl)-4,5,6,7-tetrahydrotetrazolo[1,5-a]pyrimidine (Compound 47) and (5R,7S)-5-(3-bromo-5-fluorophenyl)-7-(3-bromophenyl)-4,5,6,7-tetrahydrotetrazolo[1,5-a]pyrimidine

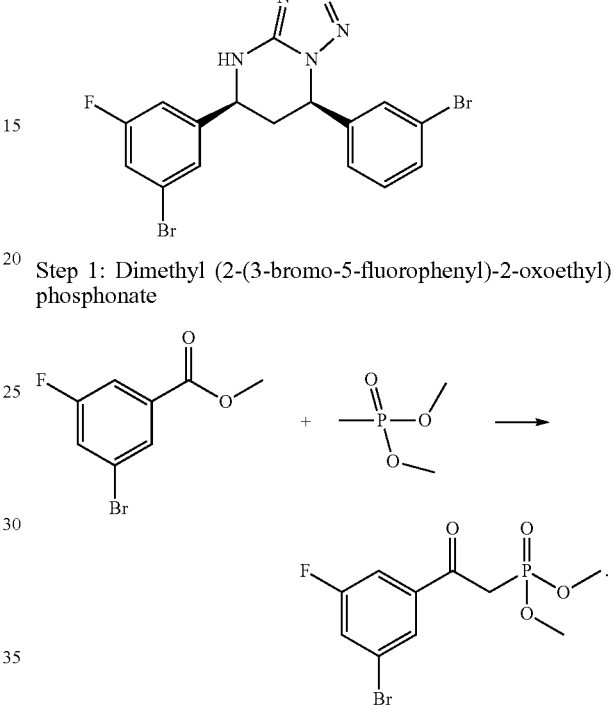

Step 1: Dimethyl (2-(3-bromo-5-fluorophenyl)-2-oxoethyl)phosphonate

Methyl 3-bromo-5-fluorobenzoate (4.9 g, 21.0 mmol) was combined with dimethyl methylphosphonate (2.87 g, 23.1 mmol) in dry THF (35 mL) and cooled to 0° C. A solution of LiHMDS in THF (1.0 M, 43.1 mL, 43.1 mmol) was added slowly over several minutes. The reaction was stirred for 20 minutes at 0° C. and then the mixture was poured into 1N HCl (70 mL) which had been chilled to 0° C. The mixture was diluted with ethyl acetate (100 mL) and separated. The aqueous layer was washed with ethyl acetate and the combined organic layers were washed with water and brine, dried over $Na_2SO_4$, filtered, and then concentrated in vacuo. The yellow residue was chromatographed on $SiO_2$ (Biotage SNAP 100 g) eluting with a gradient of ethyl acetate/hexanes to provide dimethyl (2-(3-bromo-5-fluorophenyl)-2-oxoethyl)phosphonate as a tan solid (6.57 g, 96%).

Step 2: (E)-1-(3-Bromo-5-fluorophenyl)-3-(3-bromophenyl)prop-2-en-1-one

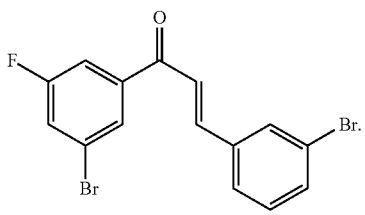

Sodium hydride (0.126 g, 3.14 mmol) was slurried in THF (4 mL) and a solution of dimethyl (2-(3-bromo-5-fluorophenyl)-2-oxoethyl)phosphonate (1.00 g, 3.08 mmol) in THF (6 mL) was added. The mixture was stirred for 15 minutes at ambient temperature; then 3-bromobenzaldehyde (0.36 mL, 3.08 mmol) was added. The mixture was stirred at ambient temperature for 5 hours. The reaction mixture was poured into saturated $NaHCO_3$, diluted with ethyl acetate and separated. The organic layer was washed with brine, dried over $Na_2SO_4$, filtered, and concentrated in vacuo to a pale yellow solid. This solid was triturated with 40% methylene chloride/hexanes then filtered and air-dried. (E)-1-(3-Bromo-5-fluorophenyl)-3-(3-bromophenyl)prop-2-en-1-one was recovered as a pale yellow solid (0.68 g, 58%).

Step 3: 5-(3-Bromo-5-fluorophenyl)-7-(3-bromophenyl)-4,7-dihydrotetrazolo[1,5-a]pyrimidine

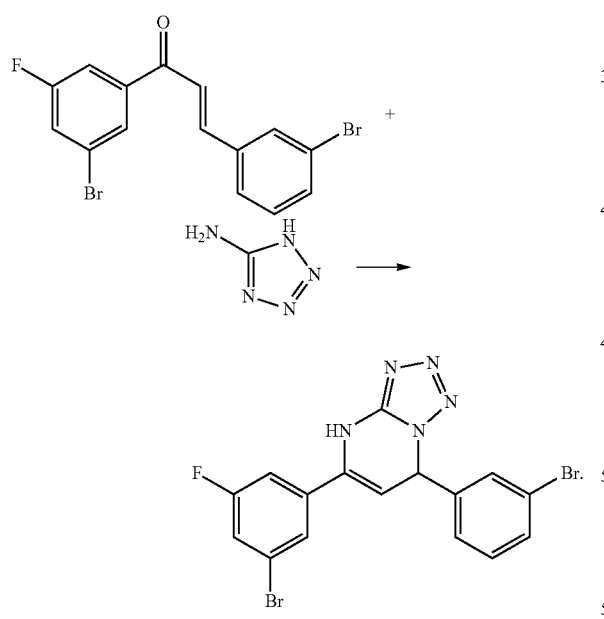

(E)-1-(3-Bromo-5-fluorophenyl)-3-(3-bromophenyl) prop-2-en-1-one (0.68 g, 1.77 mmol) was combined with 1H-1,2,3,4-tetrazol-5-amine monohydrate (0.174 g, 1.69 (00024873) 70 mmol) in DMF (0.7 mL). The mixture was heated to 160° C. in a microwave reactor (Biotage Initiator) for 150 minutes then cooled. The reaction mixture was diluted with methylene chloride (2-3 mL). After stirring overnight, the reaction had developed into a solid mass. This mass was treated with methylene chloride (ca. 4 mL) to suspend the solids. The solids were collected by filtration, washed with a small amount of methylene chloride, and air-dried. 5-(3-Bromo-5-fluorophenyl)-7-(3-bromophenyl)-4,7-dihydrotetrazolo[1,5-a]pyrimidine was recovered as a white solid (78 mg, 10%).

Step 4: 5-(3-Bromo-5-fluorophenyl)-7-(3-bromophenyl)-4,5,6,7-tetrahydrotetrazolo[1,5-a]pyrimidine

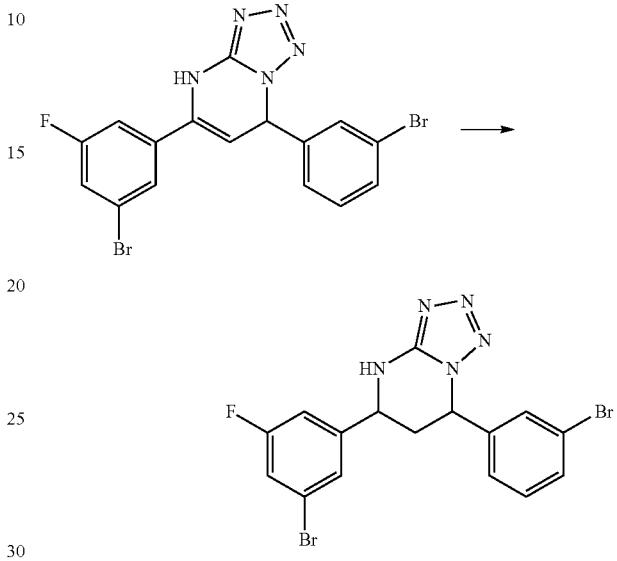

5-(3-Bromo-5-fluorophenyl)-7-(3-bromophenyl)-4H,7H-[1,2,3,4]tetrazolo[1,5-a]pyrimidine (0.089 g, 0.2 mmol) was slurried in MeOH (ca. 3 mL) and sodium borohydride (75 mg, 2 mmol) was added. The mixture evolved gas and was stirred for 3 hours. During this time, the reaction became almost completely homogeneous, then re-developed a white precipitate. The reaction was diluted with water (ca. 9 mL) and stirred for 2 hours, and the solids were collected by filtration, washed twice with $H_2O$, and air-dried. 5-(3-Bromo-5-fluorophenyl)-7-(3-bromophenyl)-4,5,6,7-tetrahydrotetrazolo[1,5-a]pyrimidine was recovered as a white solid (63.5 mg, 71%). LC/MS (ES-API Negative) [M−H⁻] m/z 451.9. $^1$H NMR (DMSO-$d_6$, 400 MHz) δ8.21 (s, 1H), 7.58-7.53 (m, 3H), 7.51-7.47 (m, 1H), 7.40-7.32 (m, 4H), 5.64 (dd, J=4.7, 10.7 Hz, 1H), 4.81 (dd, J=2.0, 10.3 Hz, 1H), 2.43-2.34 (m, 2H).

The individual enantiomers of 5-(3-bromo-5-fluorophenyl)-7-(3-bromophenyl)-4,5,6,7-tetrahydrotetrazolo[1,5-a]pyrimidine were separated by SFC chromatography employing an AD-H column (2×25 cm) and using 30% isopropanol/$CO_2$ (70 mL/min) at 100 bar. The compound was loaded as a solution of 8 mg/mL in methanol. Two peaks were recovered from this chromatography. Absolute stereochemistry of Compound 47 was assigned from co-crystal structural determination of the compound in the HIF-2α PAS-B domain.

The following compounds 48-64 were prepared analogously to the procedures for Compound 47 by using the corresponding reactants and intermediates under appropriate conditions recognizable to one skilled in the art. Only those compounds represented as single enantiomers underwent separation using chiral chromatography.

| Compound No. | Structure |
|---|---|
| 48 | 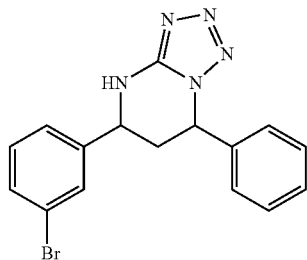 [SMILES: Brc1cccc(C2CC(c3ccccc3)n3nnnc3N2)c1]<br>(+/−)-(cis)-5-(3-bromophenyl)-7-phenyl-4,5,6,7-tetrahydrotetrazolo[1,5-a]pyrimidine |
| 49 | 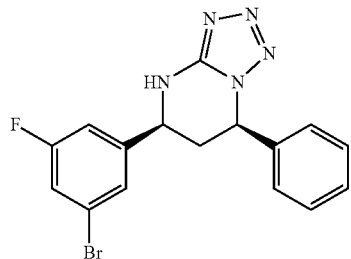 [SMILES: Fc1cc(Br)cc([C@@H]2C[C@H](c3ccccc3)n3nnnc3N2)c1]<br>(5S,7R)-5-(3-bromo-5-fluorophenyl)-7-phenyl-4,5,6,7-tetrahydrotetrazolo[1,5-a]pyrimidine[1] |
| 50 | 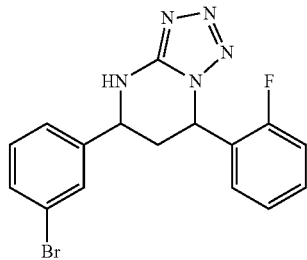 [SMILES: Fc1ccccc1C1CC(c2cccc(Br)c2)Nc2nnnn21]<br>(+/−)-(cis)-5-(3-bromophenyl)-7-(2-fluorophenyl)-4,5,6,7-tetrahydrotetrazolo[1,5-a]pyrimidine |
| 51 | 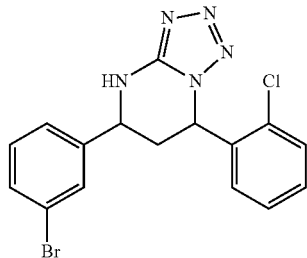 [SMILES: Clc1ccccc1C1CC(c2cccc(Br)c2)Nc2nnnn21]<br>(+/−)-(cis)-5-(3-bromophenyl)-7-(2-chlorophenyl)-4,5,6,7-tetrahydrotetrazolo[1,5-a]pyrimidine |
| 52 | 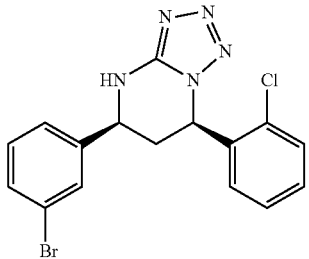 [SMILES: Clc1ccccc1[C@H]1C[C@@H](c2cccc(Br)c2)Nc2nnnn21]<br>(5S,7R)-5-(3-bromophenyl)-7-(2-chlorophenyl)-4,5,6,7-tetrahydrotetrazolo[1,5-a]pyrimidine[1] |
| 53 | 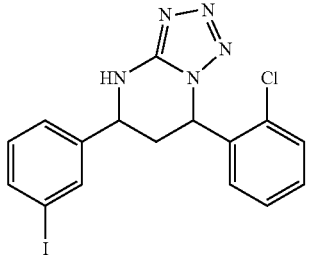 [SMILES: Clc1ccccc1C1CC(c2cccc(I)c2)Nc2nnnn21]<br>(+/−)-(cis)-7-(2-chlorophenyl)-5-(3-iodophenyl)-4,5,6,7-tetrahydrotetrazolo[1,5-a]pyrimidine |
| 54 | 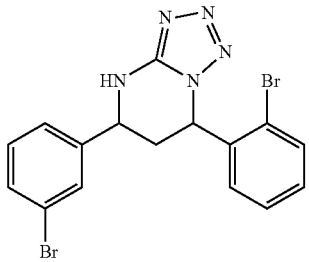 [SMILES: Brc1cccc(C2CC(c3ccccc3Br)n3nnnc3N2)c1]<br>(+/−)-(cis)-7-(2-bromophenyl)-5-(3-bromophenyl)-4,5,6,7-tetrahydrotetrazolo[1,5-a]pyrimidine |
| 55 | 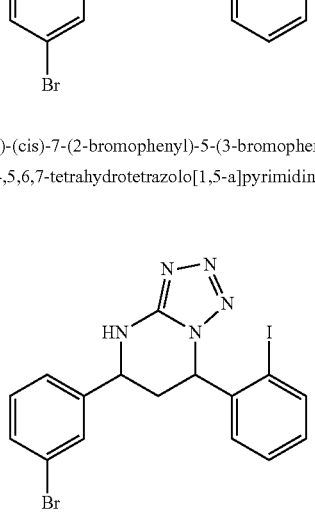<br>(+/−)-(cis)-5-(3-bromophenyl)-7-(2-iodophenyl)-4,5,6,7-tetrahydrotetrazolo[1,5-a]pyrimidine |

| Compound No. | Structure |
|---|---|
| 55 | (+/−)-(cis)-5-(3-bromophenyl)-7-(2-iodophenyl)-4,5,6,7-tetrahydrotetrazolo[1,5-a]pyrimidine |
| 56 | (+/−)-(cis)-5-(3-bromophenyl)-7-(3-chlorophenyl)-4,5,6,7-tetrahydrotetrazolo[1,5-a]pyrimidine |
| 57 | ((5S,7R)-5-(3-bromophenyl)-7-(3-chlorophenyl)-4,5,6,7-tetrahydrotetrazolo[1,5-a]pyrimidine[1] |
| 58 | (5S,7R)-5,7-bis(3-bromophenyl)-4,5,6,7-tetrahydrotetrazolo[1,5-a]pyrimidine |
| 59 | (+/−)-(cis)-5-(3-bromophenyl)-7-(3-chloro-2-fluorophenyl)-4,5,6,7-tetrahydrotetrazolo[1,5-a]pyrimidine |
| 60 | (5S,7R)-7-(5-bromo-2-chlorophenyl)-5-(3-bromophenyl)-4,5,6,7-tetrahydrotetrazolo[1,5-a]pyrimidine[1] |
| 61 | (+/−)-(cis)-5-(3-bromophenyl)-7-(3-chloro-2,6-difluorophenyl)-4,5,6,7-tetrahydrotetrazolo[1,5-a]pyrimidine |
| 62 | (5S,7R)-7-(3-bromo-2,6-difluorophenyl)-5-(3-bromophenyl)-4,5,6,7-tetrahydrotetrazolo[1,5-a]pyrimidine[1] |

| Compound No. | Structure |
|---|---|
| 63 | (5S,7R)-5-(3-bromophenyl)-7-(3,6-dibromo-2-fluorophenyl)-4,5,6,7-tetrahydrotetrazolo[1,5-a]pyrimidine[1] |
| 64 | (+/−)-(cis)-5-(3-bromophenyl)-7-isobutyl-4,5,6,7-tetrahydrotetrazolo[1,5-a]pyrimidine |

[1] Absolute stereochemistry assigned by analogy with (5S,7R)-5,7-bis(3-bromophenyl)-4,5,6,7-tetrahydrotetrazolo[1,5-a]pyrimidine

Example 19

Protein Preparation

HIF-2α PAS-B (240-350), HIF-2α PAS-B* (240-350, R247E), ARNT PAS-B (355-470), and ARNT PAS-B* (355-470, E362R) domains were expressed and purified as previously described (See Scheuermann, T. H. et al. Artificial ligand binding within the HIF-2α PAS-B domain of the HIF2 transcription factor. *Proc Natl Acad Sci USA* 106, 450-455 (2009)). HIF-1α PAS-B (238-349) used for ITC and HIF-2α PAS-B used for NMR studies were expressed with an N-terminal G61 fusion tag and purified by Source-Q ion exchange and Superdex S75 size exclusion chromatography.

AlphaScreen protein reagents were expressed as GST-HIF-2α PAS-B* and His6-G61-ARNT-PAS-B*-FLAG fusions and purified with affinity (glutathione or Ni(II)) and Superdex S75 chromatography, equilibrated in AlphaScreen assay buffer (50 mM Tris (pH 7.5), 100 mM NaCl, 1 mM dithiothreitol), and flash-frozen in liquid N2.

AlphaScreen

The AlphaScreen assay can be done according to the following procedures:
1. Prepare cold binding buffer solution: 20 mM Tris-Cl (pH=7.5), 100 mM NaCl, 1 mM DTT, 0.02% Tween-20 (final concentration) and place on ice to keep temperature approximately 4° C.
2. Prepare Protein Mix: To a 50 mL conical tube add 23 mL of cold buffer and 0.04 mL of both GST-HIF2α PASB* (100 μM) and ARNT-PASB*-Flag (100 μM).
3. Distribute to 96 well plate: Add 60 μL of protein mix to each wells.
4. Adding Compound: Dissolve compounds in DMSO to obtain a final concentration of 10 mM. Then create the appropriate dilutions for your particular compound in glass vials. Once all the dilutions are ready place 1 μL of compound in each well.
5. Prepare Bead mix: In the dark room using green light only create a tube with 3.84 mL of cold buffer and 3 μL of GST Donor beads and Flag acceptor beads.
6. Distribute Bead mix: Invert the tube a couple times before distributing 40 μL of mix to each well.
7. Incubation: After adding beads wrap the plate in tin foil twice and remove the covered plate from dark room. Incubate the plate at room temperature while rocking gently for 4 hours.
8. Read: After 4 hours place the uncovered plate in the plate reader. Make sure the room is relatively free of white light when placing the plate in the machine. It is ok to have the green light on if needed.
9. Beads are obtained from PerkinElmer: PerkinElmer Alphascreen Glutathione Donor Beads (Catalog #6765301) and PerkinElmer AlphaLISA anti-FLAG Acceptor Beads (Catalog # AL112M).
10. Flag acceptor beads should be aliquoted into small opaque tubes (20-50 μl per tube) upon arrival from the manufacturer. Place both sets of beads in 4° C. storage when not in use.
11. Avoid expose beads to white light.
12. Pipette beads up and down several times before adding to a tube of cold buffer solution.
13. Amount of Beads used for Bead mix may vary from batch to batch.

Example 20

Isothermal Titration Calorimetry (ITC)

The following is a general procedure describing the ITC assay Thermodynamic parameters of small molecule binding are determined using a MicroCal VP-ITC calorimeter. Solutions of HIF-2α PAS-B are extensively dialyzed against buffer (50 mM Tris (pH 7.5), 20 mM NaCl and 5 mM beta-mercaptoethanol), which is subsequently used to prepare a matched compound solution by dilution from a 50 mM compound stock in 100% DMSO. ITC data can be collected for some of the certain small molecules by acquiring in 5.0% DMSO to improve compound solubility, while data for some other certain small molecules are collected at ≤0.02% DMSO. Prior controls have demonstrated modest effects of 5% DMSO on measured thermodynamic parameters for HIF/ligand complexes, typically reducing affinities two to four fold. Each isotherm is recorded by injecting 200 μM protein (syringe) into 5-10 μM solutions of compound (cell), accounting for dilution heats by subtracting data from a control titration of 200 μM protein into a matched buffer-DMSO solution. Thermograms are fit to a single site binding model to extract equilibrium binding parameters.

Figure 15A:
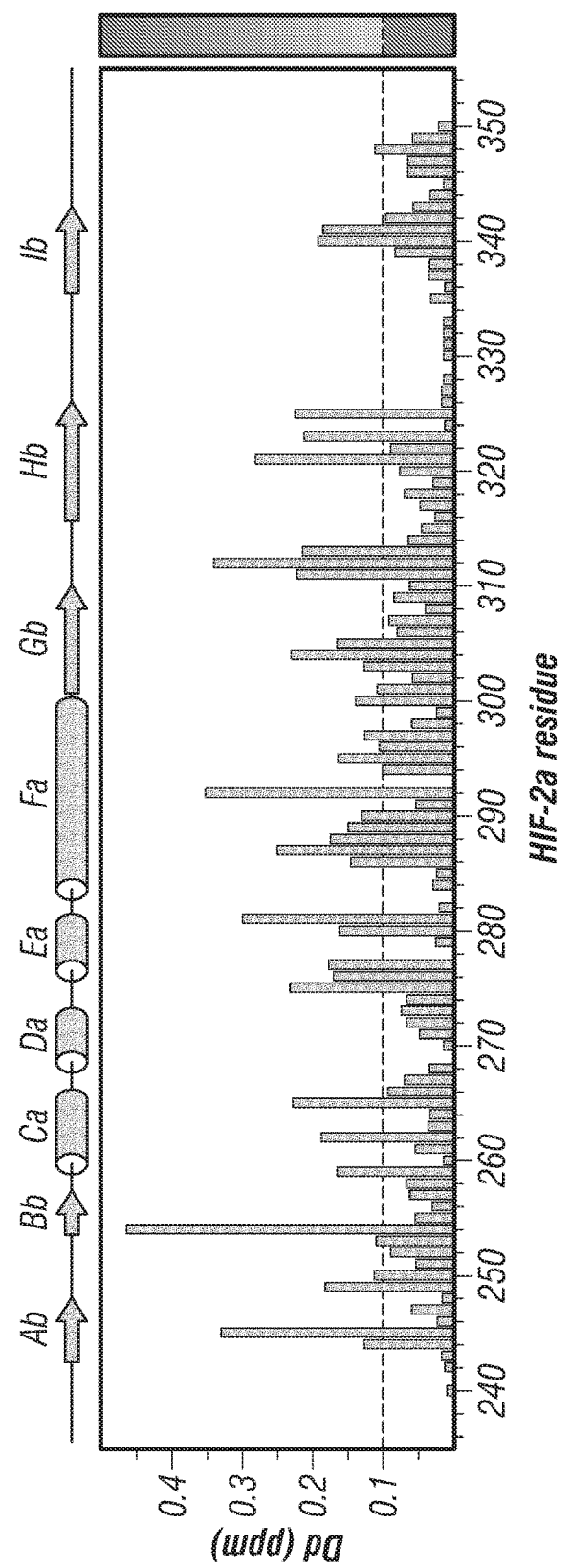

Compounds 1-64 were subjected to AlphaScreen and in some instances ITC analogously to the general procedures described above under appropriate conditions recognizable to one skilled in the art. Table 1 below lists the AlphaScreen $IC_{50}$ data and ITC Kd value with respect to Compounds 1-64. FIG. 15d further shows that ITC measurements of Compound 1 to HIF-2α PAS-B quantitate the binding affinity and 1:1 stoichiometry.

TABLE 1

Assay data for Compounds 1-64

| Compound No. | AlphaScreen IC$_{50}$ (μM) | ITC Kd (μM) |
|---|---|---|
| 1 | 0.1 | 0.08 |
| 2 | 0.33 | 0.5 |
| 3 | >10 | >10 |
| 4 | >30 | 0.52 |
| 5 | 0.18 | 0.16 |
| 6 | 0.46 | 0.64 |
| 7 | 0.15 | 0.22 |
| 8 | 0.76 | 1.1 |
| 9 | 0.09 | 0.26 |
| 10 | 0.43 | 0.37 |
| 11 | >1 | 2.1 |
| 12 | 0.12 | 0.17 |
| 13 | ND | NT |
| 14 | ND | NT |
| 15 | ND | NA |
| 16 | ND | NT |
| 17 | >5 | NT |
| 18 | >10 | NT |
| 19 | >5 | NT |
| 20 | NA | NT |
| 21 | ND | 2 |
| 22 | >30 | NT |
| 23 | >10 | NT |
| 24 | NA | NT |
| 25 | NA | NA |
| 26 | NA | NT |
| 27 | ND | 4.3 |
| 28 | ND | 2.1 |
| 29 | NA | NT |
| 30 | ND | NT |
| 31 | NA | NT |
| 32 | 0.2 | 1.1 |
| 33 | ND | 4.3 |
| 34 | >10 | >20 |
| 35 | >5 | NT |
| 36 | >2 | NT |
| 37 | ND | >10 |
| 38 | NA | ~3 |
| 39 | >30 | ~6 |
| 40 | NA | NT |
| 41 | NA | NT |
| 42 | NA | NT |
| 43 | NA | 5 |
| 44 | NA | 5 |
| 45 | NA | NT |
| 46 | NA | NT |
| 47 | 0.1 | 0.083 |
| 48 | 0.6 | 0.65 |
| 49 | 0.35 | 0.268 |
| 50 | 0.70 | 0.76 |
| 51 | 0.3 | 0.435 |
| 52 | 0.3 | 0.337 |
| 53 | 0.8 | 0.513 |
| 54 | 0.2 | 0.565 |
| 55 | 0.6 | 0.862 |
| 56 | 0.2 | 0.106 |
| 57 | 0.15 | 0.133 |
| 58 | 0.1 | 0.089 |
| 59 | 0.2 | 0.042 |
| 60 | 0.4 | 0.192 |
| 61 | 0.2 | 0.032 |
| 62 | <0.1 | 0.044 |
| 63 | <0.01 | 0.031 |
| 64 | 1 | 0.93 |

ND: Compound disrupts the control;
NA: No activity;
NT: Not tested

Example 21

Co-Crystallography

Compound 1 was co-crystallized as a ternary complex with the HIF-2α/ARNT PAS-B* heterodimer. HIF-2α/ARNT PAS-B* heterodimers were crystallized in the presence of a stoichiometric excess of Compound 1. Ternary complex crystals grew in hanging drops of 2 μl of 300 μM ternary complex and 2 μl of precipitant (100 mM Bis-Tris (pH5.5-6.0), 20 mM NaCl, 19-23% PEG 3350), which was supplemented with 25% PEG400 prior to freezing in liquid nitrogen. X-ray diffraction data were collected at the Advanced Photon Source (Argonne National Laboratory, Argonne, Ill.), beamline ID-19 at 100° K using 0.97937 Å Xrays), which were reduced and scaled with the HKL2000 software package. The structures were determined, refined, and validated using the PHENIX44 macromolecular crystallography software suite (version 1.7.2-869) in conjunction with the PRODRG2 web server to generate initial ligand coordinates, molecular modeling with COOT, validation with MolProbity, and additional analysis and figure preparation in PyMOL (Schrödinger, Inc.). Refinement statistics were presented in Table 2, and coordinates have been submitted with RCSB (PDB code 4GHI). Calculated hydrogen atomic positions were added to protein and ligand coordinate files and employed in a "riding-hydrogen" mode. The final model demonstrates good stereochemical properties, as accessed by Ramachandran (100% favored) and Molprobility (3.17 (98%) clash score and 1.24 (96%) Molprobility scores) analyses.

Figure 15B:
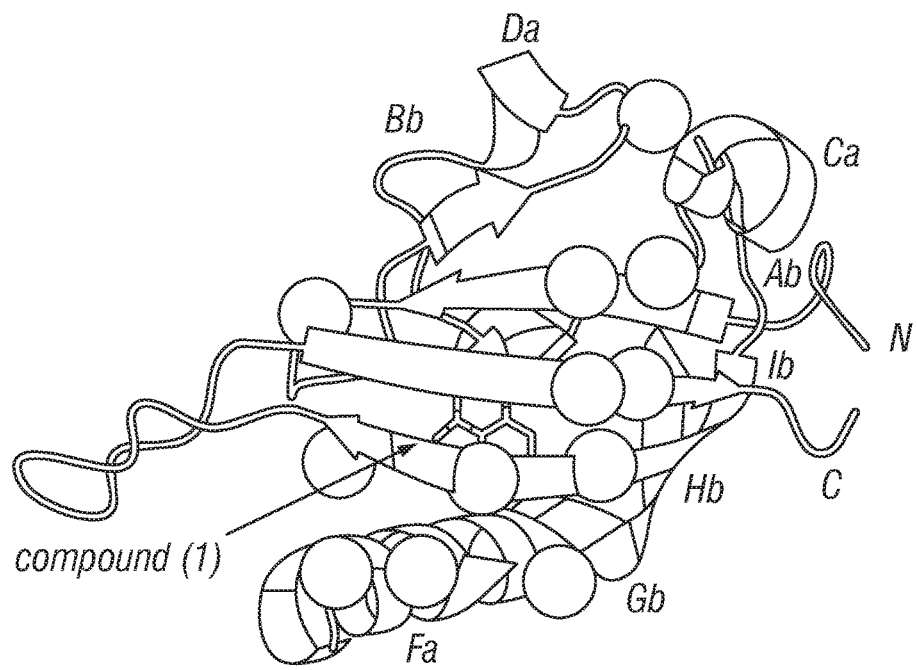

The resulting HIF-2α PAS-B: Compound 1 complex co-crystal is characterized in FIGS. 15(a)-(b).

An $F_o$-$F_o$ electron density difference map (FIG. 16c) was calculated using difference structure factor amplitudes derived from the apo and ligand-bound diffraction data, with phases derived from the atomic coordinates of the apo protein heterodimer (PDB code: 3F1P). Structure factor amplitudes were scaled using SCALEIT, and maps were calculated using FFT, both from CCP4. The homology model of HIF-1α PAS-B (FIGS. 18 a,b) was generated with MODELLER using the ligand-free coordinates of HIF-2α PAS-B (3F1P).

TABLE 2

Data collection and refinement statistics (molecular replacement)
HIF-2 PAS-B*/Compound 1

| Data collection | |
|---|---|
| Space group | C121 |
| Cell dimensions | |
| a, b, c (Å) | 73.35, 83.00, 41.02 |
| α, β, γ (°) | 90.00, 105.98, 90.00 |
| Resolution (Å) | 50.00 (1.5)* |
| $R_{sym}$ or $R_{merge}$ | 0.041 (0.408) |
| I/σI | 30.7 (2.0) |
| Completeness (%) | 99 (89.9) |
| Redundancy | 4.7 (3.7) |
| Refinement | |
| Resolution (A) | 29.02-1.50 |
| No. reflections | 37,409 |
| $R_{work}$/$R_{free}$ | 0.169/0.196 |
| No. atoms (non-hydrogen) | |
| Protein | 1946 |
| Ligand | 21 |
| Water | 184 |
| B-factors | |
| Protein | 20.8 |
| Ligand | 16.1 |
| Water | 35.0 |

TABLE 2-continued

Data collection and refinement statistics (molecular replacement) HIF-2 PAS-B*/Compound 1

| R.m.s. deviations | |
| --- | --- |
| Bond lengths (Å) | 0.011 |
| Bond angles (°) | 1.312 |

*Dataset collected from one crystal.

Example 22

NMR Ligand Binding Assay

Figure 15C:
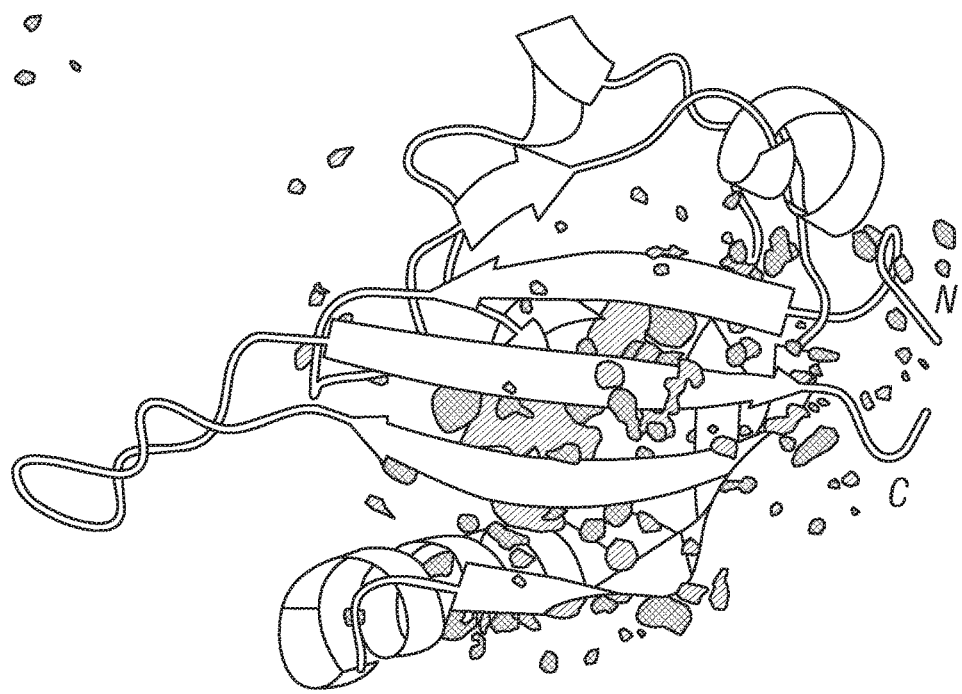

Protein backbone resonance assignments for the HIF-2α PAS-B/Compound 1 complex were determined using HNCO, HNCACB, and CBCA(CO)NH spectra collected on a cryoprobe-equipped Varian Inova 600 MHz spectrometer from a sample of 300 µM U-$^{13}$C, $^{15}$N HIF-2α PAS-B, 350 µM Compound 1 and 0.4% DMSO in 10 mM $d_{11}$-Tris pH 7.3, and 20 mM NaCl buffer using NMRViewJ. Data collected at a second condition (5 mM MES, pH 6.5; 20 mM NaCl) were used to resolve ambiguities stemming from exchange broadening in a limited number of sites. Chemical shift differences (FIG. 15c) were calculated from backbone HIF-2α PAS-B $^{15}$N/$^1$H assignments of the complex and apo form (Erbel et al., PNAS 100(26):15504-9.2003):

$$\Delta\delta = \sqrt{\Delta\delta(^3H)^2 + (0.1 * \Delta\delta^{15}N)^2}$$

Compounds were titrated at 125 and 250 µM concentrations into samples of 200 µM uniformly $^{15}$N-labeled HIF-2α and ARNT PAS-B domains. Significant changes in peak intensity or locations in $^{15}$N/$^1$H HSQC spectra indicated ligand binding. See FIG. 15e.

Example 23

Figure 17A:
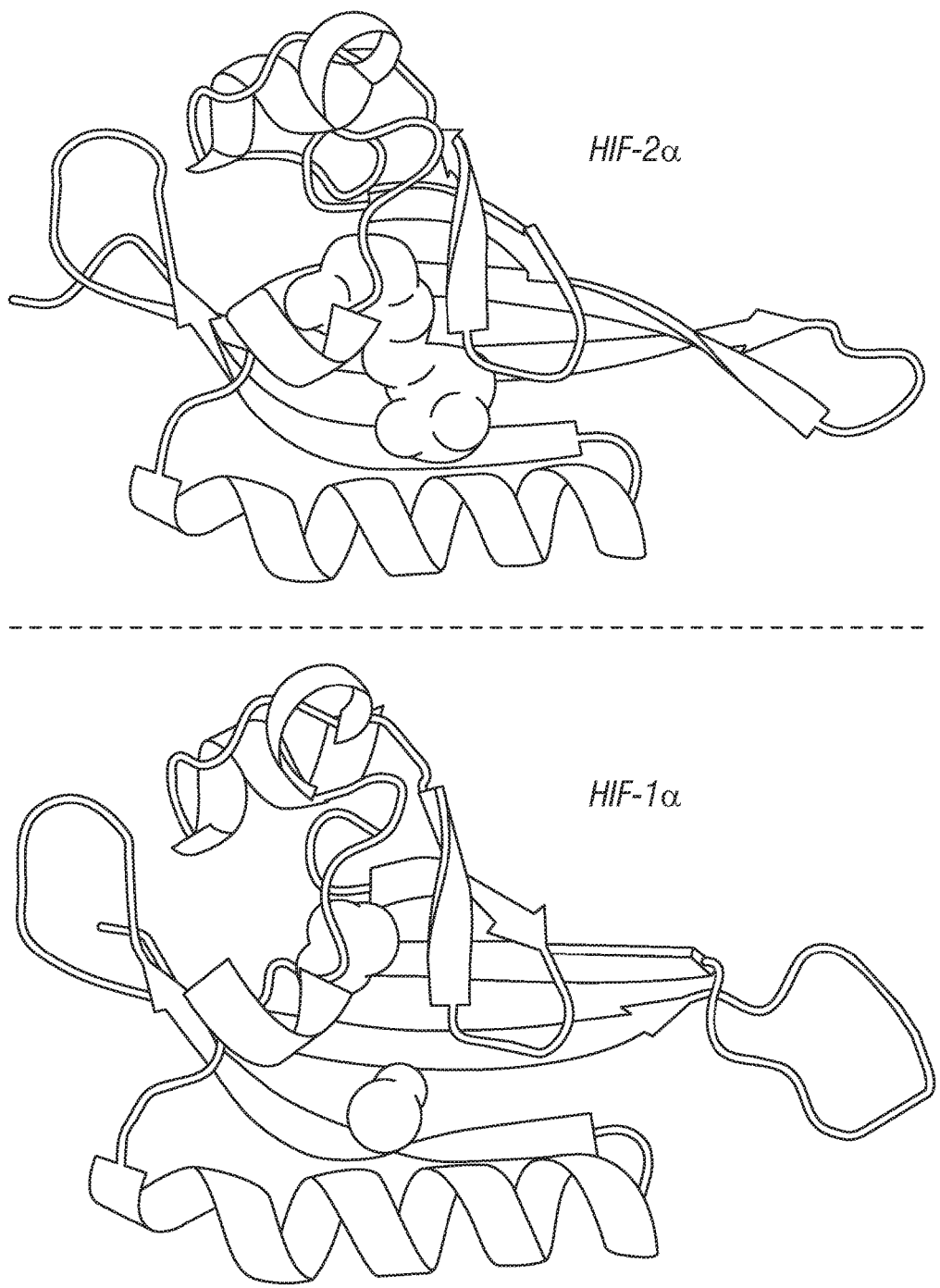
FIG. 17A-C shows that Compound (1) binds selectively to HIF-2α over HIF-1α PAS-B.
Figure 17B:
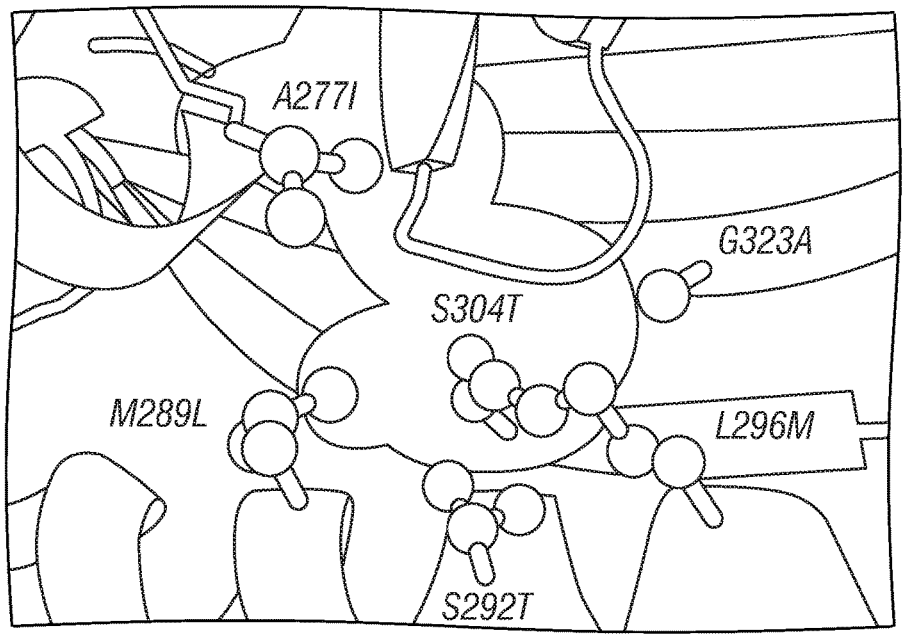
Figure 17C:
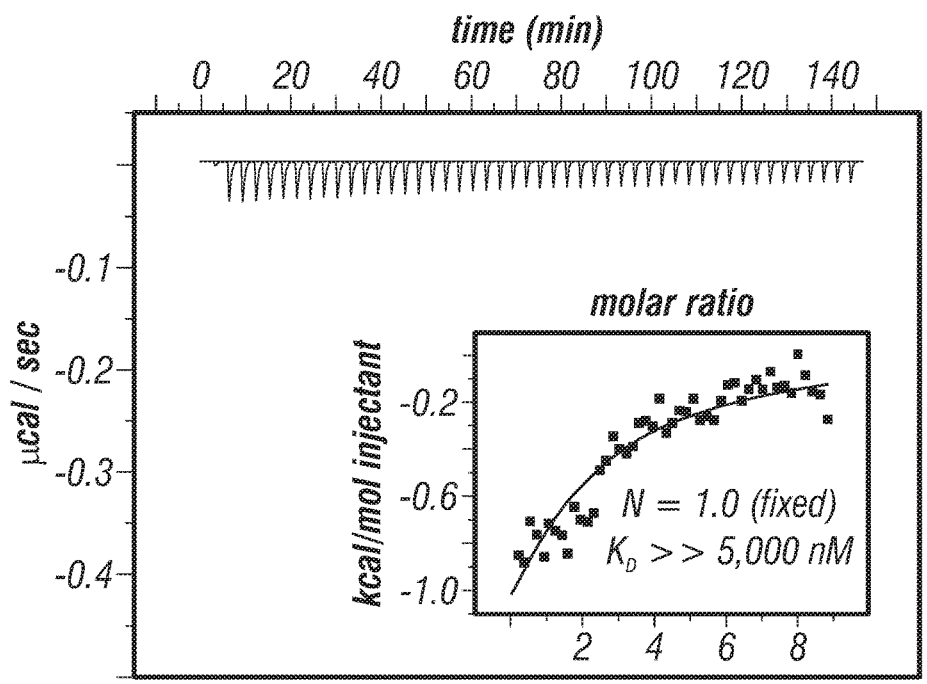

HIF2α Heterodimerization Inhibitor (HIF2-HDI) Selectively Disrupts HIF-2α, but not HIF-1α Heterodimerization To determine whether Compound 1 can inhibit heterodimerization between full length HIF-2α and ARNT polypeptides, nuclear extracts from hypoxic Hep3B cells were prepared. An antibody recognizing the N-terminus of ARNT, was used to immunoprecipitate (IP) the endogenous ARNT protein from the nuclear extracts (FIG. 17 b; top panel). The HIF-2α subunit co-IP'ed with ARNT in extracts incubated with the DMSO vehicle control (FIG. 17b; middle panel). However, addition of Compound 1 to the extracts decreased HIF-2α co-IP efficiency by >2-fold in a dose-dependent manner (FIG. 17b; middle panel). The magnitude of these effects on HIF-2 heterodimerization is similar to that observed following mutation of the HIF-2α PAS-B dimerization interface.

In addition to HIF-2α, Hep3B cells also expressed HIF-1α. Though these two HIF-a isoforms share >70% identity amongst their PAS-B domains, modeling of the HIF-1α PAS-B domain onto the HIF-2α PAS-B structure suggests that several bulkier residues face into the internal HIF-1α cavity (FIG. 18 a,b). Such alterations are expected to constrict the pocket and interfere with ligand binding; this was confirmed by ITC data demonstrating that Compound 1 effectively does not bind to the HIF-1α PAS-B domain (FIG. 18c; KD>>5 µM). The selectivity of Compound 1 for HIF-2α is reflected in FIG. 17 b, as increasing amounts of Compound 1 have little effect on HIF-1 heterodimerization as assessed by Co-IP. These data confirm that in vitro, Compound 1, a certain small molecule disclosed herein, binds selectively within a preformed ligand binding site buried within the HIF-2α PAS-B domain. Ensuing allosteric conformational changes propagate to the surface of the domain, weakening interactions with the ARNT PAS-B domain and disrupting heterodimerization of the full length HIF-2 transcription factor.

Co-IP: Nuclear protein extraction and co-IP experiments were performed as reported in Semenza, G. L. Hypoxia-inducible factors: mediators of cancer progression and targets for cancer therapy. *Trends in pharmacological sciences* 33, 207-214 (2012). The following antibodies were used for immunoblot analysis: anti-HIF-1α mouse monoclonal antibody (BD Biosciences); anti-EPAS/HIF-2α mouse monoclonal antibody (Novus Biological); anti-ARNT/HIF-1β mouse monoclonal antibody (Novus Biological).

Example 24

Figure 5:
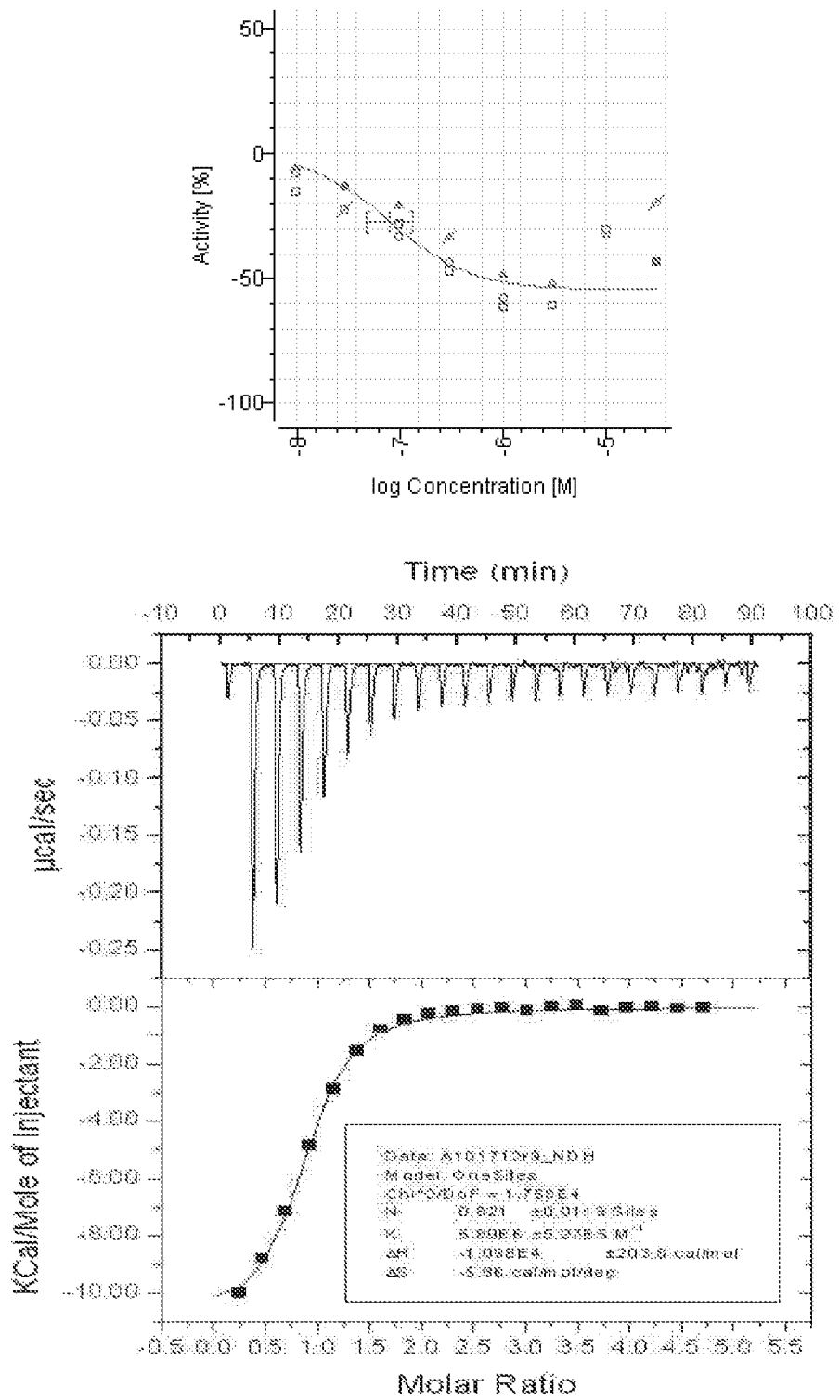
FIG. 5 shows the AlphaScreen Data curve for compound 9, one of the certain small molecules disclosed herein.
Figure 6:
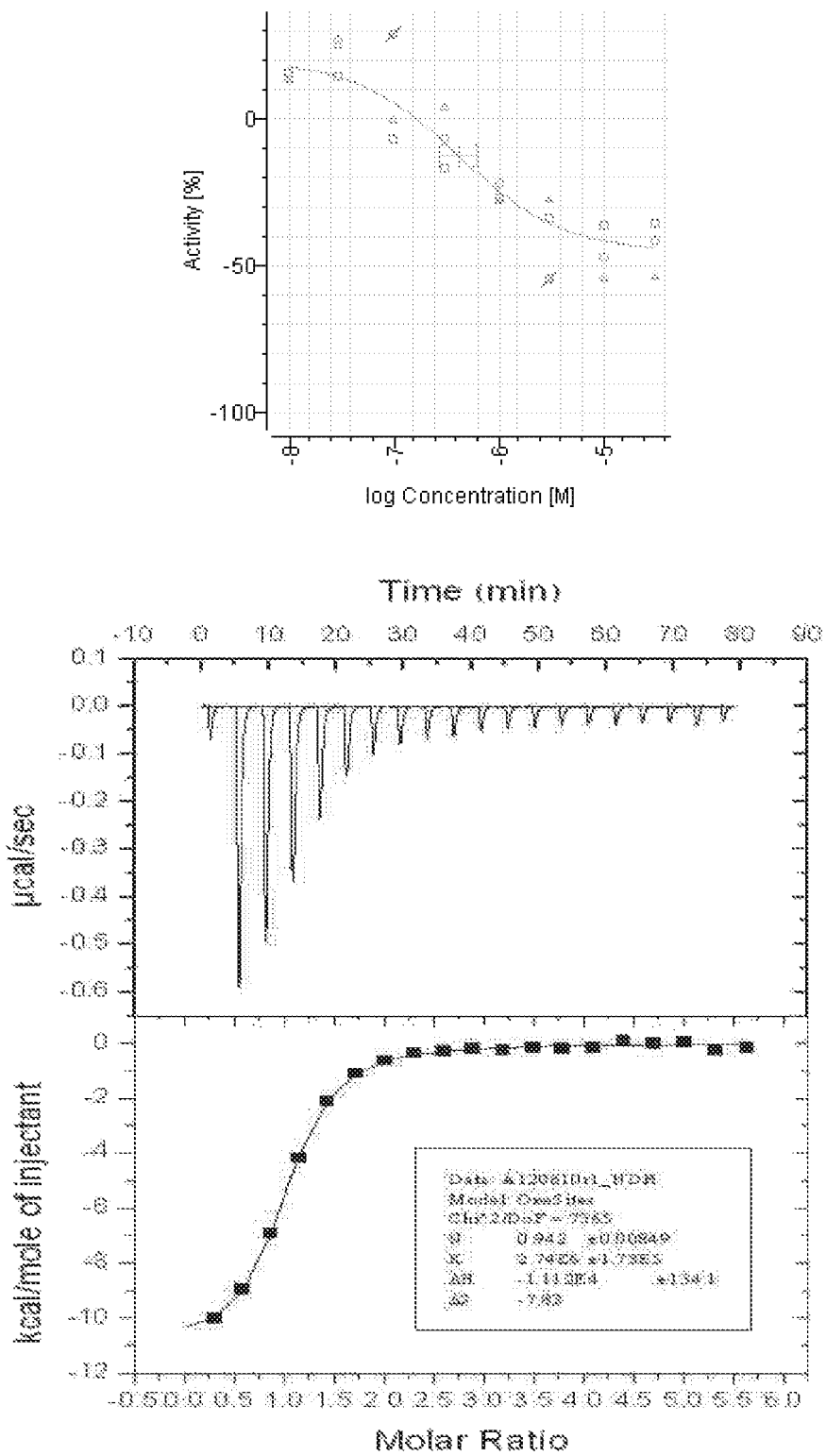
FIG. 6 shows the AlphaScreen Data curve for compound 10, one of the certain small molecules disclosed herein.
Figure 7:
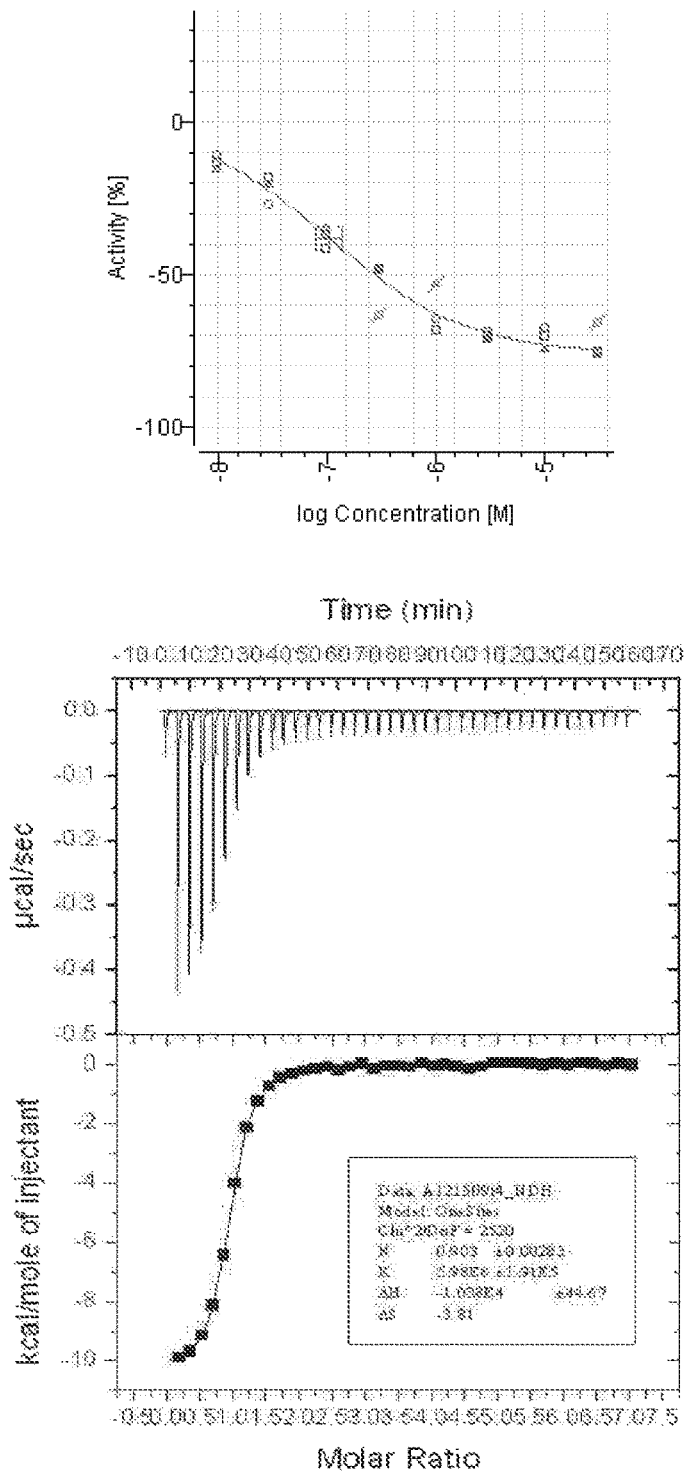
FIG. 7 shows the AlphaScreen Data curve for compound 12, one of the certain small molecules disclosed herein.
Figure 8A:
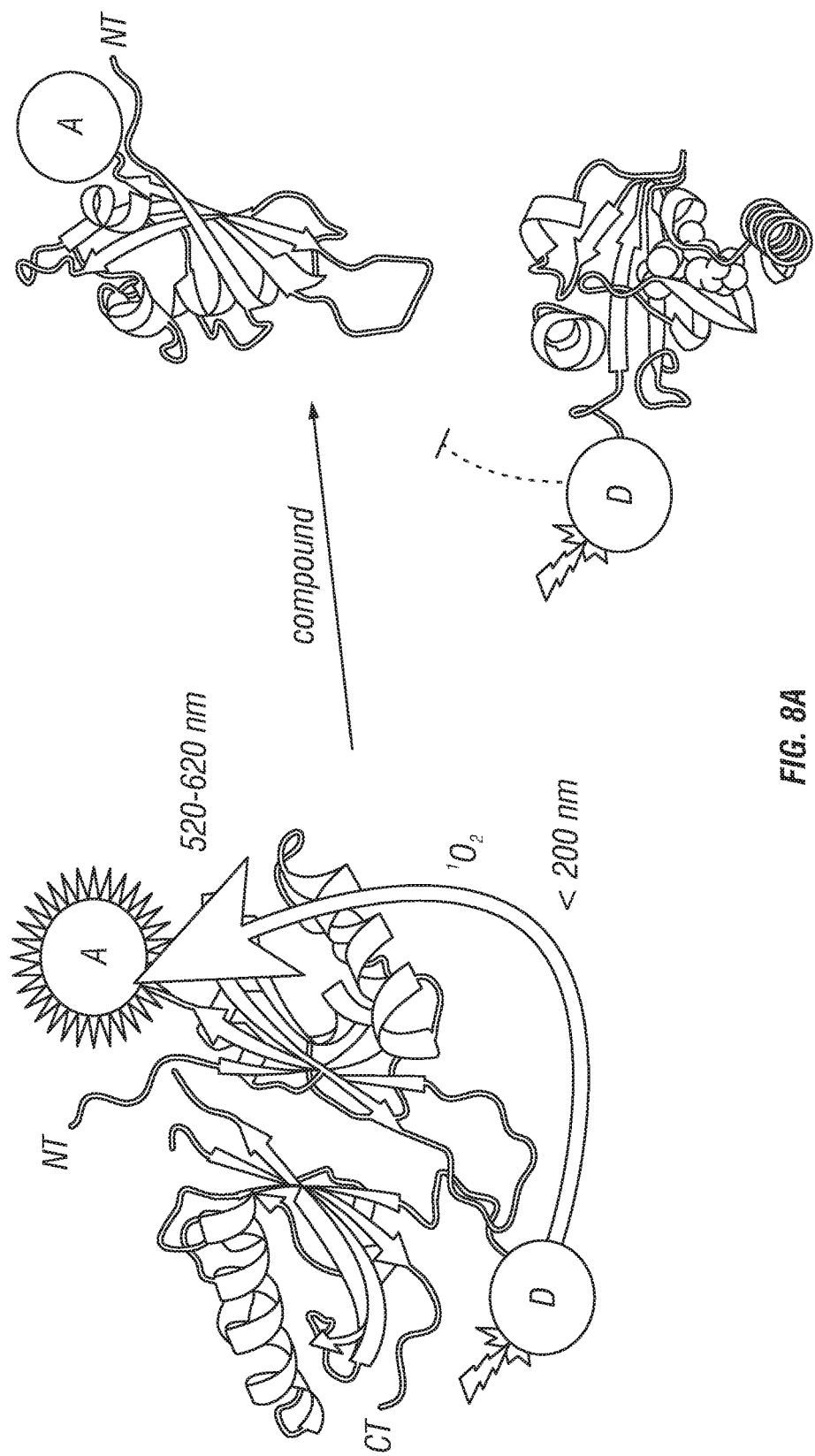
Figure 10A:
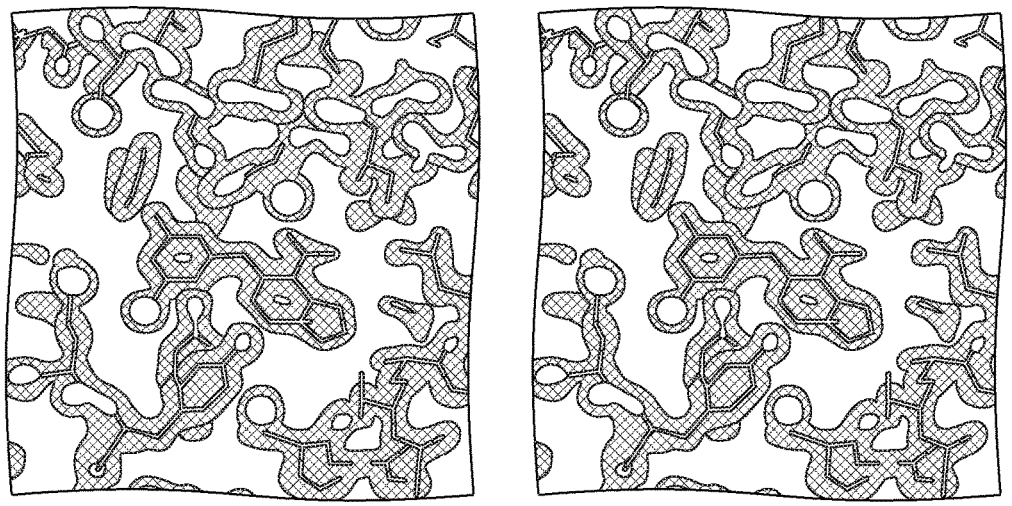
FIG. 10A-B shows examples of electron density used to determine HIF-2α/compound (1), one of the certain small molecules disclosed herein, structure.
Figure 10B:
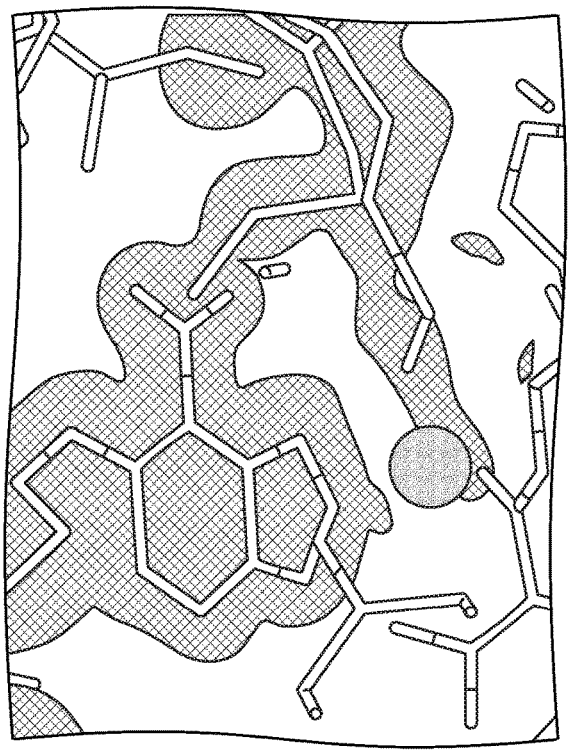
Figure 11A:
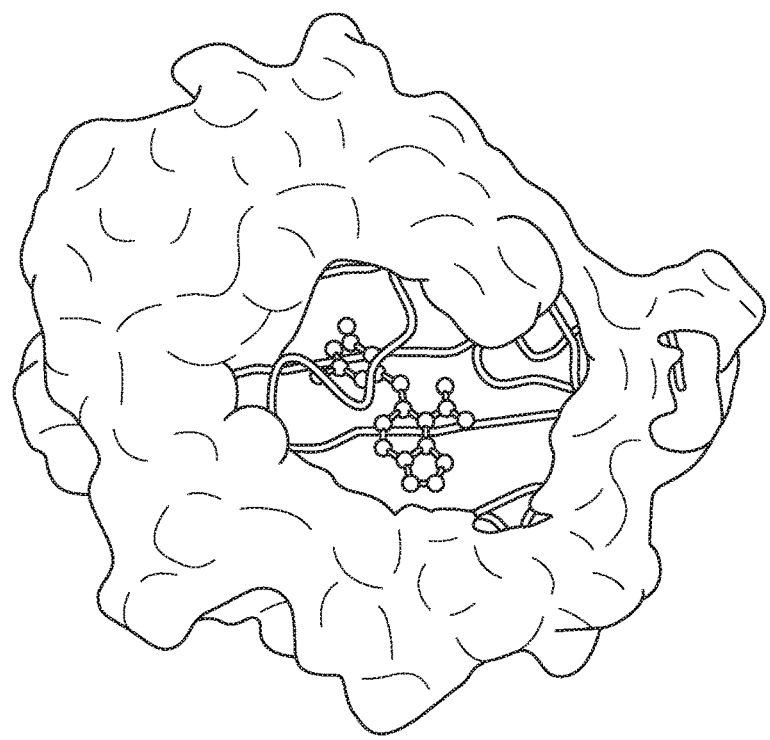
FIG. 11A-D shows that Compound (1) binds within the HIF-2α PAS-B domain similarly to ligands identified by NMR-based screens.
Figure 11B:
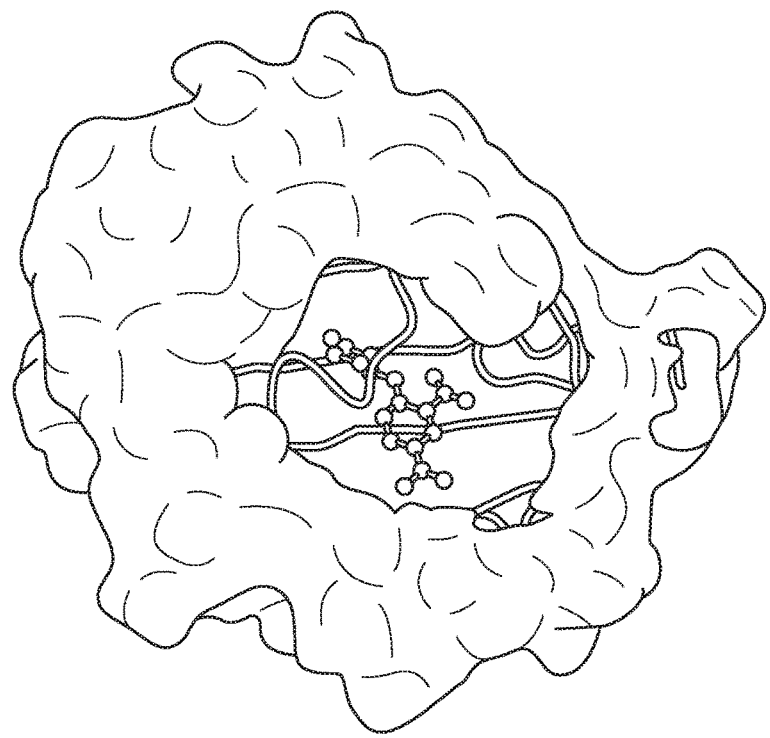
Figure 11C:
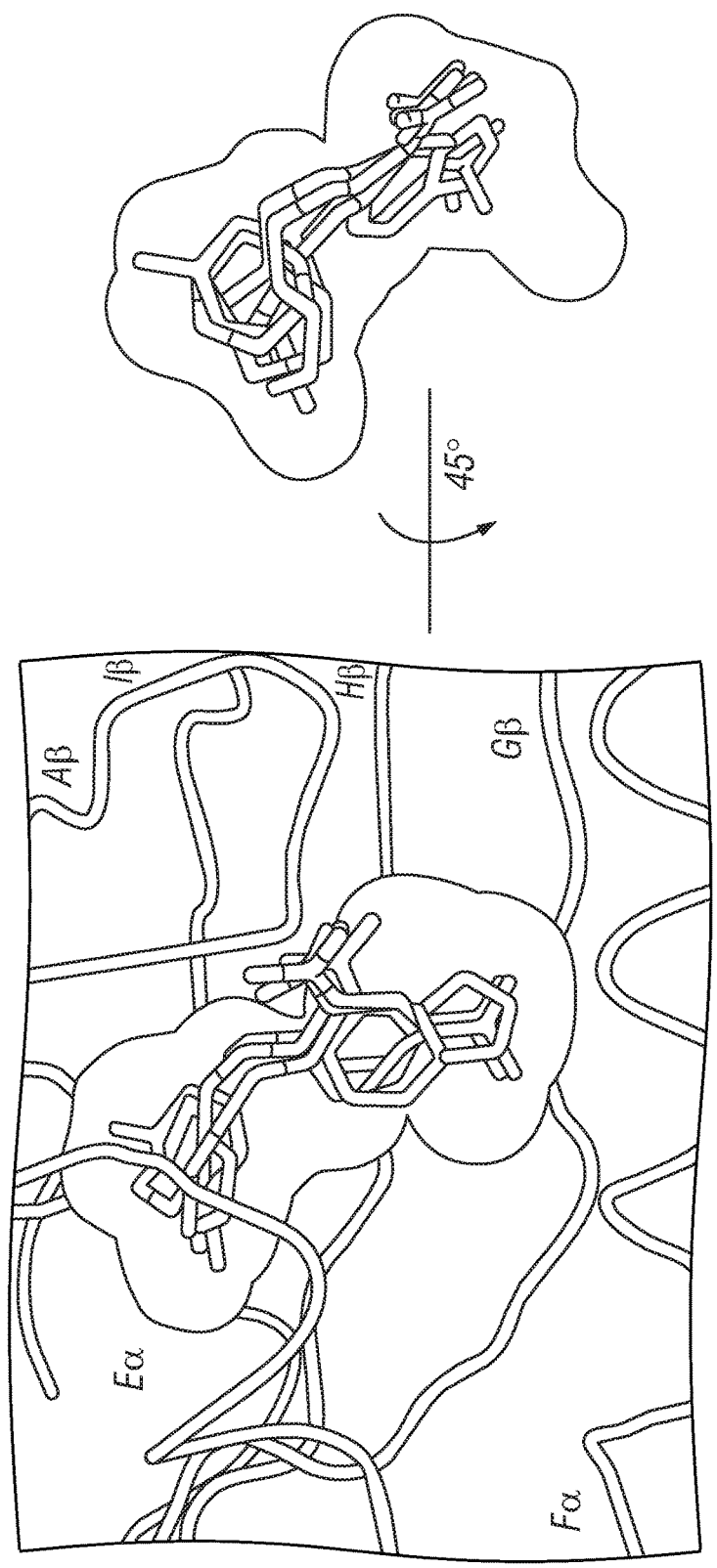
Figure 11D:
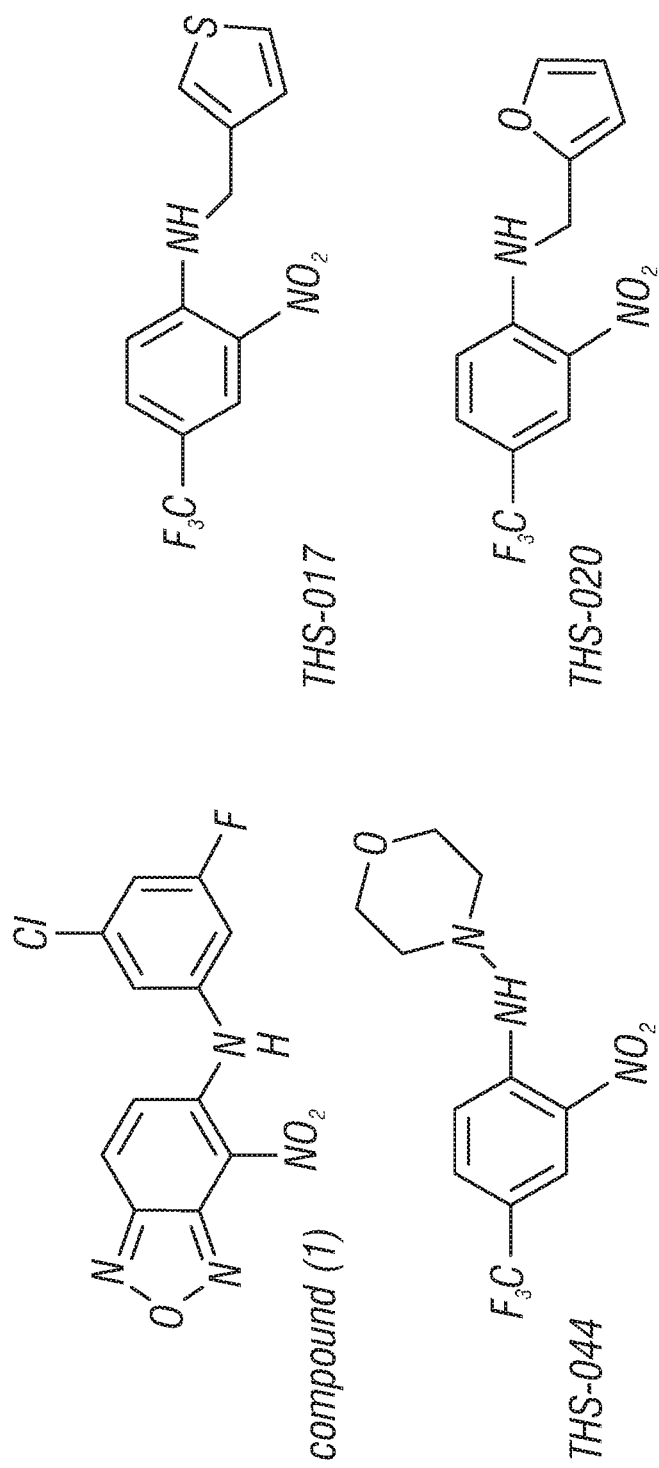
Figure 12:
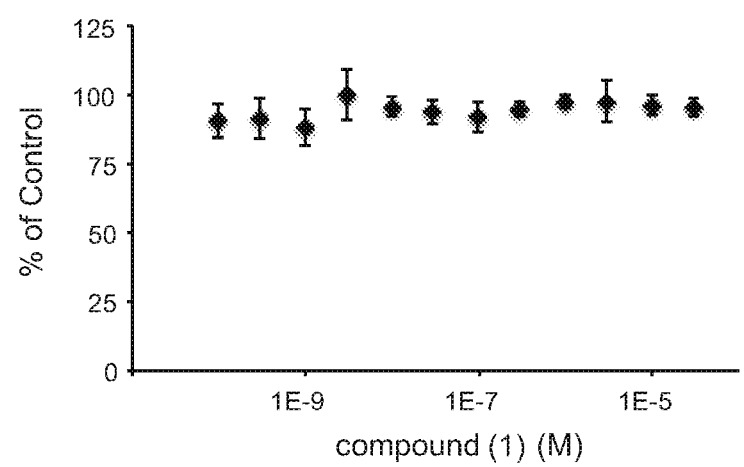
FIG. 12 shows that Compound (1) is not overtly toxic to cultured cells. 786-0 cells were incubated with Compound (1) for 24 hr and ATP levels were measured using Cell Titer Glo as an indicator of cell viability. Assays were performed in triplicates and the error bars represent±SD.
Figure 13:
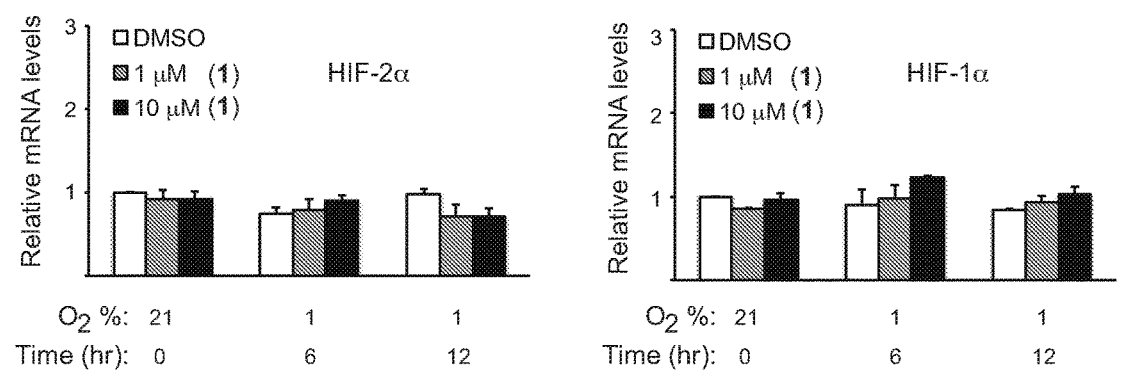
FIG. 13 shows that Compound (1) has no effect on HIF-2α or HIF-1α mRNA levels in Hep3B cells as measured by RT-PCR.
Figure 14A:
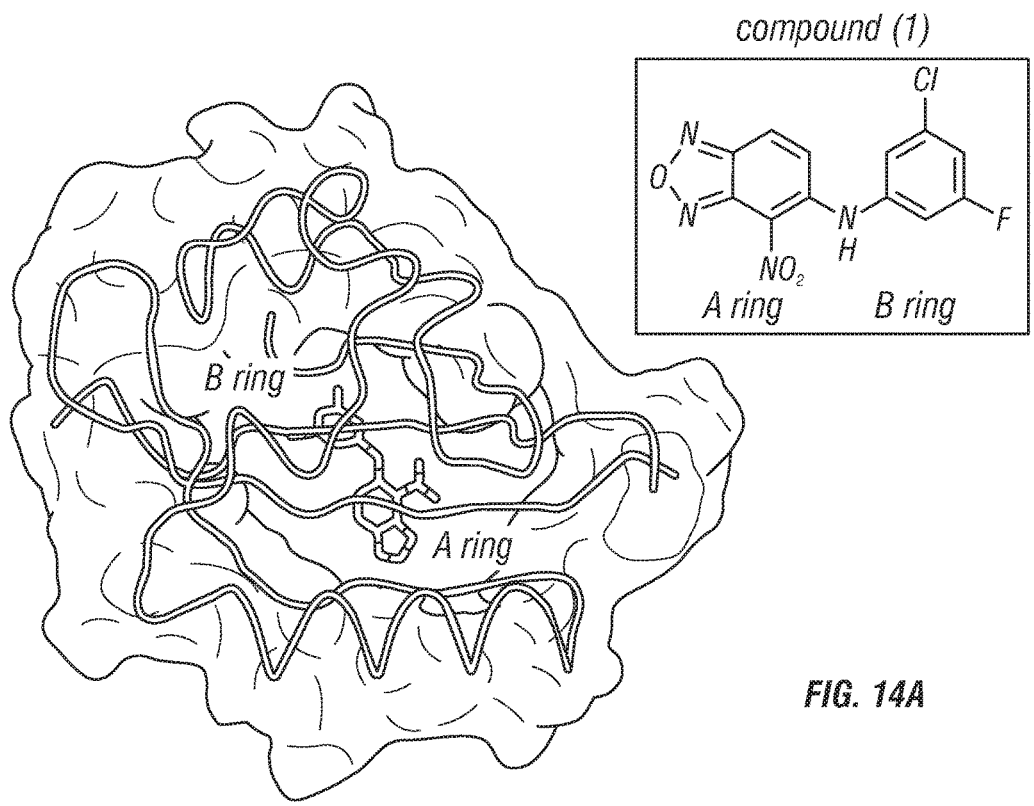
FIG. 14A-D illustrates biophysical characterization of the HIF-2α PAS-B: Compound (1) complex.
Figure 14B:
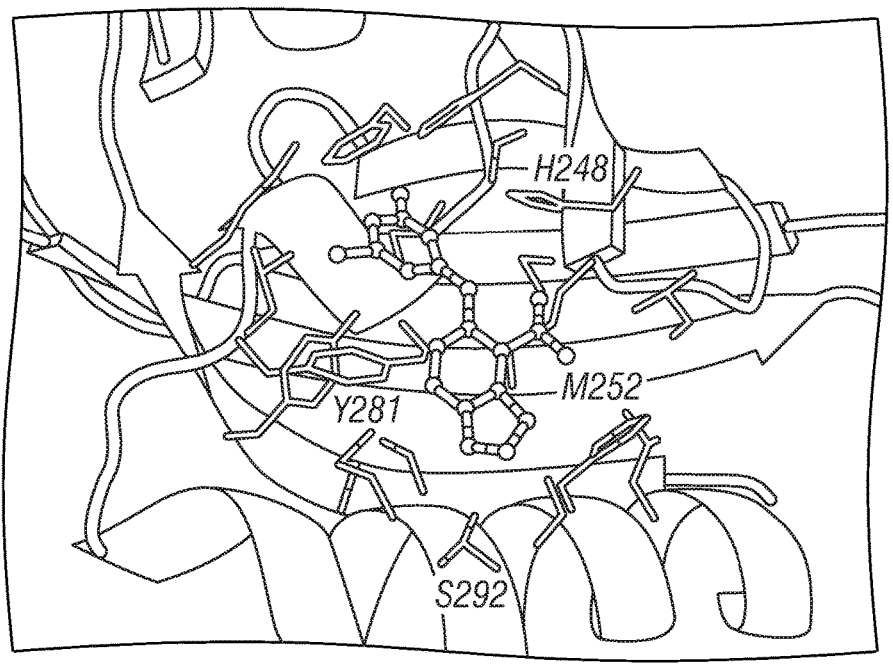
Figure 14C:
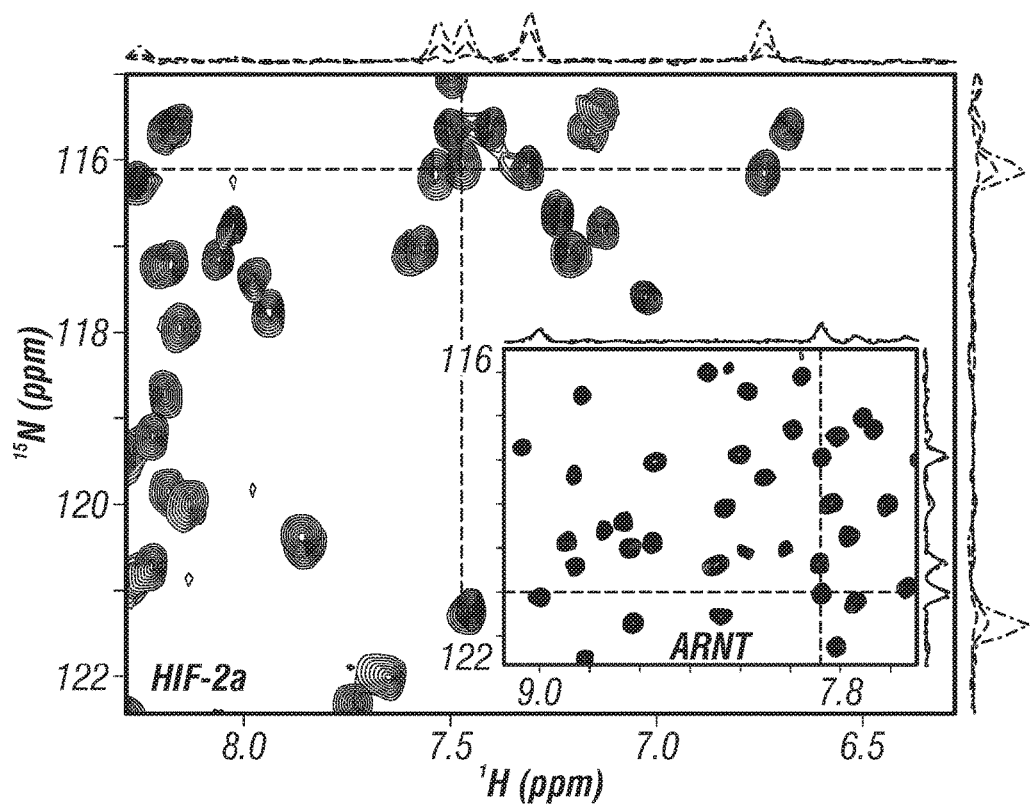
Figure 14D:
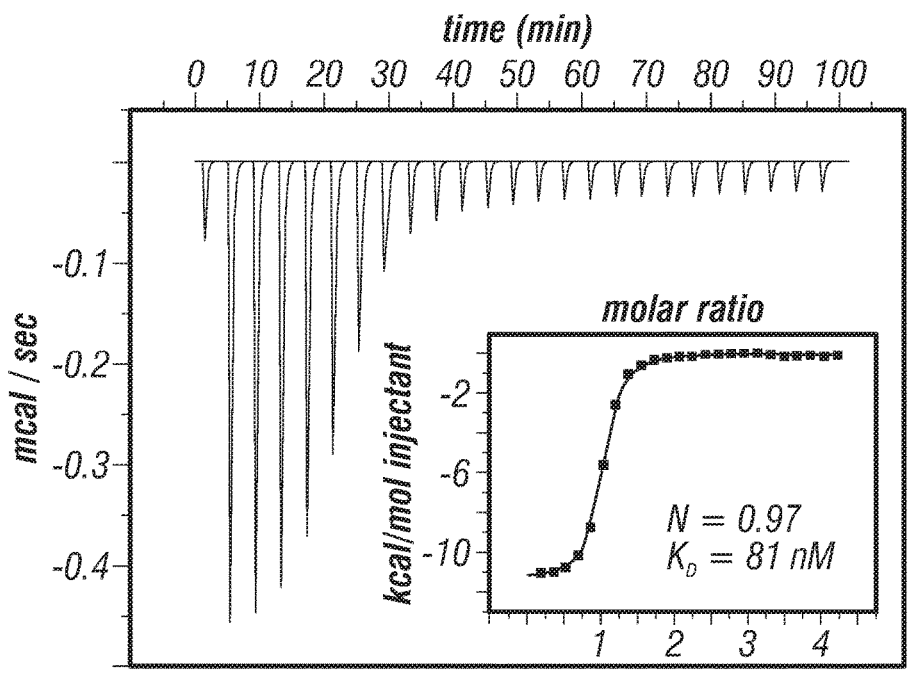

HIF2α Heterodimerization Inhibitor Selectively Disrupts HIF-2α, but not HIF-1α, Activity in Cultured Cells No overt toxicity was observed for 786-0 cells incubated with as much as 30 µM Compound 1 (FIG. 13). 786-0 cells, derived from a human renal cell carcinoma, lack functional pVHL and constitutively accumulate HIF-2α under normoxic conditions. These cells also lack detectable HIF-1α expression so that HIF-dependent regulation of target genes is attributable to HIF-2α isoform. Addition of Compound 1 to cultured 786-0 cells does not alter HIF-2α expression, either at the mRNA (FIG. 5a) or protein levels (FIG. 19b). However, expression of a well-validated HIF-2 target gene (VEGF) was reduced in a dose-dependent manner in 786-0 cells incubated with Compound 1 for 18 hr (FIG. 19a).

To confirm that the mode-of-action for HIF-2α inhibition by Compound 1 is indeed dependent upon binding to the HIF-2α PAS-B, ligand effects on Hep3B cells were examined. While some hypoxia inducible target genes are regulated by both HIF-1α and HIF-2α in these cells, other genes are exclusively regulated by a single isoform. By examining EPO or PGK1 expression as surrogate markers for HIF-2α and HIF-1α, respectively, Hep3B cells were preincubated with 1 or 10 µM Compound 1 for 2 hr and maintained either under normoxic or under hypoxic (1% O2) conditions for 6 or 12 hr. As shown in FIG. 19c, while hypoxia induces both EPO and PGK1 mRNA expression, only hypoxic induction of EPO mRNA is antagonized by Compound 1. Incubation with Compound 1 has no effect on the expression of PGK1 or on the HIF-1α and -2α mRNA levels (FIG. 14).

If Compound 1 is working in cells by antagonizing HIF-2α heterodimerization, HIF-2α's DNA binding activity should likewise be selectively compromised. Chromatin immunoprecipitation (ChIP) using antibodies raised against HIF-1α or HIF-2α was used to measure HIF DNA binding in cultured cells. An increase in both HIF-1α and HIF-2α binding to a HIF-responsive promoter element was observed under hypoxic conditions, reflecting the increase in stability of both a-subunits. However, the DNA-binding activity of HIF-1α was unaffected in cells incubated with 10 µM Compound 1 while HIF-2α's DNA-binding activity is substantially decreased (FIG. 19d). Together these data constitute a proof-of-principle demonstration that small molecule ligands, such as the certain small molecules described herein, can directly and selectively bind to a cavity within the PAS-B domain of the HIF-2α polypeptide. Ligand binding antagonized HIF-2α's DNA binding activity and selectivity reduced expression of HIF-2α target genes in living cells.

ChIP: Experiments were performed as described in Xia, X. et al. Integrative analysis of HIF binding and transactivation reveals its role in maintaining histone methylation homeostasis. *Proc Natl Acad Sci USA* 106, 4260-4265 (2009) using the ChIP-IT Express Enzymatic Kit (Active Motif) according to the manufacturer's protocol. ChIP assays were carried out using normal mouse IgG (Santa Cruz Biotechnology), anti-HIF-2α mouse monoclonal antibody (Novus Biologicals), or anti-HIF-1α mouse monoclonal antibody (BD Biosciences). The precipitated genomic DNA was analyzed by qPCR using the primers for a human EPO enhancer amplicon (ACTCCTGGCAGCAGTGCAGC; CCCTCTCCTTGATGACAATCTCAGC). The captured genomic DNA was measured by normalizing with that of input material and compared between sample.

What is claimed is:

1. A bound HIF-2α PAS-B domain comprising a small molecule bound to at least four or more amino acids selected from the group consisting of PHE-244, SER-246, HIS-248, MET-252, PHE-254, ALA-277, PHE-280, TYR-281, MET-289, SER-292, HIS-293, LEU-296, VAL-302, VAL-303, SER-304, TYR-307, MET-309, LEU-319, THR-321, GLN-322, GLY-323, ILE-337, CYS-339, and ASN-341 of said HIF-2α PAS-B domain, wherein said small molecule is a compound of formula:

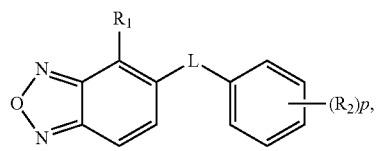

or a pharmaceutically acceptable salt thereof, wherein:
L is selected from NH and NH(CH$_2$);
R$_1$ is NO$_2$;
R$_2$ is independently selected from NO$_2$, halo, and alkyl optionally substituted with at least one halo; and
p is 1, 2, 3, 4, or 5.

2. The bound HIF-2α PAS-B domain of claim 1, wherein said small molecule is selected from the group consisting of:

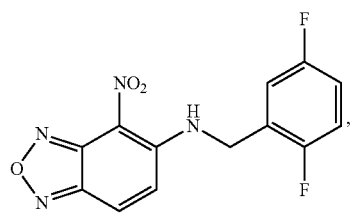

N-(2,5-difluorobenzyl)-4-nitrobenzo[c][1,2,5]oxadiazol-5-amine

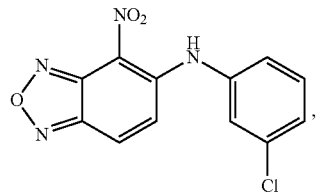

N-(3-chlorophenyl)-4-nitrobenzo[c][1,2,5]oxadiazol-5-amine

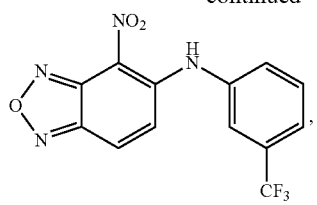

4-nitro-N-(3-(trifluoromethyl)phenyl)benzo[c][1,2,5]oxodiazol-5-amine

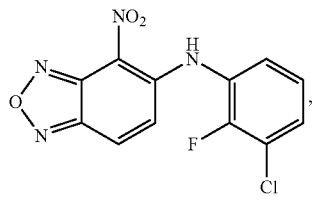

N-(3-chloro-2-fluorophenyl)-4-nitrobenzo[c][1,2,5]oxadiazol-5-amine

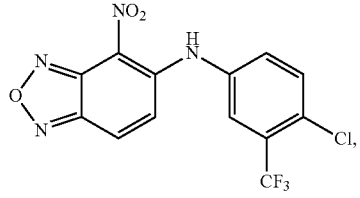

N-(4-chloro-3-(trifluoromethyl)phenyl)-4-nitrobenzo[c][1,2,5]oxadiazol-5-amine

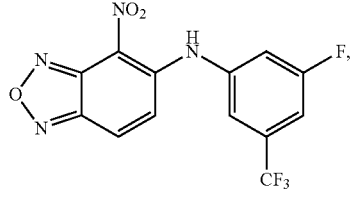

N-(3-fluoro-5-(trifluoromethyl)phenyl)-4-nitrobenzo[c][1,2,5]oxadiazol-5-amine

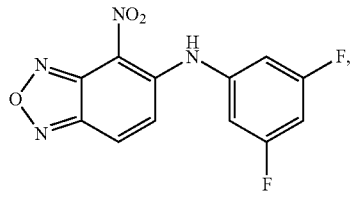

N-(3,5-difluorophenyl)-4-nitrobenzo[c][1,2,5]oxadiazol-5-amine

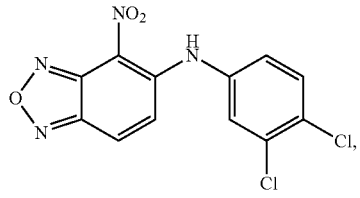

N-(3,4-diclorophenyl)-4-nitrobenzo[c][1,2,5]oxadiazol-5-amine

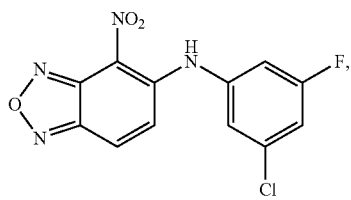

N-(3-chloro-5-fluorophenyl)-4-nitrobenzo[c][1,2,5]oxadiazol-5-amine

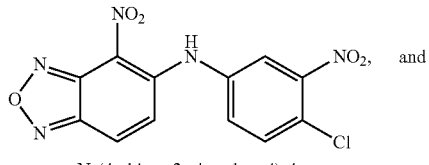

N-(4-chloro-3-nitrophenyl)-4-nitrobenzo[c][1,2,5]oxadiazol-5-amine

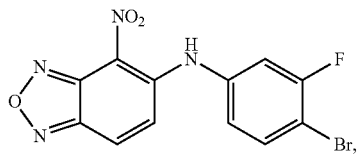

N-(4-bromo-3-fluorophenyl)-4-nitrobenzo[c][1,2,5]oxadiazol-5-amine or a pharmaceutically acceptable salt thereof.

3. The bound HIF-2α PAS-B domain of claim 1, wherein $R_2$ is independently selected from halo, methyl, and methyl substituted with at least one fluoro.

4. The bound HIF-2α PAS-B domain of claim 1, wherein p is 1 or 2.

5. The method of claim 1, wherein said compound is selected from the group consisting of:

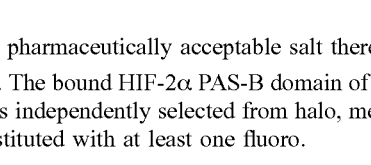

N-(2,5-difluorobenzyl)-4-nitrobenzo[c][1,2,5]oxadiazol-5-amine

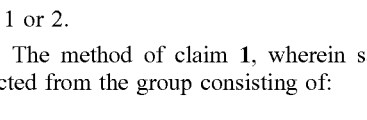

N-(3-chlorophenyl)-4-nitrobenzo[c][1,2,5]oxadiazol-5-amine

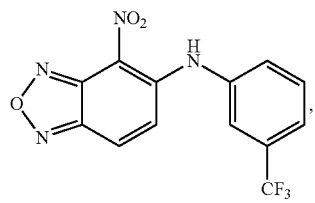

4-nitro-N-(3-(trifluoromethyl)phenyl)benzo[c][1,2,5]oxadiazol-5-amine

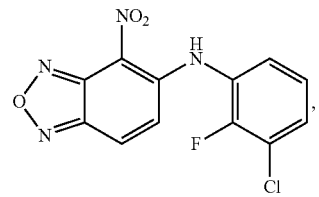

N-(3-chloro-2-fluorophenyl)-4-nitrobenzo[c][1,2,5]oxadiazol-5-amine

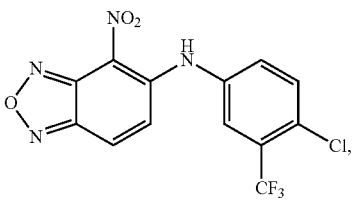

N-(4-chloro-3-(trifluoromethyl)phenyl)-4-nitrobenzo[c][1,2,5]oxadiazol-5-amine

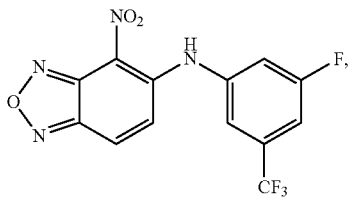

N-(3-fluoro-5-(trifluoromethyl)phenyl)-4-nitrobenzo[c][1,2,5]oxadiazol-5-amine

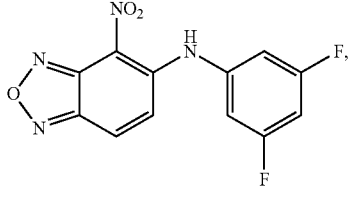

N-(3,5-difluorophenyl)-4-nitrobenzo[c][1,2,5]oxadiazol-5-amine

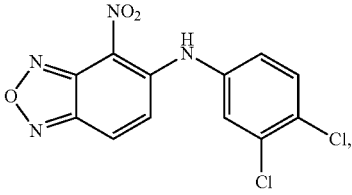

N-(3,4-dichlorophenyl)-4-nitrobenzo[c][1,2,5]oxadiazol-5-amine

-continued
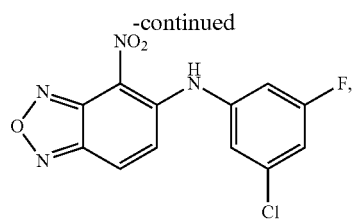
N-(3-chloro-5-fluorophenyl)-4-nitrobenzo[c][1,2,5]oxadiazol-5-amine
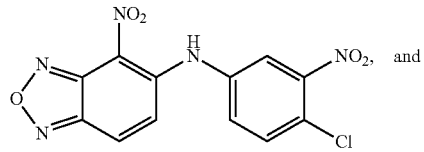
N-(4-chloro-3-nitrophenyl)-4-nitrobenzo[c][1,2,5]oxadiazol-5-amine
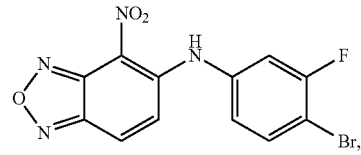
N-(4-bromo-3-fluorophenyl)-4-nitrobenzo[c][1,2,5]oxadiazol-5-amine
or a pharmaceutically acceptable salt thereof.
or a pharmaceutically acceptable salt thereof.
* * * * *

UNITED STATES PATENT AND TRADEMARK OFFICE
CERTIFICATE OF CORRECTION

PATENT NO. : 9,757,379 B2  Page 1 of 1
APPLICATION NO. : 14/442485
DATED : September 12, 2017
INVENTOR(S) : Richard K. Bruick et al.

It is certified that error appears in the above-identified patent and that said Letters Patent is hereby corrected as shown below:

In the Claims

In Claim 2, Column 66, Line 11, delete "oxodiazol" and insert --oxadiazol-- therefor.

In Claim 2, Column 66, Line 65, delete "diclorophenyl" and insert --dichlorophenyl-- therefor.

In Claim 5, Column 69, Line 27, delete first occurrence of "or a pharmaceutically acceptable salt thereof.".

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

PATENT NO. : 9,757,379 B2  
APPLICATION NO. : 14/442485  
DATED : September 12, 2017  
INVENTOR(S) : Richard K. Bruick et al.

Page 1 of 1

It is certified that error appears in the above-identified patent and that said Letters Patent is hereby corrected as shown below:

In the Specification

Column 1, Lines 17-31, delete paragraph and insert:
--This invention was made with government support under grant number CA095471 awarded by The National Institutes of Health. The government has certain rights in the invention.-- therefor.

Signed and Sealed this  
Seventh Day of July, 2020

Andrei Iancu  
*Director of the United States Patent and Trademark Office*